United States Patent
Hansen et al.

(10) Patent No.: US 10,107,798 B2
(45) Date of Patent: Oct. 23, 2018

(54) METHODS OF CHEMOTYPE EVOLUTION

(75) Inventors: Stig Hansen, Kensington, CA (US); Daniel Erlanson, San Francisco, CA (US); Mark Cancilla, San Mateo, CA (US)

(73) Assignee: SUNESIS PHARMACEUTICALS, INC., South San Francisco, CA (US)

( * ) Notice: Subject to any disclaimer, the term of this patent is extended or adjusted under 35 U.S.C. 154(b) by 1116 days.

(21) Appl. No.: 12/934,265

(22) PCT Filed: Mar. 25, 2009

(86) PCT No.: PCT/US2009/038276
§ 371 (c)(1),
(2), (4) Date: Dec. 16, 2010

(87) PCT Pub. No.: WO2009/120795
PCT Pub. Date: Oct. 1, 2009

(65) Prior Publication Data
US 2011/0118126 A1    May 19, 2011

Related U.S. Application Data

(60) Provisional application No. 61/039,422, filed on Mar. 25, 2008, provisional application No. 61/045,265, filed on Apr. 15, 2008, provisional application No. 61/048,545, filed on Apr. 28, 2008.

(51) Int. Cl.
| | | |
|---|---|---|
| *G01N 33/50* | (2006.01) | |
| *G01N 33/531* | (2006.01) | |
| *C12Q 1/48* | (2006.01) | |

(52) U.S. Cl.
CPC ........... *G01N 33/531* (2013.01); *C12Q 1/485* (2013.01)

(58) Field of Classification Search
None
See application file for complete search history.

(56) References Cited

U.S. PATENT DOCUMENTS

| | | | | |
|---|---|---|---|---|
| 5,872,015 | A * | 2/1999 | Venton et al. | 436/538 |
| 7,601,725 | B2 * | 10/2009 | Lew et al. | 514/260.1 |
| 2003/0104471 | A1 | 6/2003 | Wells et al. | |
| 2005/0079547 | A1 * | 4/2005 | Michnick | A01K 67/0271 435/7.1 |
| 2005/0287596 | A9 * | 12/2005 | Braisted et al. | 435/7.1 |

FOREIGN PATENT DOCUMENTS

| | | |
|---|---|---|
| WO | WO 1999/049314 A1 | 9/1999 |
| WO | WO 2000/000823 A1 | 1/2000 |

OTHER PUBLICATIONS

Chapman et al (1993 J. Med. Chem 36:4293-4301).*
Zhao et al (1997 J. Med. Chem. 40:4006-12).*
Erlanson, et al., "Making Drugs on Proteins: Site-Directed Ligand Discovery for Fragment-Based Lead Assembly," *Curr. Opin. Chem. Biol.* 2004, 8 (4), 399-406.
Erlanson, et al., "Fragment-based Drug Discovery," *J. Med. Chem.* 2004, 47 (14), 3463-3482.
Erlanson, et al., "Site-Directed Ligand Discovery," *Proc. Natl. Acad. Sci. U.S.A.* 2000, 97 (17), 9367-9372.
Maly, et al., "Combinatorial Target-Guided Ligand Assembly: Identification of Potent Subtype-Selective c-Src Inhibitors," *Proc. Natl. Acad. Sci. U.S.A.* 2000, 97 (6), 2419-2424.

* cited by examiner

*Primary Examiner* — Christopher M Gross
(74) *Attorney, Agent, or Firm* — Morgan, Lewis & Bockius LLP; Jeffrey S. Mann; Todd Esker

(57) ABSTRACT

Herein is described a method to rapidly screen a large chemical space for a compound that binds to a target protein through an iterative fragment assembly approach that can be performed at low reagent cost and without requiring purification of the assembled product. The method employs a library of test ligands each of which comprise a 'bait' molecule, which is known from prior art or prior screening to have some intrinsic affinity for the target protein, and a test moiety.

57 Claims, 12 Drawing Sheets

A

B

METHODS OF CHEMOTYPE EVOLUTION

CROSS-REFERENCE TO RELATED APPLICATIONS

The present invention is a U.S. national phase application of PCT Application No. PCT/US2009/038276 filed Mar. 25, 2009, and claims priority under 35 U.S.C. § 119(e) to U.S. provisional application Ser. No. 61/039,422, filed Mar. 25, 2008, U.S. provisional application Ser. No. 61/045,265, filed Apr. 15, 2008, and U.S. provisional application Ser. No. 61/048,545, filed Apr. 28, 2008, the entirety of each of which is hereby incorporated herein by reference for all purposes.

BACKGROUND OF THE INVENTION

Initial chemical approaches to the production of libraries by conventional techniques may be led by a random approach to structure design, computational chemistry and predictive modeling, analogue design based on compounds with known structure and activity, medicinal chemistry intuition, or combinations of these approaches. The libraries of compounds so produced are then screened for activity against targets of interest.

The use of combinatorial chemistry to accelerate the identification of new chemical entities with desirable properties is well established. For example, in drug discovery, large collections of compounds are often synthesized very quickly using techniques collectively called "combinatorial chemistry." These techniques can include the parallel synthesis of compound libraries using automated and non-automated methods, and may employ both solution phase and solid phase chemistry. Such libraries may be collections of discrete, individual compounds or may consist of collections of mixed or pooled compounds, which are then screened against a target of interest. Pharmaceutically useful properties may be identified through a basic screen developed to assay the ability of compounds to bind to a molecular target. If mixtures of compounds are screened, a deconvolution process is often necessary to identify the components of a mixture that are responsible for any observed activity in the screening process. This can prove difficult to achieve in practice.

Scientists must sift through enormous numbers of potential drug candidates in their search for a single, effective drug. In many ways such high throughput screening processes have not effectively accelerated identification of new chemical entities with desirable properties.

Fragment-based drug discovery has received significant industry attention since Fesik and co-workers demonstrated that high-affinity ligands could be generated by first identifying and then combining small fragments that bound to adjacent sites on a target protein. Shuker, S. B., et al., *Science* 274, 1531-1534 (1996); Petros, A. M., et al., *J. Med. Chem.* 49, 656-663 (2006); Hajduk, P. J., et al., *J. Am. Chem. Soc.* 119, 5818-5827 (1997). Lead generation by fragment assembly offers an attractive complement to traditional screening: small fragments are less likely to contain interfering groups that could block an otherwise productive binding interaction, and combining prequalified fragments greatly simplifies the combinatorial search problem. Although productive techniques have been developed to identify and optimize individual fragments, the goal of merging two or more fragments to generate high-affinity compounds remains a significant challenge due to the difficulty of identifying suitable linking moieties. Erlanson, D. A., et al., *J. Med. Chem.* 47, 3463-3482 (2004); Jahnke, W. & Erlanson, D. A. (eds.) *Fragment-based approaches in drug discovery* (Wiley-VCH, Weinheim, Germany, 2006). This challenge is particularly daunting when a protein target is not amenable to structural studies, illustrating the need for simple empirical solutions to the linking problem. Tethering® with Extenders provides one such solution in which a given site on a protein is occupied by a covalently attached extender and disulfide capture is used to identify companion fragments that bind to an adjacent site. Erlanson, D. A., et al., *Nat. Biotechnol.* 21, 308-314. (2003); Choong, I. C., et al., *J. Med. Chem.* 45, 5005-5022 (2002). Initially validated using protease targets, Tethering with Extenders has recently been used to identify highly selective inhibitors of protein kinases by targeting an adaptive site adjacent to the "hinge region". However, the high investment in protein engineering and production required to support structure-based methods or Tethering with Extenders can limit the extent to which these approaches can be routinely used.

Although such fragment-based methods have proven their utility in the development of lead candidates for medicinal chemistry optimization, there remains a need for simple, inexpensive, fast, and efficient generation of pharmacophore hits that have structures amenable to medicinal chemistry and that demonstrate affinity for or activity against biological targets of interest.

SUMMARY OF THE INVENTION

We describe a method to rapidly screen a large chemical space for a compound that binds to a target biological molecule through an iterative fragment assembly approach that can be performed at low reagent cost and without requiring purification of the assembled product. In one embodiment, the method employs a library of specially constructed test ligands, each of which comprises a "bait" moiety, which is preselected on the basis of information known about it and/or the target, linked to one of a plurality of naïve test moieties.

DETAILED DESCRIPTION OF THE INVENTION

The invention provides, inter alia, methods for fragment-based ligand evolution. The invention is a second-generation strategy that provides the empirical advantages of Tethering with Extenders, but in a streamlined, flexible process requiring only small amounts protein. The process starts by selecting a low molecular weight anchor fragment or "bait" that interacts with the target of interest. The bait can be derived from existing information (known inhibitors, substrates, or co-factors) or discovered using fragment screening approaches such as Tethering. The bait fragment contains a reactive functionality that enables it to be linked with every member of a test fragment collection (naïve or directed) to generate a library of 2-component putative ligands (referred to herein as test ligands) that are biased towards the target of interest. The 2-component molecules are then tested for binding to or functional inhibition of the target protein to identify productive bait-companion combinations. This process can be repeated using selected test fragments identified in a prior screen as new "baits" to identify replacements for the initial anchoring fragment.

We describe a method to rapidly survey a large chemical space through an iterative fragment assembly approach that can be performed at low reagent cost and without the need for purification of the assembled product. Importantly, the test ligand assembly reaction can be performed in the absence of target and can, therefore, be conducted under denaturing conditions. This is in contrast to dynamic combinatorial chemistry methods known in the art, in which fragments are assembled in presence of the receptor and therefore generally occurs under conditions that preserve receptor integrity. In one aspect, conducting fragment assembly under denaturing conditions as described herein allows the use of a multitude of different chemistries and presents new opportunities for introducing chemical diversity.

Figure 1:
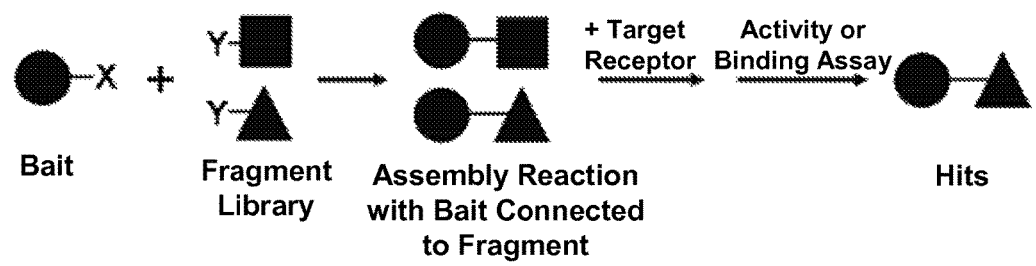
FIG. 1 shows generalized illustrations of fragment assembly according to the method of the invention. (A) A bait fragment and test fragment molecules contain reactive groups (X and Y, respectively) that connect the two molecules under appropriate reaction conditions to provide assembled test ligands. Assembly reactions are then screened individually, e.g., in an enzyme or ligand-binding assay, to identify assembly reactions yielding affinity for the target receptor, i.e., "hits." (B) An embodiment in which a thiol bait fragment is coupled to 5,000 test fragments of a disulfide fragment library, for use in a high throughput screen using target inhibition as a read-out for binding to permit discrimination of higher affinity hits from lower affinity test ligands.
Figure 1:
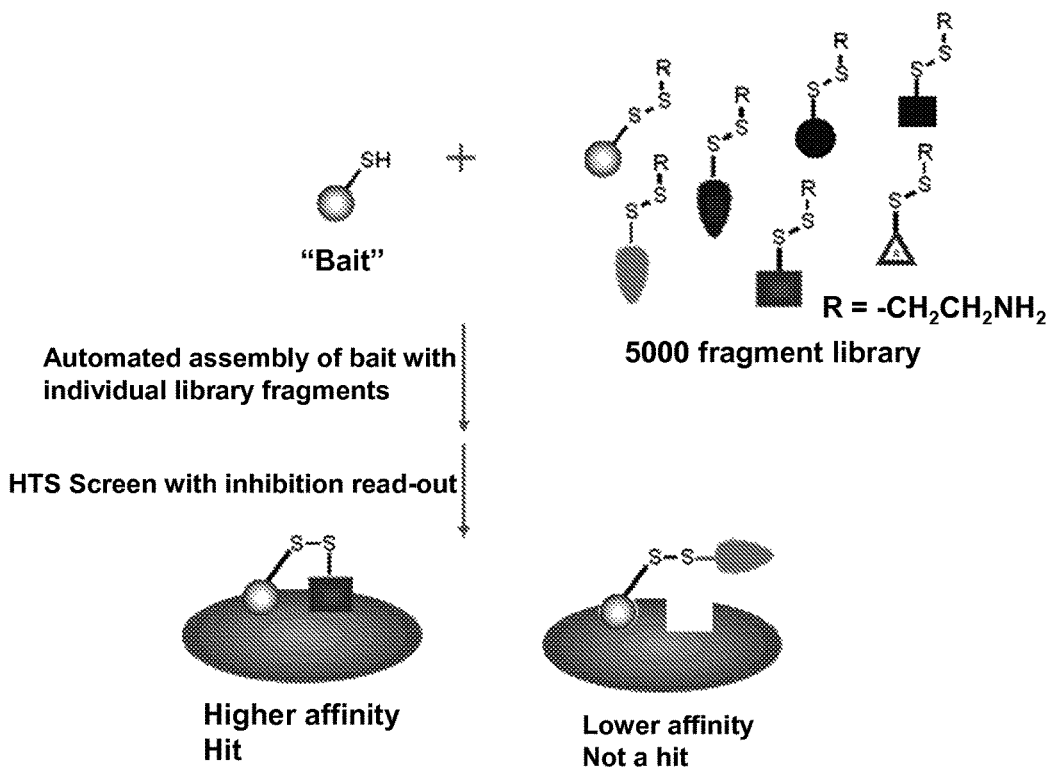
Figure 8:
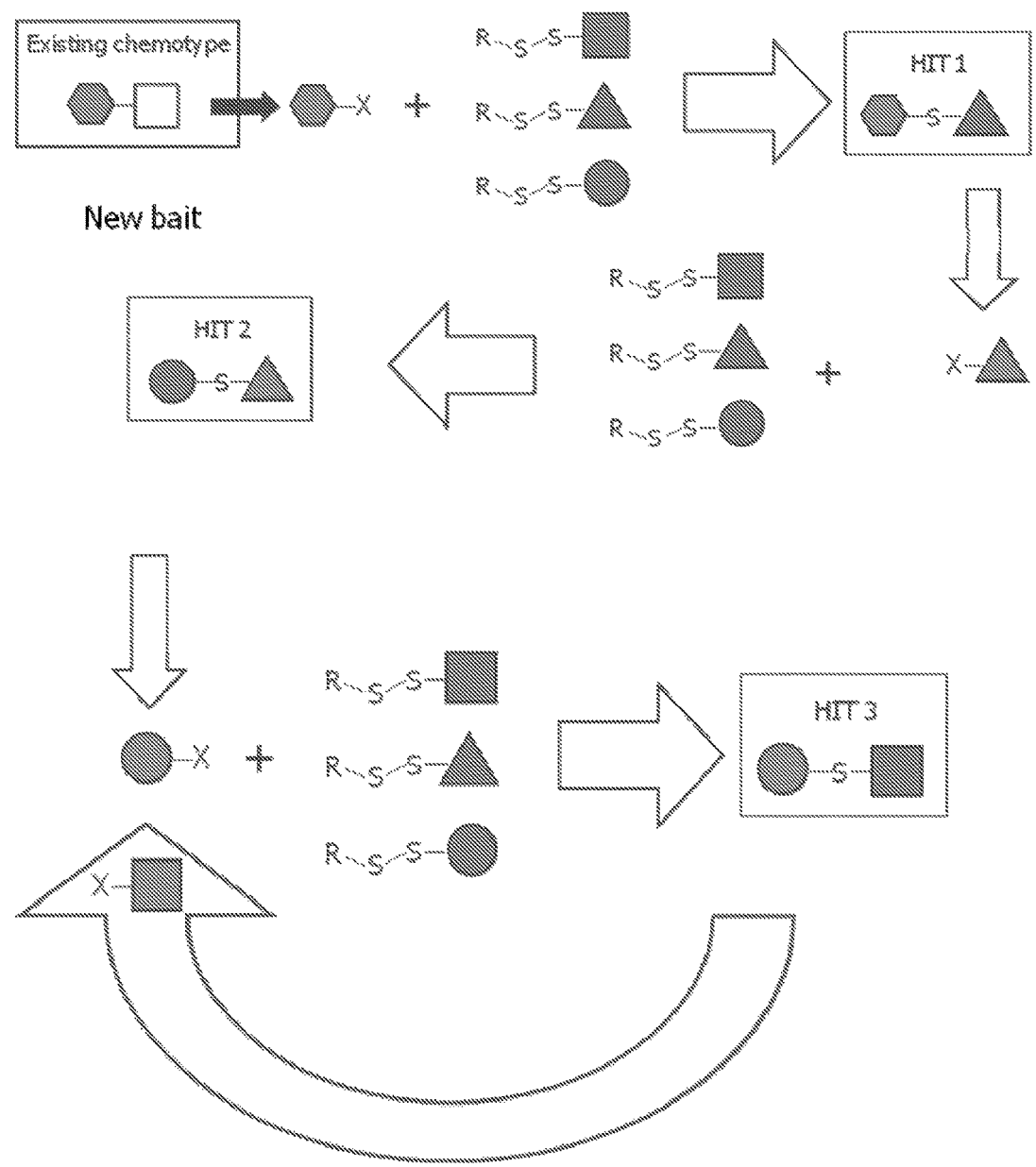
FIG. 8 provides a generalized illustration of an embodiment of iterative chemotype evolution according to the invention, using a disulfide library. A portion of a known chemotype is derivatized and used to screen disulfide library members. Once a hit (Hit 1) is obtained, the novel portion of the hit is derivatized and used to screen the library again for a new hit molecule (Hit 2). Once Hit 2 is obtained, the novel portion identified in the screen is derivatized and used to screen the library again to obtain Hit 3. In principle, the procedure can be repeated until a satisfactory lead is identified.

The principle of this method is illustrated in FIG. 1, where a fixed, preselected fragment, the "bait", is combined with individual fragments from a fragment library under conditions where the bait forms a covalent bond with the library fragment, thereby forming a test ligand. In one embodiment of the present application, the reaction mixture of the test ligand is not purified and is diluted to the appropriate conditions for screening and tested for binding affinity towards the target receptor in an enzymatic activity assay or ligand binding assay. In another embodiment of the present application, the test ligand is purified from its reaction mixture and is then tested for binding affinity. The procedures disclosed herein may be iterated one or more times, for example, as illustrated in FIG. 8.

Fragment-based ligand evolution according to the invention is capable of generating multiple chemical series with a desired activity profile. The combined use of validated baits and a pre-formed collection of test fragments provides an efficient, empirical solution to the "linking challenge." The linking chemistry enables rapid, quantitative generation of two-component test ligands without the need for purification. A cycle of fragment assembly, screening, and hit follow-up can be completed within 2 weeks. Unlike combinatorial chemistry, where a static library is screened once against a given target, the libraries created by fragment assembly according to the invention can evolve under selection pressure through iterative cycles of linking and screening. This selection pressure can be further amplified by counter-screening between each cycle to bias the selection of fragments and baits towards combinations that afford the desired properties. The resulting compounds contain simple flexible linkers that can be easily replaced to generate high-affinity hits with molecular weights in the 375-500 Da range.

Fragment-based ligand evolution according to the invention can be readily applied to any target that recognizes multivalent ligands. Ideal candidates for this approach include, e.g., enzymes where effective inhibitors span both substrate and cofactor sites and targets that recognize peptides or other ligands that bind to distinct subsites. The process of library evolution can be guided by different selection methods including biochemical inhibition, displacement of a known ligand, or direct binding detection by mass spectrometry. The latter embodiments allow the identification of compounds that bind to and stabilize inactive states of an enzyme. Unlike most other fragment approaches, fragment-based ligand evolution according to the invention can be conducted using large proteins, protein complexes, or partially pure fractions derived from cell extracts.

Unless specifically noted otherwise herein, the definitions of the terms used are standard definitions used in the art of organic and peptide synthesis, medicinal chemistry, and pharmaceutical sciences.

The term "target" means a chemical or biological entity for which a ligand has intrinsic binding affinity. The target can be a molecule, a portion of a molecule, or an aggregate of molecules. Specific examples of targets include polypeptides, proteins, ligands for receptors, allosteric enzyme regulators, immunoglobulins, polynucleotides, carbohydrates, glycolipids, and other macromolecules, such as protein complexes, nucleic acid-protein complexes, chromatin, ribosomes, lipid bilayer-containing structures, such as membranes, or structures derived from membranes, such as vesicles.

As used herein, "protein" means any molecule comprising two or more peptide units, each comprising an amino acid residue, arranged in a linear chain and joined together by peptide bonds. Protein chains comprising more than 30 amino acid residues may be referred to as polypeptides. Protein chains of 30 amino acid residues or fewer may be referred to as oligopeptides. Proteins include, but are not limited to, enzymes (e.g., cysteine protease, serine protease, and aspartyl proteases), receptors, transcription factors, growth factors, cytokines, immunoglobulins, nuclear proteins, signal transduction components (e.g., kinases, phosphatases), and glycoproteins.

"Polynucleotide," as used herein in singular or plural, means any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" includes DNAs and RNAs that contain one or more modified bases. Thus, for example, DNAs or RNAs with backbones modified for stability or for other reasons are "polynucleotides" as that term is intended herein. Moreover, DNAs or RNAs comprising unusual bases, such as inosine, or modified bases, such as tritylated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

A "ligand" as defined herein is a molecule that has an intrinsic binding affinity for the target. Ligands are typically small organic molecules that have an intrinsic binding affinity for the target, but may also be other sequence-specific binding molecules, such as peptides (D-, L-, or a mixture of D- and L-), peptidomimetics, complex carbohydrates, or other oligomeric molecules that bind specifically to the target.

As used herein "bait moiety" means a chemical compound preselected for use in the method of the invention, and is also denoted as "B". By "preselected" is meant that the skilled person will have identified the moiety as having potential utility as a reference or anchor for the development of potential ligands for a target. For example, a bait moiety may be selected on the basis of having a measurable, preferably previously measured, binding affinity for the target. Alternatively, a bait moiety may be a fragment of a compound, which compound has a measured binding affinity for the target. The bait moiety may comprise a structural analog of a compound, which compound has a measured binding affinity for the target. The binding affinity referred to herein may be directly measurable, or may be measurable indirectly through an affinity parameter as that term is defined hereinbelow.

A bait moiety may be identified logically as a radical or substructure of a compound already known to modulate the activity of a target. However, by abstracting a bait moiety from a larger chemical structure, it is necessary to derive a structure for the bait that would be consistent with being an independent stable molecule. Thus, for a bait moiety that is a radical bonded to one or more atoms in a larger compound, one may conceive of the free bait moiety as being cleavage product or derivative of the larger compound. It is not necessary to synthesize a bait moiety to perform the method of the invention, although it may be possible and even desirable to do so. More commonly, the skilled chemist will develop a synthetic process that will assemble the bait moiety in the context of a bait fragment, i.e., already comprising a reactive functionality x. Intermediate compounds may also be synthesized that will enable attachment or unblocking of the reactive functionality of a bait fragment.

As used herein "bait fragment" means a compound that comprises a bait moiety B and a reactive functionality of interest, denoted "x". Thus a bait fragment may be denoted "B-x". The reactive functionality x may be a chemical functional group in the structure of a bait moiety, but typically a reactive functionality is provided as part of, or added to, the bait moiety by chemical means.

As used herein "test moiety" means a compound that may have an intrinsic binding affinity for the target and is a component of a test ligand, and may be denoted as "T".

As used herein "test fragment" (y-T) refers to a test moiety T bound to a reactive functionality y. A test fragment (y-T) is selected to permit reaction with the bait fragment (x-B) to yield a test ligand, denoted "(B-z-T)", in which the z linker group is a residue of the reaction between the two reactive functionalities x and y.

In the methods of the invention, other than certain physicochemical properties of the individual members of a library of test fragments, it is not required that the test moieties of the test fragments have any known affinity for the target. In this sense, the library of test fragments is said to be "naïve." In practice, however, libraries of test fragments are generally not randomly distributed in a chemical space, but may be structured to omit undesirable chemical structures. For, example, chemical groups known or expected to be toxic or to be pharmaceutically unacceptable may be unrepresented or underrepresented as test moieties in a test fragment library. Alternatively, test fragment libraries may be employed in which certain potentially desirable structures or properties are overrepresented. For example, if a large family of proteins has been subjected to substantial study, such as has been the case with the kinases, a test fragment library may contain an unusually high representation of compounds that are analogs or isosteres of each other. In any case, a library of test fragments may be used in the method of the invention to develop libraries of test ligands for screening screen multiple targets, including targets that are substantially unrelated to one another.

Bait fragments, test ligand libraries, or both, may be chosen or biased using knowledge of the target. For example, for kinases, the bait moiety and/or the test ligands may comprise a purine mimetic. For protease targets, the bait moiety and/or the test ligands may comprise a peptidomimetic.

As used herein a "reactive functionality" means a chemical group capable of undergoing a reaction with a second reactive functionality to yield a linker, and may be denoted as "x" or "y". In general, the reactive functionalities x and y are selected to form upon reaction a stable linker. However, in certain embodiments, it may be useful to choose the reactive functionalities x and y and reaction conditions so as to permit reversible reactions, such as disulfide exchange reactions. In certain embodiments, x and y are the same. In other embodiments, x and y are different. In some embodiments, x and y are independently selected from the group consisting of halo groups, thiols, protected thiols, disulfides, acrylamides, acrylates, vinyl sulfones, epoxides, thiiranes, aziridines, esters, sulfonic acid esters, thioesters, amines, azides, alkynes, alcohols, and phenols. In the various embodiments of the invention, x and y may be independently selected from among halo groups (i.e., Cl, Br, I), thiol groups (i.e., —SH), and disulfide groups —S—SR, where R=hydrogen, methylamino, or ethylamino. In certain embodiments, one of x and y is a halo group and the other comprises a disulfide group. In certain embodiments, one of x and y comprises a thiol or protected thiol and the other comprises a disulfide group. In certain embodiments, one of x and y comprises an azide group and the other comprises an alkyne group.

The allocation of such reactive functionalities between x and y may be determined by the skilled practitioner based on considerations such as speed of reaction, cleanliness of the reaction mixture, reversibility of reaction, etc. In some embodiments, the reactive functionality y and the resulting linker z each comprise a disulfide moiety. In general, it is not material which chemically reactive group of a given pair of chemically reactive groups is on the bait fragment and which is on the test fragments prior to subsequent reaction to form the test ligands.

In some embodiments, the reacting of x and y occurs at physiological conditions. In other embodiments, the reacting occurs under conditions that would disrupt or degrade the target. For example, the reacting may be performed under reducing conditions, such as where a reductant is added to the reaction mixture. Reductants may be selected from those known in the art, including, without limitation, beta-mercaptoethanol, mercaptopropanoic acid, glutathione, cysteamine, dithiothreitol (DTT), dithioerythritol (DTE), cysteine, homocysteine, triphenylphosphine, tris(cyanoethyl)phosphine, and tris-2-carboxyethylphosphine hydrochloride. In some embodiments, the reacting step is performed under conditions permitting reversible reaction of x and y. In some embodiments, the reacting of x and y and the contacting of the target with the reaction mixture may be coincident, or may partially overlap temporally.

The phrases "modified to contain" and "modified to possess" are used interchangeably, and refer to making a mutant, variant or derivative of the target, or the reactive nucleophile or electrophile, including but not limited to chemical modifications. For example, in a protein one can substitute an amino acid residue having a side chain containing a nucleophile or electrophile for a wild-type residue. Another example is the conversion of the thiol group of a cysteine residue to an amine group.

The term "reactive nucleophile" as used herein refers to a nucleophile that is capable of forming a covalent bond through reaction with a compatible functional group, typically an electrophilic group, on another molecule. In certain embodiments, reactive nucleophiles form a covalent bond through reaction with an electrophile under conditions that do not denature or damage the target. Exemplary reactive nucleophiles include, without limitation, thiols, alcohols, activated carbonyls, epoxides, aziridines, aromatic sulfonates, hemiacetals, and amines.

Similarly, the term "reactive electrophile" as used herein refers to an electrophile that is capable of forming a covalent bond with a compatible functional group, typically a nucleophilic group, on another molecule. In certain embodiments, reactive electrophiles form a covalent bond through reaction with a nucleophile under conditions that do not denature or otherwise damage the target. Exemplary reactive electrophiles include, without limitation, imines, carbonyls, epoxides, aziridines, sulfonates, and hemiacetals.

The phrases "nucleophile-reactive group" and "electrophile-reactive group," as used herein, mean functional groups that can form a covalent bond through reaction with a corresponding compatible functional group, i.e., an electrophile or nucleophile, respectively. In certain embodiments, a nucleophile-reactive group or electrophile-reactive group forms a covalent bond through reaction with a corresponding compatible functional group, i.e., an electrophile or nucleophile, respectively, under conditions that do not denature or otherwise damage the target.

The phrase "reversible covalent bond" as used herein means a covalent bond which can be broken, generally under conditions that do not denature the target. Examples include, without limitation, disulfides, Schiff-bases, thioesters, and the like.

Various chemistries may be employed for chemically reacting the bait fragment with the library of test fragments. Chemistries available for forming a reversible or irreversible covalent bond between a bait fragment and a test fragment are known in the art, and are described in basic textbooks, such as, e.g. March, *Advanced Organic Chemistry*, John Wiley & Sons, New York, 4$^{th}$ edition, 1992. The chemistries include, for example, reductive aminations between aldehydes or ketones and amines are described, for example, in March et al., supra, at pp. 898-900; alternative methods for preparing amines at p. 1276; reactions between aldehydes or ketones and hydrazide derivatives to give hydrazones and hydrazone derivatives such as semicarbazones at pp. 904-906; amide bond formation at p. 1275; formation of ureas at p. 1299; formation of thiocarbamates at p. 892; formation of carbamates at p. 1280; formation of sulfonamides at p. 1296; formation of thioethers at p. 1297; formation of disulfides at p. 1284; formation of ethers at p. 1285; formation of esters at p. 1281; additions to epoxides at p. 368; additions to aziridines at p. 368; formation of acetals and ketals at p. 1269; formation of carbonates at p. 392; formation of denamines at p. 1264; metathesis of alkenes at pp. 1146-1148 (see also Grubbs et al., *Acc. Chem. Res.* 28:446-453 [1995]); transition metal-catalyzed couplings of aryl halides and sulfonates with alkanes and acetylenes, e.g., Heck reactions, at p.p. 717-178; the reaction of aryl halides and sulfonates with organometallic reagents, such as organoboron reagents, at p. 662 (see also Miyaura et al., *Chem. Rev.* 95:2457 [1995]); organotin, and organozinc reagents, formation of oxazolidines (Ede et al., *Tetrahedron Letts.* 28:7119-7122 [1997]); formation of thiazolidines (Patek et al., *Tetrahedron Letts.* 36:2227-2230 [1995]); amines linked through amidine groups by coupling amines through imidoesters (Davies et al., *Canadian J. Biochem.* c50:416-422 [1972]), reactions between aldehydes or ketones and O-alkyl-hydroxylamine derivatives to give oximes (Maly et al., *Proc. Nat. Acad. Sci. USA* 97:2419-2424 [2000]); and the like. Additionally, the Huisgen 1,3-dipolar cycloaddition of azides and acetylenes can give 1,2,3-triazoles (Lewis et al., *Angew. Chem. Int. Ed. Engl.* 41:1053-1047 [2002]). In particular, disulfide-containing small molecule libraries may be made from commercially available carboxylic acids and protected cysteamine (e.g., mono-BOC-cysteamine) by adapting the method of Parlow et al., *Mol. Diversity* 1:266-269 (1995). All of the references cited in this section are hereby expressly incorporated by reference for all that they disclose.

The phrase "exchangeable disulfide reactive functionality" when used herein to describe reactive groups of disulfide libraries refers to libraries where each member contains a disulfide group that can react with a thiol or a protected thiol displayed on a bait fragment to form a new disulfide bond when the reaction conditions are adjusted to favor such thiol exchange.

The term "protected thiol" as used herein means a thiol that has been reacted with a group or molecule to form a covalent bond that renders it less reactive and which may be deprotected to regenerate a free thiol.

In some embodiments of the methods provided herein, each member of the library of test fragments has a structure of the formula:

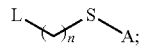

wherein A is —S(CH$_2$)$_p$R$^{A1}$ or —S(O)$_2$R$^{A2}$, wherein p is 1-5, R$^{A1}$ is —NR$^{A3}$R$^{A4}$; OR$^{A3}$; SR$^{A3}$; —NHCOR$^{A3}$; —NHCONR$^{A3}$R$^{A4}$; —NR$^{A3}$R$^{A4}$R$^{A5+}$X$^-$, wherein X is a halogen; —COOR$^{A3}$; CONR$^{A3}$R$^{A4}$; —SO$_3$R$^{A3}$; —OPO$_3$R$^{A3}$; —SO$_2$R$^{A3}$; and wherein R$^{A2}$ is an aliphatic, heteroaliphatic, aryl, or heteroaryl moiety, and each occurrence of R$^{A3}$, R$^{A4}$, and R$^{A5}$ is independently hydrogen, a protecting group, or an aliphatic, heteroaliphatic, aryl, or heteroaryl moiety; n is 0-5, optionally n is 1-4;

L is a moiety having one of the structures:

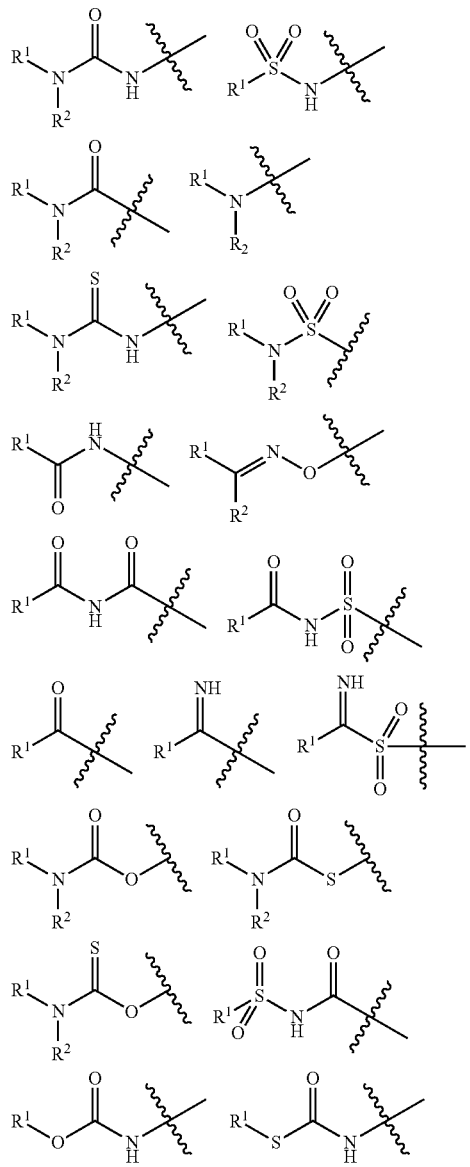

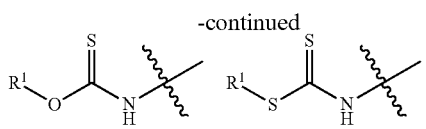

each occurrence of $R^1$ and $R^2$ is independently hydrogen, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety, or wherein $R^1$ and $R^2$ taken together are a cycloaliphatic, heterocycloaliphatic, aryl or heteroaryl moiety;

wherein each of the foregoing aliphatic and heteroaliphatic moieties is substituted or unsubstituted, linear or branched and each of the foregoing cycloaliphatic, heterocycloaliphatic, aryl or heteroaryl moieties is independently substituted or unsubstituted.

Examples of substituents include, but are not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$;— or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety.

In other embodiments, each member of the library of test fragments has a structure of the formula:

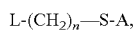

wherein L is an aliphatic, heteroaliphatic, aryl or heteroaryl moiety; n is 0-5 (optionally 0-2); A is —$S(CH_2)_pR^{A1}$, wherein p is 1-5, $R^{A1}$ is —$NR^{A3}R^{A4}$; $OR^{A3}$; $SR^{A3}$; —$NHCOR^{A3}$; —$NHCONR^{A3}R^{A4}$; —$NR^{A3}R^{A4}R^{A5}+X^-$, wherein X is a halogen; —$COOR^{A3}$; $CONR^{A3}R^{A4}$; —$SO_3R^{A3}$; —$OPO_3R^{A3}$; —$SO_2R^{A3}$; and each occurrence of $R^{A3}$, $R^{A4}$, and $R^{A5}$ is independently hydrogen, a protecting group, or an aliphatic, heteroaliphatic, aryl, or heteroaryl moiety;

wherein each of the foregoing aliphatic and heteroaliphatic moieties is substituted or unsubstituted, linear or branched and each of the foregoing cycloaliphatic, heterocycloaliphatic, aryl or heteroaryl moieties is independently substituted or unsubstituted.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl-n, cyclohexyl, —$CH_2$-cyclohexyl, cyclohexenylethyl, cyclohexanylethyl, norbornyl moieties and the like, which again, may bear one or more substituents.

The term "cycloalkyl", as used herein, refers specifically to cyclic alkyl groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, i.e., in place of carbon atoms. Thus, a 1-6 atom heteroaliphatic linker having at least one N atom in the heteroaliphatic main chain, as used herein, refers to a $C_{1-6}$aliphatic chain wherein at least one carbon atom is replaced with a nitrogen atom, and wherein any one or more of the remaining 5 carbon atoms may be replaced by an oxygen, sulfur, nitrogen, phosphorus or silicon atom. As used herein, a 1-atom heteroaliphatic linker having at least one N atom in the heteroaliphatic main chain refers to —NH— or —NR— where R is aliphatic, heteroaliphatic, acyl, aromatic, heteroaromatic or a nitrogen protecting group. Heteroaliphatic moieties may be branched or linear unbranched. In certain embodiments, heteroaliphatic moieties are substituted by independent replacement of one or more of the hydrogen atoms thereon with one or more moieties including, any of the substituents described above.

The term "heteroalicyclic", "heterocycloalkyl" or "heterocyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl, etc., which are optionally substituted with one or more functional groups, as defined herein. In certain embodiments, the term "heterocyclic" refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

In general, the term "aromatic moiety", as used herein, refers to stable substituted or unsubstituted unsaturated mono- or poly-cyclic hydrocarbon moieties having preferably 3-14 carbon atoms, comprising at least one ring satisfying the Huckel rule for aromaticity. Examples of aromatic moieties include, but are not limited to, phenyl, indanyl, indenyl, naphthyl, phenanthryl, and anthracyl.

In general, the term "heteroaromatic moiety", as used herein, refers to stable substituted or unsubstituted unsaturated mono-heterocyclic or polyheterocyclic moieties having preferably 3-14 carbon atoms, comprising at least one ring satisfying the Huckel rule for aromaticity. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety to provide moieties such as -(aliphatic)aromatic, -(heteroaliphatic)aromatic, -(aliphatic)heteroaromatic, -(heteroaliphatic)heteroaromatic, -(alkyl)aromatic, -(heteroalkyl)aromatic, -(alkyl)heteroaromatic, and -(heteroalkyl)heteroaromatic moieties. Substituents of these moieties include, but are not limited to, any of the previously mentioned substituents resulting in the formation of a stable compound.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic moieties, as described above, excluding those attached via an aliphatic (e.g., alkyl) or heteroaliphatic (e.g., heteroalkyl) moiety. In certain embodiments of the present invention, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Substituents for aryl and heteroaryl moieties include, but are not limited to, any of the previously mentioned substitutents, i.e., the substituents recited for aliphatic moieties, or for other moieties as disclosed herein, resulting in the formation of a stable compound.

The terms "alkoxy" (or "alkyloxy"), and "thioalkyl" as used herein refers to an alkyl group, as previously defined, attached to the parent molecular moiety through an oxygen atom ("alkoxy") or through a sulfur atom ("thioalkyl"). In certain embodiments, the alkyl group contains about 1-20 aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy groups, include but are not limited to, methoxy, ethoxy, propoxy, isopropoxy, n-butoxy, tert-butoxy, neopentoxy and n-hexoxy. Examples of thioalkyl groups include, but are not limited to, methylthio, ethylthio, propylthio, isopropylthio, n-butylthio, and the like.

The term "amine" refers to a group having the structure —N(R)$_2$ wherein each occurrence of R is independently hydrogen, or an aliphatic, heteroaliphatic, aromatic, heteroaromatic, -(alkyl)aromatic, -(heteroalkyl)aromatic, -(heteroalkyl)heteroaromatic, or -(heteroalkyl)heteroaromatic moiety, or the R groups, taken together with the nitrogen to which they are attached, may form a heterocyclic moiety.

The term "alkylamino" refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains about 1-20 aliphatic carbon atoms. In certain other embodiments, the alkyl group contains about 1-10 aliphatic carbon atoms. In yet other embodiments, the alkyl, alkenyl, and alkynyl groups employed in the invention contain about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkylamino include, but are not limited to, methylamino, ethylamino, isopropylamino and the like.

The terms "halo" and "halogen" as used herein refer to an atom selected from fluorine, chlorine, bromine and iodine.

The term "halogenated" denotes a moiety having one, two, or three halogen atoms attached thereto.

The term "haloalkyl" denotes an alkyl group, as defined above, having one, two, or three halogen atoms attached thereto and is exemplified by such groups as chloromethyl, bromoethyl, trifluoromethyl, and the like.

The term "acyloxy", as used herein, does not substantially differ from the common meaning of this term in the art, and refers to a moiety of structure —OC(O)R$_X$, wherein R$_X$ is a substituted or unsubstituted aliphatic, alicyclic, heteroaliphatic, heteroalicyclic, aryl or heteroaryl moiety.

The term "acyl", as used herein, does not substantially differ from the common meaning of this term in the art, and refers to a moiety of structure —C(O)R$_X$, wherein R$_X$ is a substituted or unsubstituted, aliphatic, alicyclic, heteroaliphatic, heteroalicyclic, aryl or heteroaryl moiety.

The term "imino", as used herein, does not substantially differ from the common meaning of this term in the art, and refers to a moiety of structure —C(=NR$_X$)R$_Y$, wherein R$_X$ is hydrogen or an optionally substituted aliphatic, alicyclic, heteroaliphatic, heteroalicyclic, aryl or heteroaryl moiety; and R$_Y$ is an optionally substituted aliphatic, alicyclic, heteroaliphatic, heteroalicyclic, aryl or heteroaryl moiety.

The term "C$_{1-6}$alkylene", as used herein, refers to a substituted or unsubstituted, linear or branched saturated divalent radical consisting solely of carbon and hydrogen atoms, having from one to six carbon atoms, having a free valence "-" at both ends of the radical.

The term "C$_{2-6}$alkenylene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl", and the like, used alone or as part of a larger moiety, encompass both substituted and unsubstituted groups.

In other embodiments, each member of the library of test fragments has a structure selected from the group consisting of:

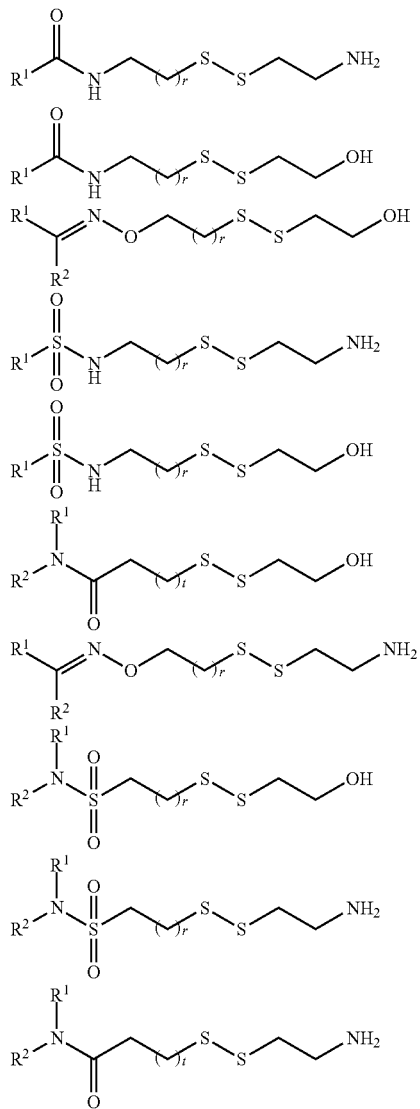

-continued

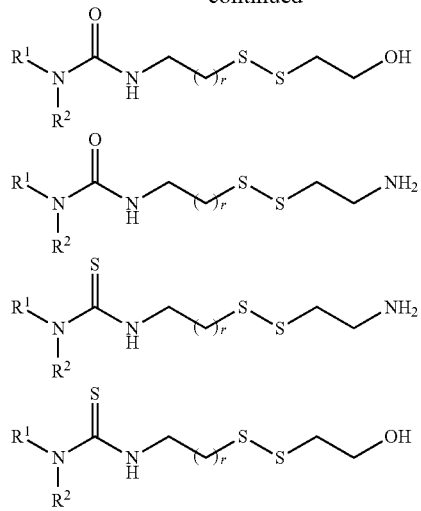

wherein r is 1 or 2; each occurrence of $R^1$ and $R^2$ is independently hydrogen, or an aliphatic, heteroaliphatic, aryl, heteroaryl, -(aliphatic)aryl, -(aliphatic)heteroaryl, -(heteroaliphatic)aryl, or -(heteroaliphatic)heteroaryl moiety, or wherein $R^1$ and $R^2$ taken together are a cycloaliphatic, heterocycloaliphatic, aryl or heteroaryl moiety wherein each of the foregoing aliphatic and heteroaliphatic moieties is substituted or unsubstituted, linear or branched and each of the foregoing cycloaliphatic, heterocycloaliphatic, aryl or heteroaryl moieties is independently substituted or unsubstituted; and t is 0, 1, or 2.

In other embodiments, each member of the library of test fragments has a structure of the formula $$L\text{-}(CH_2)_n\text{-}S\text{-}D,$$

wherein L is an aliphatic, heteroaliphatic, aryl or heteroaryl moiety; n is 0-5 (optionally 0-2); D is —$S(CH_2)_pR^{41}$, wherein p is 1-5, $R^{41}$ is —$NR^{43}R^{44}$; $OR^{43}$; $SR^{43}$; —$NHCOR^{43}$; —$NHCONR^{43}R^{44}$; —$NR^{43}R^{44}R^{45+}$ $X^-$, wherein X is a halogen; —$COOR^{43}$; $CONR^{43}R^{44}$; —$SO_3R^{43}$; —$OPO_3R^{43}$; —$SO_2R^{43}$; and each occurrence of $R^{43}$, $R^{44}$, and $R^{45}$ is independently hydrogen, a protecting group, or an aliphatic, heteroaliphatic, aryl, or heteroaryl moiety;

wherein each of the foregoing aliphatic and heteroaliphatic moieties is substituted or unsubstituted, linear or branched and each of the foregoing cycloaliphatic, heterocycloaliphatic, aryl or heteroaryl moieties is independently substituted or unsubstituted.

In other embodiments, each member of the library of test fragments has a structure of the formula $$L\text{-}(CH_2)_n\text{-}S\text{-}D,$$

wherein L is an aliphatic, heteroaliphatic, aryl or heteroaryl moiety; n is 0-5 (optionally 0-2); D is —$S(CH_2)_2NH_2$ or —$S(CH_2)_2OH$;

wherein each of the foregoing aliphatic and heteroaliphatic moieties is substituted or unsubstituted, linear or branched and each of the foregoing cycloaliphatic, heterocycloaliphatic, aryl or heteroaryl moieties is independently substituted or unsubstituted.

Disulfide libraries of test fragments may be reacted as exchangeable disulfides with thiols or protected thiols to produce libraries of test ligands where z comprises a disulfide.

In other embodiments, z comprises a thioether group. The thioether is formed from reaction of chemically reactive groups x and y. The thioether may be prepared by reaction of a thiol with an aryl, heteroaryl or alkyl group substituted with a leaving group, where the leaving group may be a halide or a sulfonate group (—OSO$_2$R where R is substituted or unsubstituted alkyl or aryl, e.g., CH$_3$, CF$_3$, phenyl-CH$_3$ and phenyl-NO$_2$). The halide could be attached to an aromatic or heteroaromatic functionality, or it could be attached to an aliphatic group on the bait or the library members. When the leaving group is a substituent of aromatic and heteroaromatic functionalities, an S$_N$Ar reaction or a palladium-mediated, copper-mediated, or related transition metal-mediated coupling reaction would be performed. Where the leaving group is a substituent of alkyl functionalities, an S$_N$2 or S$_N$1 reaction would be performed. These methods are known to those practiced in the art. March et al., supra, pp. 407-409 and Peach in Patai, *The Chemistry of the Thiol Group*, pt. 1, John Wiley & Sons, New York, 1974, pp. 721-735. The thioether may also be prepared by the Mitsunobu reaction between alcohols and thiols. See, e.g., (Hughes et al. (Paquette, Series Editor in Chief), *Organic Reactions*, John Wiley & Sons, New York, 1992, vol. 42, pp. 335-636. The thioether groups may also be prepared by reaction of a thiol with a Michael Acceptor such as an acrylamide, an acrylate, or a vinyl sulfone moiety.

The thioether groups in the linkers may also be oxidized to more water-soluble sulfoxides and sulfones (March et al., supra, pp. 1201 1203).

In another embodiment, z comprises a disulfide. The disulfides may be prepared by reacting the thiols with thiols (—SH), activated thiols such as —SSH, —S(halo), or —SSO$_2$—R where R is, for example, an alkyl or aryl group, employing known methods to those practiced in the art (e.g., Greene et al., "Protective Groups" in *Organic Synthesis*, John Wiley & Sons, New York, 2$^{nd}$ edition, 1991, pp. 302 303). The thiols or activated thiols may be straight chain or branched alkyls optionally with heteroatoms in the chain, or may be optionally substituted aryl or heteroaryl groups. Alternatively, disulfide test ligands can be formed though disulfide exchange between thiols and disulfides under reducing conditions.

By "structurally related analog", "analog" and the like, of a given fragment is meant a fragment that has substantially the same chemical structure as a given fragment except that the analog has a different chemically reactive functionality than does the given fragment. The analog of the fragment may also optionally possess or lack one or more substituents that are either lacking or present, respectively, on the fragments identified provided that the presence or absence of those substituents does not substantially alter the compounds ability to bind to the target. An analog may differ from a reference compound by replacement of one atom by an atom of a different element or replacement of one functional group by another. A library of, for example, test disulfide fragments can be reacted with a suitable bait fragment to identify the test ligands that bind to the target biological molecule. Alternatively, one can chemically couple, for example, test aldehydes having the same chemical structures as the disulfides (but which have an aldehyde reactive functionality rather than a disulfide reactive functionality). In general, it is not critical to the invention whether a given reactive group is present on the bait or on the test library members. For example, a screening experiment where the bait has the structure B-x and the first test fragment has the structure y-T$_1$, where x is a thiol and y is a disulfide, could alternatively be performed using a bait where x is a disulfide and test ligands where y is a thiol.

For resynthesis of the ligands identified in screens, therefore, it is contemplated that the chemical coupling not only use the same chemistry used in the screen, but also the chemical coupling of structurally related analogs of those compounds (e.g., disulfides are used in the screen, but the analogous aldehydes are linked in the resynthesized ligand).

As used herein, "linker" means N, O, S, —S—S—, or a 2-10 atom heteroaliphatic linker having at least one N, O, or S atom in the backbone, and may be denoted "z". The structure of the linker z will be the product of the reaction of the reactive functionalities x and y. In certain embodiments the linker z comprises a disulfide or thioether moiety. As used herein "disulfide" refers to a —S—S— group linking the bait moiety to a test moiety in a test ligand or a —C—S—S—C— group, in which neither of the carbons is double bonded to an oxygen. As used herein, "thioether" means a —S— group linking the bait moiety to a test moiety in a test ligand, or a —C—S—C— group, in which neither of the carbons is double bonded to an oxygen.

As used herein a "test ligand" is a molecule comprising a bait moiety B attached via a linker z to a test moiety T. In contrast to "ligands" per se, the affinity of a test ligand for a target need not be determinate prior to being employed in a method of the invention. Conversely, the method of the invention can be employed, in certain embodiments, to determine whether a test ligand has measurable affinity for the target, i.e., to determine whether the test ligand is in fact a ligand per se for the target.

As used herein "test ligand:target complex" means a complex formed upon contacting a target with a test ligand. In one embodiment, the contacting occurs between a target and a purified test ligand. In another embodiment, the contacting occurs between a target and multiple test ligands. In yet another embodiment, the contacting occurs between a target and an unpurified reaction mixture yielding a test ligand. Similarly, as used herein "test ligand:protein complex" means a complex formed upon contacting a target protein with a test ligand.

As used herein "measurable" in reference to binding affinity or other affinity parameter means that a value for the affinity parameter is reliably detectable for a ligand of the target. The skilled person will understand that different affinity parameters may be measured with different degrees of precision and accuracy. Ideally, the, precision, accuracy, and dynamic range of an assay will easily accommodate a range of values, so that ligands exhibiting a wide range of measured values for the affinity parameter can be studied. The skilled person will often establish thresholds against which a given test result may be said to be meaningful. For example, in an assay of enzyme inhibition, the concentration of a putative inhibitor of the enzyme may be required to be below a preselected concentration to be considered to be meaningful. To illustrate, an IC$_{50}$ threshold may be established for a biochemical assay of a target protein. A bait moiety may be preselected that does not itself meet the threshold, but which shows a weaker IC$_{50}$. Then, pursuant to a screening procedure according to the invention, one or more test ligands may be assessed as being more potent and meeting the IC$_{50}$ threshold. In other cases, a degree of improvement in potency over that of the bait moiety, e.g., a 10-fold improvement, may be the threshold chosen for the assessment.

The term "monophore" as used herein means a monomeric unit of a test ligand. The term "diaphore" denotes two monophores covalently linked to form a unit, i.e., a test ligand, that, ideally, has a higher affinity for the target insofar as the two constituent monophores bind to two separate but nearby sites on the target. The binding affinity of a diaphore (test ligand), which is a product of the affinities of the individual monophores, may be referred to as "avidity." The term "diaphore" is used irrespective of whether the unit is covalently bound to the target or exists separately after its release from the target.

"Small molecules" are usually about 2,000 Da molecular weight or less, and include but are not limited to synthetic organic or inorganic compounds, peptides, (poly)nucleotides, (oligo)saccharides and the like. Small molecules specifically include inter alia small non-polymeric (e.g., not peptide or polypeptide) organic and inorganic molecules. Many pharmaceutical companies have extensive libraries of such molecules, which can be conveniently used in the methods of the invention. In one embodiment, small molecules have molecular weights of up to about 1,000 Da. In another embodiment small molecules have molecular weights of less than about 650 Da. In one embodiment, small molecules have molecular weights of up to about 300 Da. Included within this definition are small organic (including non-polymeric) molecules containing metals such as Zn, Hg, Fe, Cd, and As which may form a bond with nucleophiles.

A "site" on a target refers to a site to which a specific ligand binds, which may include a specific sequence of monomeric subunits, e.g., amino acid residues, or nucleotides, and may have a characterized three-dimensional structure. Typically, the molecular interactions between the ligand and the site of interest on the target are non-covalent, and include hydrogen bonds, van der Waals interactions and electrostatic interactions. In the case of polypeptides a site of interest broadly includes the amino acid residues involved in binding of the target to a molecule with which it forms a natural complex in vivo or in vitro.

When, for example, the target is a protein that exerts its biological effect through binding to another protein, such as with hormones, cytokines or other proteins involved in signaling, it may form a natural complex in vivo with one or more other proteins. In this case, the site of interest is defined as the critical contact residues involved in a particular protein:protein binding interface. Critical contact residues are defined as those amino acids on a first protein that make direct contact with amino acids on a second protein, and when mutated to alanine decrease the binding affinity by at least 10-fold, alternately at least 20-fold, as measured with a direct binding or competition assay (e.g. ELISA or RIA). See Clackston et al., "A Hot Spot of Binding Energy in a Hormone-Receptor Interface" *Science* 267:383-386 (1995) and Cunningham and Wells, *J. Mol. Biol.,* 234:554-563 (1993)). Also included in the definition of a site of interest are amino acid residues from the second protein B that are within about 4 angstroms of any of the atoms of the critical contact residues identified in the first protein A.

The term "antagonist" is used in the broadest sense and includes any ligand that partially or fully blocks, inhibits or neutralizes a biological activity exhibited by a target.

The term "agonist" is used in the broadest sense and includes any ligand that mimics a biological activity exhibited by a target, such as a target, for example, by specifically changing the function or expression of such target, or the efficiency of signaling through such target, thereby altering (increasing or inhibiting) an already existing biological activity or triggering a new biological activity.

The phrase "adjusting the conditions" as used herein means subjecting a target to any individual, combination, or series of reaction conditions or reagents necessary to cause a covalent bond to form between the ligand and the target, or to break a covalent bond already formed.

"Active" or "activity" means a measurable, quantitative biological and/or immunological property. Examples of biological activities for protein targets include protein-protein binding and catalytic activity of enzymes.

"Derivative" as used herein means a compound obtained from another compound (i.e., a "parent" compound) and containing essential elements of the parent compound, or is a compound related structurally to such parent compound. "Derivative" encompasses compounds that may be obtained directly from the parent compound, or that may be obtained from a common intermediate thereto using analogous chemical methods. For example, adenine is a derivative of purine.

"Mimetic" as used herein means a compound that mimics one or more key interactions of another compound with a target, including such features as hydrogen bond donor/acceptor status, van der Waals interactions, electrostatic interactions, and/or steric properties. One example of a mimetic is a peptidomimetic, which is a compound that mimics a peptide, but that has amide bonds replaced with non-amide bonds. Another example of a mimetic is a "purine mimetic", which as used herein means a compound whose structure complements the planar aromatic structure and hydrogen bonding functionality of adenine with a kinase or other purine-binding target. For example a purine mimetic may mimic the hydrogen bond forming capacity of the N1 nitrogen of adenine. Preferably, a purine mimetic complements the dual hydrogen bond donor-acceptor properties of adenine. For example, diaminopyrimidine (DAP) and aminoquinazoline are purine mimetics.

"Isostere" as used herein means a compound that has the same number of valence electrons in the same configuration as another compound but that differs from the latter in the kinds and/or numbers of atoms. For example, isosteres of amide (—CO—NH—) groups include hydroxyethylamine (—CHOH—CH$_2$NH—), hydroxyethylene (—CHOH—CH$_2$—), dihydroxyethylene (—CHOH—CHOH—), and the like.

"Selectively binds" as used herein in the context of a ligand, e.g., a test ligand, binding to a target (e.g., a protein) means that the dissociation constant of the ligand for the target is at least 10-fold lower than the dissociation constant of the ligand for another biological molecule(s) being used as a reference. For example, if a ligand "selectively binds" Aurora-A over Aurora-B, it binds Aurora-A with at least a 10-fold lower dissociation constant than its corresponding dissociation constant for Aurora-B.

"Selectively modulates" as used herein in the context of a moleculemodulating a given functional or structural property of a target (e.g., a protein), means that themolecule measurably alters that property, either positively or negatively, to a greater degree than the modulation of the property by a ligand of another biological molecule(s) being used as a reference.

The present invention relates generally to methods of identifying compounds that exhibit enhanced properties associated with their binding affinity for a protein or other target. The methods also provide a means of rapidly assessing target tractability, e.g., by determining the number of hits per number of compounds screened ("hit rate"). The screening procedures used in the method employ libraries of test ligands in which each test ligand in the library comprises a preselected chemical moiety that is common to all of the test ligands in the library, but each test ligand also comprises a unique chemical moiety that distinguishes it from the other test ligands in the library. To illustrate one advantage of an embodiment of the invention, such screening procedures may be used to leverage an affinity of the preselected moiety for a target to rapidly screen and identify derivative compounds that provide enhanced affinity for the target. Other and further advantages will become apparent in the following description of methods of the invention.

The fragment based technology of the invention combines the advantages of fragment based approaches with the power and speed of high throughput screening (HTS). The technology is based on a functional screen of target-directed "made-to-order" libraries of test ligands, i.e., the libraries are constructed based on target specific information. Test ligands within such libraries are constructed between a target-directed fragment (the "bait" fragment) and a library of naive test fragments. The assembly process can be fully automated with low reagent cost and no need for purification of the assembled fragments.

A screening campaign (i.e., one or more screening procedures) can involve multiple bait fragments, which can be derived from a number of sources. For example, a bait fragment can be derived from a preferred pharmacophore/fragment from an existing drug or literature compound. Alternatively, the bait fragment can be derived from an existing lead compound, such as a lead compound identified by any conventional medicinal chemistry program. A bait fragment can be derived from a natural substrate or ligand, or derived from a compound identified in a screen of a naïve fragment library. In an iterative embodiment contemplated under the invention, a bait fragment can be a fragment identified as a hit during an initial or a prior screening procedure according to the invention. This concept may be referred to as activity-based chemotype evolution.

The fragment-based screening technology of the invention provides several advantages over other fragment based approaches. For example, the method of the invention enables rapid survey of relevant chemical space through an iterative fragment assembly approach. The method of the invention is applicable to development of ligands for a variety of targets, including large proteins, protein complexes, and partially purified fractions. Another advantage of the method of the invention is that the three-dimensional structure of the target need not be characterized. Another advantage of the present invention is that it can be configured to provide a direct readout of inhibition of the activity of a protein or other target by the test ligands. Another advantage is that the method provides high sensitivity with low protein consumption. Relatedly, the method enables use commercial protein sources, which can provide substantial savings in time and cost over methods that require manufacture of variants, truncates, and modified versions of targets of interest.

Yet another advantage of the invention is that the fragment assembly reaction can take place in absence of target receptor and can, therefore, be conducted under denaturing conditions. This is in contrast to dynamic combinatorial chemistry methods, where fragments are assembled in presence of receptor ligand and, therefore, must occur under conditions that preserve receptor integrity. Conducting fragment assembly under denaturing conditions according to the invention allows the use of a multitude of different chemistries and presents new opportunities for introducing chemical diversity.

In certain embodiments, the screening method of the present invention employs a library comprising a plurality of test ligands, each comprising a preselected bait moiety linked to one of a plurality of test moieties. For example, a bait moiety, B, can be linked to a library of n test moieties $(T_1, T_2, \ldots T_n)$ to provide n different test ligands ($B$-$z$-$T_1$, $B$-$z$-$T_2$, ... $B$-$z$-$T_n$), in which z is a linker that links the bait moiety to each of the test moieties.

The bait moiety B is preselected as a reference point for evolving test ligands. That is, the bait moiety is not assigned uncritically or randomly, but is deliberately selected beforehand on the basis of having some property that is deemed to be potentially associated with interacting usefully with the target of interest. For example, the bait moiety may be derived from a previously identified ligand of the target. Thus, a substructure of the prior ligand may be used as the bait moiety in the methods of the invention. It is not necessary that the bait moiety have any intrinsic selective affinity for the target, but it may be desirable in certain circumstances that the bait moiety have some such selective affinity. Typically, such affinity of the bait moiety for the target, if any, will be low, e.g., a binding affinity of between about 10 μM and about 100 mM.

Alternatively, the bait moiety may have no intrinsic binding affinity for the target, but may be identified as a relevant or important substructure among a family of ligands, without which the ligands lose substantial affinity for the target.

Alternatively, the bait moiety may be selected on the basis of theoretical considerations derived from previous analysis of structure-activity relationships (SAR) of ligands of the target. For example, crystallographic study of co-crystals of ligands and the target, or methods known as "SAR by NMR," and the like, may yield insights into moieties that may be suitable for use in the present methods as bait moieties.

In some embodiments, the bait moiety B is preselected with reference to an "affinity parameter," i.e., a functional parameter associated with or dependent upon binding between the target protein and a ligand thereof. For example, the affinity parameter may be selected from the group consisting of a biological activity of the protein, a conformational state of the protein, a state of the protein dependent upon regulatory modification, e.g., activation or inactivation via phosphorylation, displacement of a known ligand of the protein, a dissociation constant of a ligand for the protein, an affinity constant of a ligand for the protein; a melting temperature of the protein; and a denaturing temperature for the protein, and the like.

In embodiments of the invention that comprise assessing the presence or absence of binding of at least one test ligand to the protein or other target, such assessment can be accomplished through measuring an affinity parameter dependent upon binding between the protein and a ligand thereof. Affinity parameters suitable for assessment in the methods of the invention may be selected from those of interest to the skilled practitioner or otherwise known in the art. For example, affinity parameters suitable for use in assessing binding of test ligands to proteins or other targets including, without limitation, a biological activity of the target, a conformational state of the target, a dissociation constant of a ligand for the target, an affinity constant of a ligand for the target; a melting temperature of the target; a denaturing temperature for the target, a change in chemical shift for the ligand and/or the target, spin polarization transfers (nuclear Overhauser effects (NOEs)).

In embodiments of the invention that comprise steps of identifying a test ligand, the skilled practitioner may identify suitable proprietary methods or methods otherwise known in the art for identifying a ligand of a protein or other target. The identification methods may comprise identifying a test ligand for which a value of an affinity parameter is superior to the value of the affinity parameter of the bait moiety, the bait fragment, or a structural analog thereof. Alternatively, the identifying step can comprise identifying a test ligand for which a value of an affinity parameter is superior to the value of the affinity parameter measured for a composition comprising the bait moiety and the test moiety of the test ligand being identified.

For example, an enzyme will have a characteristic rate of reaction for a substrate, and this parameter may be modulated by a non-substrate ligand that binds to the active site of the enzyme. In such a case, the parameter being assessed may be the concentration that inhibits maximal activity of the enzyme by 50%, the so-called "$IC_{50}$." This can be done in a biochemical assay, in which test ligands are contacted with isolated enzyme. Alternatively, such assays can be done using cell membranes that present the enzyme, or in intact cells that natively or recombinantly express the enzyme, and in which the activity of the enzyme can be measured. Numerous methods are known in the art for assessing the capacity of a putative ligand to interfere with enzyme activity, and the skilled person will be able to adapt such methods for use in the methods of the invention.

The bait moiety may be assessed for preselection on the basis of one or more such affinity parameters. A single or several bait moieties may be selected from a plurality of potential bait moieties by performing a pre-screen of the moieties and then selecting a moiety or moieties having superior measured values for the affinity parameter.

In some embodiments, the preselected bait moiety: (a) selectively binds the protein; (b) selectively modulates a functional or structural property of the protein; (c) comprises a portion of a compound that selectively binds the protein; or (d) is a derivative/analog/isostere of a compound that selectively binds the protein.

In one aspect, the invention comprises methods for screening for a compound that binds to a target, which methods comprise performing a screening procedure comprising:
  (a) reacting a bait fragment B-x, comprising a preselected bait moiety B and a reactive functionality x, with a plurality of test fragments (y-$T_1$, y-$T_2$, . . . y-$T_n$), each test fragment comprising a reactive functionality y and one of a plurality of test moieties ($T_1$, $T_2$, . . . $T_n$) under conditions that provide a plurality of n test ligands (B-z-$T_1$, B-z-$T_2$, . . . B-z-$T_n$), wherein z is a linker formed by reaction of x and y;
  (b) contacting the target with one or more of the test ligands under conditions that permit binding between the target and a ligand thereof, wherein binding between the target and at least one of the test ligands forms at least one test ligand:target complex; and
  (c) assessing the presence or absence of binding of at least one of the test ligands to the target.

In any embodiment in which a bait moiety is reacted with a library of test fragments, it is possible that the resultant collection of test ligands may not contain ligands representative of all of the test fragments. That is, if a bait fragment is reacted with n test fragments, the collection of test ligands may contain m test ligands, where m is equal to or less than n. Thus, in another aspect, the invention comprises methods for screening for a compound that binds to a target, which methods comprise performing a screening procedure comprising:
  (a) reacting a bait fragment B-x, comprising a preselected bait moiety B and a reactive functionality x, with a plurality of n test fragments (y-$T_1$, y-$T_2$, . . . y-$T_n$), each test fragment comprising a reactive functionality y and one of a plurality of n test moieties ($T_1$, $T_2$, . . . $T_n$) under conditions that provide a plurality of m test ligands (B-z-$T_1$, B-z-$T_2$, . . . B-z-$T_m$), wherein z is a linker formed by reaction of x and y, and m is less than or equal to n;
  (b) contacting the target with one or more of the test ligands under conditions that permit binding between the target and a ligand thereof, wherein binding between the target and at least one of the test ligands forms at least one test ligand:target complex; and
  (c) assessing the presence or absence of binding of at least one of the test ligands to the target.

In some embodiments, m is at least about 50% of n. In some embodiments, m is at least about 60% of n. In some embodiments, m is at least about 70% of n. In some embodiments, m is at least about 80% of n. In some embodiments, m is at least about 90% of n.

In some embodiments, the target is a protein. In some embodiments, the preselected bait moiety B binds the target; modulates a functional or structural property of the target; comprises a portion of a compound that binds the target; or is a derivative, analog, or isostere of a compound that binds the target.

In some embodiments, the preselected bait moiety selectively binds the target; selectively modulates a functional or structural property of the target; comprises a portion of a compound that selectively binds the target; or is a derivative, analog, or isostere of a compound that selectively binds the target.

In another aspect, the invention comprises methods for screening for a compound that binds to a protein. The method comprises performing a screening procedure comprising:
  (a) reacting a bait fragment B-x, comprising a preselected bait moiety B and a reactive functionality x, with a plurality of test fragments (y-$T_1$, y-$T_2$, . . . y-$T_n$), each test fragment comprising a reactive functionality y and one of a plurality of test moieties ($T_1$, $T_2$, . . . $T_n$) under conditions sufficient to provide a plurality of n test ligands (B-z-$T_1$, B-z-$T_2$, . . . B-z-$T_n$), wherein z is a linker formed by reaction of x and y;
  (b) contacting the protein with one or more of the test ligands under conditions that permit binding between the protein and a ligand thereof, wherein binding between the protein and at least one of the test ligands forms at least one test ligand:protein complex;
  (c) assessing the presence or absence of binding of at least one of the test ligands to the protein; and
  (d) identifying at least one test ligand that binds to the protein.

In some embodiments of the invention, once a screening procedure has been performed, at least one subsequent screening procedure may be performed. In such cases, the reacting step of a subsequent screening procedure employs a plurality of test fragments (y-$T_1$, y-$T_2$, . . . y-$T_n$) that is identical to the plurality of test fragments employed in the reacting step of a prior screening procedure. Alternatively, the method can comprise at least one subsequent screening procedure wherein the reacting step of a subsequent screening procedure employs a plurality of test fragments (y-$T_1$, y-$T_2$, . . . y-$T_n$) that is different from the plurality of test fragments employed in the reacting step of a prior screening procedure.

In another embodiment, the invention comprises methods for screening for a compound that binds to a protein. The method comprises performing a first screening procedure comprising:

(a) reacting a bait fragment B-x, comprising a preselected bait moiety B and a reactive functionality x, with a plurality of test fragments (y-$T_1$, y-$T_2$, ... y-$T_n$), each test fragment comprising a reactive functionality y and one of a plurality of test moieties ($T_1$, $T_2$, ... $T_n$) under conditions sufficient to provide a plurality of n test ligands (B-z-$T_1$, B-z-$T_2$, ... B-z-$T_n$), wherein z is a linker formed by reaction of x and y;

(b) contacting the protein with one or more of the test ligands under conditions that permit binding between the protein and a ligand thereof, wherein binding between the protein and at least one of the test ligands forms at least one test ligand:protein complex;

(c) assessing the presence or absence of binding of at least one of the test ligands to the protein; and (d) identifying at least one test ligand that binds to the protein;

and a second screening procedure; comprising the steps of:

(a') providing a plurality of test ligands (B'-z-$T'_1$, B'-z-$T'_2$, ... B'-z-$T'_n$), each comprising a bait moiety B' attached via a linker z to one of a plurality of test moieties ($T'_1$, $T'_2$, ... $T'_n$); wherein the bait moiety B' comprises the test moiety of a test ligand identified in step (d);

(b') contacting the protein with the plurality of test ligands provided in step (a') under conditions that permit binding between the protein and a ligand thereof;

(c') assessing the presence or absence of binding between a test ligand and the protein; and (d') identifying a test ligand that binds to the protein in step (c').

The bait moiety B used in the methods of the invention typically has a molecular mass of up to about 5,000 Da. For example, the bait moiety can be an amino acid, or a small peptide comprising from 2 to 10, from 2 to 8, or from 2 to 6 amino acid residues. Peptide or peptidomimetic bait moieties can comprise natural amino acid residues or artificial amino acid residues or both. The amino acid residues in such peptides may be L-amino acids, D-amino acids, or combinations thereof. In some cases, it may be desirable to replace one or more amino acid residues in the bait moiety with other small organic components. Other, non-peptidyl bait moieties having molecular mass of up to about 5,000 Da are contemplated under the invention. For example, in certain embodiments, the bait is a purine mimetic.

In some embodiments, the bait moiety B has a mass of up to about 500 Da. In some embodiments the bait moiety has a mass of up to about 450 Da, up to about 400 Da, up to about 350 Da, up to about 300 Da, up to about 250 Da, up to about 200 Da, or up to about 150 Da. In other embodiments, the bait moiety B has a mass of from about 150 Da to about 350 Da.

In some embodiments, the bait fragment B-x has a mass of up to about 600 Da. In some embodiments the bait fragment has a mass of up to about 450 Da, up to about 400 Da, up to about 350 Da, up to about 300 Da, up to about 250 Da, or up to about 200 Da. In other embodiments, the bait fragment has a mass of from about 250 Da to about 500 Da. In other embodiments, the bait fragment has a mass from about 300 Da to about 400 Da.

In some embodiments, each test moiety ($T_1$, $T_2$, ... $T_n$) has a mass of up to about 500 Da. In some embodiments each test moiety has a mass of up to about 450 Da, up to about 400 Da, up to about 350 Da, up to about 300 Da, up to about 250 Da, or up to about 200 Da. In other embodiments each test moiety has a mass of from about 150 Da to about 400 Da.

In some embodiments, each test ligand (B-z-$T_1$, B-z-$T_2$, ... B-z-$T_n$) has a mass of up to about 1,000 Da. In some embodiments each test ligand has a mass of up to about 600 Da, up to about 550, up to about 500, up to about 450 Da, up to about 400 Da, up to about 350 Da, up to about 300 Da, up to about 250 Da, or up to about 200 Da. In other embodiments, each test ligand has a mass of between about 350 Da to about 600 Da, between about 375 Da and about 500 Da, or between about 375 Da and about 450 Da.

In some embodiments, it may be useful to design the library of naïve test fragments (y-T1, y-T2, ... y-Tn) so that each of the test fragments has a different mass. In such a case, the resulting test ligands (B-z-T1, B-z-T2, ... B-z-Tn) will each have a different mass. In some embodiments, the masses of the test ligands (B-z-T1, B-z-T2, ... B-z-Tn) differ from each other by at least 0.1 Da. Such differences can assist in methods such as mass spectrometry that rely on molecular mass to assist in identification of unknown moieties.

In some embodiments of the invention, each of the test ligands in the library of test ligands is contacted with the protein separately. In other embodiments, the protein is contacted with two or more of the test ligands. In other embodiments, the protein is contacted with pools comprising from two to about 20, or from 2 to about 10, test ligands. In some embodiments, a mixture comprising 100 or more of the test ligands may be contacted with the protein.

In some embodiments, the methods of the invention employ libraries comprising large numbers of test fragments (y-$T_1$, y-$T_2$, ... y-$T_n$), e.g., comprising from 2 to about 100,000 or more test fragments (where n is an integer). Large numbers of test fragments require automation to be practicable in reasonable times. However, in embodiments of the invention, the number of test ligands can be from 2 to about 25,000, from 2 to about 10,000, from 2 to about 10,000, from 2 to about 5,000, from 2 to about 2,500, from 2 to about 1,000, from 2 to about 500, or from 2 to about 250. Smaller numbers of test fragments can make the methods of the invention practicable using hand pipeting and smaller scale equipment with little or no mechanical automation for preparation of reaction mixtures. In such cases, the libraries of test ligands (B-z-$T_1$, B-z-$T_2$, ... B-z-$T_n$) are of similar magnitude. To illustrate, a library comprising about 1,000 test fragments can yield a library of about 1,000 test ligands, depending on the efficiencies of reaction between the test fragments and the bait fragment being employed.

Assays suitable for large-scale screening of binding or activity of targets are known in the art. These methods may be employed in the present invention to assess the presence or absence of binding of the test ligands to the target. For large libraries (e.g. those having 100 or more test ligands), assays amenable to automation are preferred. Such assays include but are not limited to fluorescence polarization (FP) assays, such as IMAP; homogeneous time-resolved fluorescence (HTRF) assays; time resolved fluorescence resonance energy transfer (TR-FRET) assays such as LanthaScreen; and ELISA. Other methods that can be employed in the present invention include High Content Screening (HCS) methods, cell cycle analysis methods, and substrate phosphorylation methods. Mass spectrometric (MS) analysis of isolated target-ligand complexes may also be employed, for example, in instances requiring identification of compounds that bind to and stabilize inactive states or conformations of an enzyme. Identification can be performed by measuring the mass of the target-test ligand complex, or by releasing the test ligand from the complex.

In another aspect, the invention comprises methods for screening for a compound that binds to a protein. The method comprises performing a screening procedure comprising:

(a) reacting a bait fragment B-x, comprising a preselected bait moiety B and a reactive functionality x, with a plurality of test fragments (y-$T_1$, y-$T_2$, . . . y-$T_n$), each test fragment comprising a reactive functionality y and one of a plurality of test moieties ($T_1$, $T_2$, . . . $T_n$) under conditions sufficient to provide a plurality of n test ligands (B-z-$T_1$, B-z-$T_2$, . . . B-z-$T_n$), wherein z is a linker formed by reaction of x and y;

(b) contacting the protein with one or more of the test ligands under conditions that permit binding between the protein and a ligand thereof, wherein binding between the protein and at least one of the test ligands forms at least one test ligand:protein complex;

(c) isolating at least one test ligand:protein complex formed in step (b) from test ligands that are not bound to the protein; and (d) identifying the test ligand of at least one isolated test ligand:protein complex.

In another aspect, the invention comprises methods for screening for a compound that binds to a protein, comprising performing a screening procedure comprising:

(a) reacting a bait fragment B-x, comprising a preselected bait moiety B and a reactive functionality x, with a plurality of test fragments (y-$T_1$, y-$T_2$, . . . y-$T_n$), each test fragment comprising a reactive functionality y and one of a plurality of test moieties ($T_1$, $T_2$, . . . $T_n$) under conditions sufficient to provide a plurality of n test ligands (B-z-$T_1$, B-z-$T_2$, . . . B-z-$T_n$), wherein z is a linker formed by reaction of x and y;

(b) contacting the protein with one or more of the test ligands under conditions that permit binding between the protein and a ligand thereof, wherein binding between the protein and at least one of the test ligands forms at least one test ligand:protein complex;

(c) chromatographically isolating at least one test ligand:protein complex formed in step (b) from test ligands that are not bound to the protein; and (d) identifying the test ligand of at least one isolated test ligand:protein complex by mass spectrometric analysis of the test ligand:protein complex. The chromatographic isolation in step (c) above can be performed, for example, by gel permeation chromatography or by size exclusion chromatography.

In another aspect, the invention comprises methods for screening for a compound that binds to a protein. The method comprises performing a screening procedure comprising:

(a) reacting a bait fragment B-x, comprising a preselected bait moiety B and a reactive functionality x, with a plurality of test fragments (y-$T_1$, y-$T_2$, . . . y-$T_n$), each test fragment comprising a reactive functionality y and one of a plurality of test moieties ($T_1$, $T_2$, . . . $T_n$) under conditions sufficient to provide a plurality of n test ligands (B-z-$T_1$, B-z-$T_2$, . . . B-z-$T_n$), wherein z is a linker formed by reaction of x and y;

(b) contacting the protein with one or more of the test ligands under conditions that permit binding between the protein and a ligand thereof, wherein binding between the protein and at least one of the test ligands forms at least one test ligand:protein complex;

(c) assessing the presence or absence of binding of at least one of the test ligands to the protein;

(d) identifying at least one test ligand that binds to the protein;

(e) synthesizing a derivative test ligand comprising the bait moiety linked to the test moiety of the test ligand identified in step (d), wherein the bait moiety and the test moiety are linked through a linker z' that is the same as or is different from the linker z of the identified test ligand;

(f) contacting the protein with the derivative test ligand under conditions that permit binding of the protein with ligands thereto; and (g) assessing binding between the derivative test ligand and the protein by measuring the affinity parameter for the derivative test ligand.

In another embodiment, the invention comprises methods for screening for a compound that binds to a protein. The method comprises performing a first screening procedure comprising:

(a) reacting a bait fragment B-x, comprising a preselected bait moiety B and a reactive functionality x, with a plurality of test fragments (y-$T_1$, y-$T_2$, . . . y-$T_n$), each test fragment comprising a reactive functionality y and one of a plurality of test moieties ($T_1$, $T_2$, . . . $T_n$) under conditions sufficient to provide a plurality of n test ligands (B-z-$T_1$, B-z-$T_2$, . . . B-z-$T_n$), wherein z is a linker formed by reaction of x and y;

(b) contacting the protein with one or more of the test ligands under conditions that permit binding between the protein and a ligand thereof, wherein binding between the protein and at least one of the test ligands forms at least one test ligand:protein complex;

(c) assessing the presence or absence of binding of at least one of the test ligands to the protein; and (d) identifying at least one test ligand that binds to the protein;

and a second screening procedure; comprising the steps of:

(a') providing a plurality of test ligands (B'-z-T'1, B'-z-T'2, . . . B'-z-T'n), each comprising a bait moiety B' attached via a linker z to one of a plurality of test moieties (T'1, T'2, . . . T'n); wherein the bait moiety B' comprises the test moiety of a test ligand identified in step (d);

(b') contacting the protein with the plurality of test ligands provided in step (a') under conditions that permit binding between the protein and a ligand thereof;

(c') assessing the presence or absence of binding between a test ligand and the protein;

(d') identifying a test ligand that binds to the protein in step (c'); and

Subsequent to step (d) and or step (d') performing the steps of:

(e) synthesizing a derivative test ligand comprising the bait moiety (B or B') linked to the test moiety of the test ligand identified in step (d) or (d'), wherein the bait moiety and the test moiety are linked through a linker z' that is the same as or is different from the linker z of the identified test ligand;

(f) contacting the protein with the derivative test ligand under conditions that permit binding of the protein with ligands thereto; and (g) assessing binding between the derivative test ligand and the protein by measuring the affinity parameter for the derivative test ligand.

In embodiments where one wishes to confirm the activity of a test ligand identified in a screening procedure under the invention, the test ligand may be resynthesized, and assessed separately using an assay method that measures an affinity parameter. In such embodiments, the test ligand comprises the bait moiety linked to the test moiety of the test ligand identified in the prior screening procedure, wherein the bait moiety and the test moiety are linked through a linker z' that is the same as the linker z of the identified test ligand. In other embodiments, the derivative test ligand comprises the bait moiety linked to the test moiety of the test ligand identified in the prior screening procedure, wherein the bait moiety and the test moiety are linked through a linker z' that is different from the linker z of the identified test ligand.

Once a derivative test ligand has been synthesized, methods of the invention can comprises additional steps including contacting the protein with the derivative test ligand under conditions that permit binding of the protein with ligands thereto; and assessing binding between the derivative test ligand and the protein by measuring the affinity parameter for the derivative test ligand.

In another aspect, the invention comprises methods of screening for a ligand of a protein, the screening method comprising:

(a) contacting a plurality of test ligands with a protein under conditions that permit binding between the protein and a ligand thereof, wherein each test ligand comprises a preselected bait moiety attached via a linker to one of a plurality of test moieties; and (b) assessing the presence or absence of binding between a test ligand and the protein.

In another aspect, the invention comprises a method of screening for a ligand of a protein, comprising performing at least two screening procedures, each comprising:

(a) contacting a plurality of test ligands with a protein under conditions that permit binding between the protein and a ligand thereof, wherein each test ligand comprises a bait moiety attached to one of a plurality of test moieties, and wherein the bait moiety has, or comprises a fragment of a compound that has, binding affinity for the protein as measured through an affinity parameter dependent upon such binding affinity;

(b) assessing the presence or absence of binding between a test ligand and the protein by measuring the affinity parameter for a test ligand; and (c) identifying a test ligand for which a value of the affinity parameter is superior to the value of the affinity parameter for the bait moiety;

wherein a screening procedure subsequent to the first screening procedure employs as the bait moiety a test moiety identified in a prior screening procedure or a structural analog of the identified test moiety.

In another aspect, the invention comprises methods for screening for a compound that binds to a protein comprising performing at least two screening procedures, each comprising:

(a) reacting a bait fragment B-x, comprising a bait moiety B that is, or comprises a fragment of, a compound that has binding affinity for the protein, and a reactive functionality x, with a plurality of test fragments, y-$T_1$, y-$T_2$ ... y-$T_n$, each test fragment comprising a reactive functionality y and one of a plurality of test moieties, $T_1$, $T_2$ ... $T_n$, under conditions sufficient to provide a test ligand mixture comprising a plurality of test ligands, B-z-$T_1$, B-z-$T_2$ ... B-z-$T_n$, wherein z is a linker comprising a disulfide or thioether component formed by reaction of x and y;

(b) contacting the protein with two or more of the test ligands under conditions that permit binding between the protein and a test ligand thereby yielding at least one test ligand:protein complex; and (c) isolating by chromatography at least one test ligand: protein complex formed in step (b) from unbound test ligands; and (d) identifying by mass spectrometry the test moiety of a test ligand:protein complex;

wherein a screening procedure subsequent to the first screening procedure employs as the bait moiety a test moiety identified in a prior screening procedure or a structural analog of the identified test moiety.

In some embodiments, the above-mentioned methods further comprise:

(e) providing purified test ligand identified in step (d); and (f) measuring the affinity parameter for the purified test ligand to confirm the identification of the test ligand.

In another aspect, the invention comprises methods for screening for a compound that binds to a protein, comprising performing at least a first screening procedure comprising:

(a) reacting a bait fragment B-x, comprising a preselected bait moiety B and a reactive functionality x, with a plurality of test fragments (y-$T_1$, y-$T_2$, ... y-$T_n$), each test fragment comprising a reactive functionality y and one of a plurality of test moieties ($T_1$, $T_2$, ... $T_n$) under conditions sufficient to provide a plurality of n test ligands (B-z-$T_1$, B-z-$T_2$, ... B-z-$T_n$), wherein z is a linker formed by reaction of x and y;

(b) contacting the protein with one or more of the test ligands under conditions that permit binding between the protein and a ligand thereof, wherein binding between the protein and at least one of the test ligands forms at least one test ligand:protein complex;

(c) assessing the presence or absence of binding of at least one of the test ligands to the protein; and (d) identifying at least one test ligand that binds to the protein;

wherein for a screening procedure subsequent to the first screening procedure the bait moiety comprises a test moiety for which binding was identified in step (d) in a prior screening procedure or a structural analog thereof Another aspect of the present application is a method of screening for a compound that binds to a protein, the screening method comprising:

(a) providing a library comprising a plurality of test ligands, B-z-$T_1$, B-z-$T_2$ ... B-z-$T_n$, each comprising a preselected bait moiety B attached via a linker z to one of a plurality of test moieties, $T_1$, $T_2$ ... $T_n$; wherein each z may be the same or different; wherein each test ligand of the library is contained individually in one of a multiplicity of containers;

(b) contacting the protein with one or more of the test ligands under conditions that permit binding between the protein and a test ligand that binds thereto; and (c) assessing the presence or absence of binding between the test ligand and the protein.

In one embodiment, the multiplicity of containers is provided as at least one multi-well plate. In one variation, a 96-well plate is used; in another variation, a 394-well plate, in another variation a 1536-well plate. One of skill in the art can easily identify the appropriate size plate to use for the size of the library to be employed.

In one embodiment, the target is a polypeptide, especially a protein. Polypeptides, including proteins, that find use herein as targets for binding ligands, such as, for example small organic molecule ligands, include virtually any polypeptide (including short polypeptides also referred to as peptides) or protein that comprises two or more binding sites of interest. Polypeptides of interest may be obtained commercially, recombinantly, by chemical synthesis, by purification from natural source, or other approaches known to those of skill in the art.

In one embodiment the target is a protein associated with a specific human disease or condition, such as cell surface and soluble receptor proteins, such as lymphocyte cell surface receptors, enzymes, steroid receptors, nuclear proteins, allosteric enzymes, clotting factors, bacterial enzymes, fungal enzymes and viral enzymes (especially those associate with HIV, influenza, rhinovirus and RSV), signal transduction molecules, transcription factors, proteins or enzymes associated with DNA and/or RNA synthesis or degradation, immunoglobulins, hormones, various chemokines and their receptors, various ligands and receptors for tyrosine kinase, epidermal growth factor (EGF), heregulin-α and heregulin-β, vascular endothelial growth factor (VEGF), placental growth factor (PLGF), nerve growth factor (NGF), various neurotrophins and their ligands, other hormones and receptors and proteins and receptors that share 20% or more sequence identity to those disclosed herein.

In one embodiment, the target protein is selected from the group consisting of cell surface receptor proteins, soluble receptor proteins, enzymes; proteases; steroid receptors; nuclear proteins; allosteric enzymes; clotting factors; kinases; phosphatases; phosphodiesterases, thymidylate synthase; bacterial enzymes, fungal enzymes and viral enzymes; signal transduction molecules; intercellular adhesion molecules such as integrins, selectins, cadherins, immunoglobulin superfamily cellular adhesion molecules (ICAMs), transcription factors; immunoglobulins; hormones; and receptors for cytokines and chemokines Generally, enzyme targets include cysteine proteases, aspartyl proteases, serine proteases, metalloproteases, kinases, phosphatases, polymerases, and integrases. Exemplary protein:protein targets are 4-helical cytokines, trimeric cytokines, signaling modules, transcription factors, and chemokines Targets include proteins having a site of interest composed of two adjacent or adjoining subsites. One example is targets that bind peptidyl ligands, particularly where the peptidyl ligands bind in an extended mode where the side chains of the peptide contact different pockets on the protein. Another example is enzyme targets containing proximal sites for substrates and co-factors such as most ATP-processing enzymes, and purine synthesis enzymes. To illustrate, kinases possess an ATP-binding site and a conserved Asp-Phe-Gly (DFG) loop adjacent to/adjoining one another.

In a further embodiment, the receptors for cytokines are selected from the group consisting of receptors for erythropoietin, granulocyte colony stimulating factor (GCSF), granulocyte macrophage colony stimulating factor (GM-CSF), thrombopoietin, interleukins, growth hormone, prolactin, human placental lactogen, ciliary neurotrophic factor (CNTF), oncostatin, chemokines (e.g., RANTES, MIP-1β), insulin, insulin-like growth factor 1, epidermal growth factor, heregulin alpha and heregulin beta, vascular endothelial growth factor, placental growth factor, tissue growth factor alpha, tissue growth factor beta, and nerve growth factor.

In yet a further embodiment, the kinase is a serine/threonine kinase (e.g., MEK kinase, Raf-1, a Mitogen-activated protein kinase kinase kinase serine/threonine kinase, transforming growth factor beta activated kinase 1, an Aurora kinase), a tyrosine kinase, c-jun kinase, p38 map kinase, cyclin-dependent kinase 4, protein kinase C theta, spleen tyrosine kinase, intestinal cell kinase, IL2-inducible T-cell kinase/Bruton's tyrosine kinase, glycogen synthase kinase 3, protein kinase B, p21-activated kinase 1, and ALK (anaplastic lymphoma kinase), or mTOR (mammalian target of rapamycin).

In still a further embodiment, the target protein is selected from the group consisting of bonemorphogenetic proteins, such as BMP-2, follicle stimulating hormone, luteinizing hormone, CD28/B7, CD2, CD4, CD11a, CD26, CD3, CD40 ligand, CD45, CD88, apoptosis factor-1, apoptosis factor-2, human p53, bax/bcl2, mdm2, caspases, cathepsins, IL-1/IL-1 receptor, beta-secretase, HIV integrase, phosphodiesterase 4B, hepatitis C helicase, hepatitis C protease, rhinovirus protease, tryptase, cytosolic phospholipase A2, growth factor receptor-bound protein 2, TNF receptor-associated factors, Tie2, epidermal growth factor receptor, ErbB 2, fibroblast growth factors, platelet-derived growth factor, poly (ADP-ribose) polymerase (PARP), nuclear factor-kappa B, IKK beta, IKK2, STAT 6, neurokinin-1 receptor, Cdc25A, SHIP-2, IgE/IgER, zeta-chain-associated protein kinase 70, tumor necrosis factor alpha converting enzyme, LFA/ICAM, VLA-4, cytotoxic T-lymphocyte antigen 4, p55 TNF receptor, p75 TNF receptor, and Rac 2.

In one variation, the target is an interleukin selected from the group consisting of IL-2, IL-3, IL-4, IL-5, IL-6, IL-8, IL-10, IL-11, IL-12, 11-13, IL-15, and IL-18. In another variation, the target is a cathepsin selected from the group consisting of Cathepsin S, Cathepsin K, and Cathepsin F. In yet another variation, the target is a TNF receptor-associated factor selected from the group consisting of TNF receptor-associated factor 1, TNF receptor-associated factor 2, TNF receptor-associated factor 3, TNF receptor-associated factor 4, TNF receptor-associated factor 5, and TNF receptor-associated factor 6.

In another variation, the target is selected from the group of human inflammation and immunology targets including IgE/IgER, ZAP-70, lck, syk, ITK/BTK, TACE, Cathepsins S and F, CD11a, LFA/ICAM, VLA-4, CD28/B7, CTLA4, TNF alpha and beta, (and the p55 and p75 TNF receptors), CD40L, p38 map kinase, IL-2, IL-4, 11-13, IL-15, Rac 2, PKC theta, TAK-1, jnk, IKK2, and IL-18.

In another variation, the target is selected from the group of caspases 1, 3, 8, and 9, IL-1/IL-1 receptor, BACE, HIV integrase, PDE IV, Hepatitis C helicase, Hepatitis C protease, rhinovirus protease, tryptase, cPLA (cytosolic Phospholipase A2), CDK4, c-jun kinase, adaptors such as Grb2, GSK-3, AKT, MEKK-1, PAK-1, raf, TRAFs 1-6, Tie2, ErbB 1 and 2, FGF, PDGF, PARP, CD2, C5a receptor, CD4, CD26, CD3, TGF-alpha, NF-κB, IKK beta, STAT 6, Neurokinin-1 receptor, PTP-1B, CD45, Cdc25A, SHIP-2, TC-PTP, PTP-alpha, LAR p53, bax, and mdm2.

In another embodiment, the target protein is a protein that is involved in apoptosis. For example, the target may be a member of the Bcl-2 (Bcl lymphoma 2) family of proteins, which are involved in mitochondrial outer membrane permeabilization. The family includes the proapoptotic proteins Bcl-2, Bcl-$X_L$, Mcl-1, CED-9, Al, and Bfl-1; and includes the antiapoptotic proteins Bax, Bak, Diva, Bcl-$X_S$, Bik, Bim, Bad, Bid, and Egl-1.

In certain embodiments, hits obtained from a screening procedure may be screened against another biological molecule of interest to ascertain differences in the affinity parameter of the hits for the target of interest as against the other biological molecule, e.g., a protein that is closely related to the target of interest. Such screens may be referred to as counterscreens, and the other biological molecule may be referred to as a countertarget. For example, hits identified in a screening procedure against a kinase of interest, may be individually or collectively counterscreened against one or more other kinases (countertargets), to ascertain whether any of the hits demonstrates greater affinity or activity with respect to the target kinase than with respect to the countertarget kinase(s). In such cases, if a plurality of hits is identified in a screening procedure, such a counterscreen may provide a criterion for selecting one or more of the hits for use in developing baits for a subsequent screening procedure against a library of test fragments as described herein. Selecting hits for their selective affinity for or activity against targets v. countertargets can introduce additional selective pressure, to facilitate the evolution of compounds having desirable properties as contemplated herein.

EXEMPLIFICATION

All preparative reactions were carried out under an atmosphere of dry nitrogen unless otherwise noted. All commercially available starting materials and solvents were reagent grade or better and used without further purification. Flash chromatography was carried out using Merck Kieselgel 60 silica gel (230-400 mesh). Analytical TLC was carried out with EM Science silica gel 60 $F_{254}$ 2.5×7.5 cm glass plates using UV light, 1% $KMnO_4$ in water, or 3% ninhydrin in ethanol for visualization. Preparative high-performance liquid chromatography (HPLC) purification was carried out on a Gilson HPLC fitted with a Waters Nova-Pak C-18 or C-4 (25 mm×100 mm) column. $^1$H NMR spectra were recorded using a 400 MHz Bruker spectrometer with chemical shifts reported in ppm from TMS. Mass spectra were recorded on a Hewlett Packard 1100 MSD.

Standard procedures and chemical transformation and related methods are well known to one skilled in the art, and such methods and procedures have been described, for example, in standard references such as *Fiesers' Reagents for Organic Synthesis,* John Wiley and Sons, New York, N.Y., 2002; *Organic Reactions,* vols. 1-83, John Wiley and Sons, New York, N.Y., 2006; March J. and Smith M.: *Advanced Organic Chemistry,* 6th ed., John Wiley and Sons, New York, N.Y.; and Larock R. C.: *Comprehensive Organic Transformations,* Wiley-VCH Publishers, New York, 1999. All texts and references cited herein are incorporated by reference in their entirety.

Library—Experimental Procedure 3-(2-tert-Butoxycarbonylamino-ethyldisulfanyl)-propionic acid

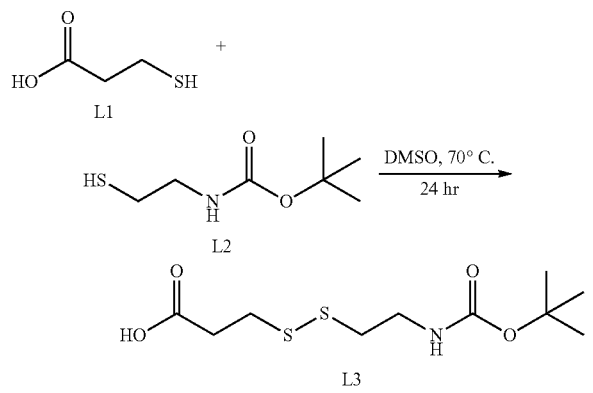

To a solution of L1 (75 mL, 424.0 mmol) in DMSO (133.5 mL) was added L2 (41.17 mL, 424.0 mmol) and the reaction mixture was then heated at 70° C. for 24 hr. The reaction progress was monitored by LCMS. The reaction mixture was cooled and ethyl acetate (EtOAc) (400 mL) was added with stirring and then extracted with 1M HEPES (pH 7.0, 2×400 mL) and the aqueous layer was discarded (di-acid). The organic layer was then extracted with saturated $NaHCO_3$ (3×300 mL). The combined aqueous layer was then acidified with 3M HCl to pH 1-2 and extracted with EtOAc (3×300 mL). The organic layer was dried ($Na_2SO_4$) and solvent was evaporated to give compound L3 (81 g, 70% yield, white powder). Compound L3 was characterized by LCMS and $^1$H NMR (dmso-$d_6$) and was stored at −78° C. to avoid decomposition.

Synthesis of Amides from Acid Scaffold—General Procedure for Alkyl Amines

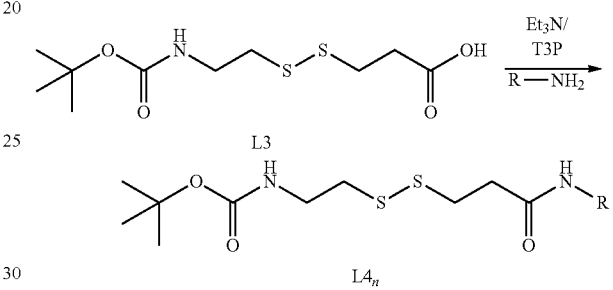

To a solution of acid scaffold L3 (125 mg. 0.44 mmol) was in dry dichloromethane (DCM; 3 mL), alkyl amine (0.44 mmol) and triethylamine (TEA; 0.5 mL, 3.58 mmol) was added and cooled to −20° C. 2-Propanephosphonic acid anhydride (143 mg, 0.44 mmol) was added and stirred at room temperature (RT) overnight. The reaction mixture was diluted with DCM, the organic layer was separated and the aqueous layer was extracted with DCM. The combined organic layers were dried and concentrated. The crude product L4$_n$ was purified by Biotage. The yield varied from 60-80%.

Synthesis of Amides from Acid Scaffold—General Procedure for Aryl Amines

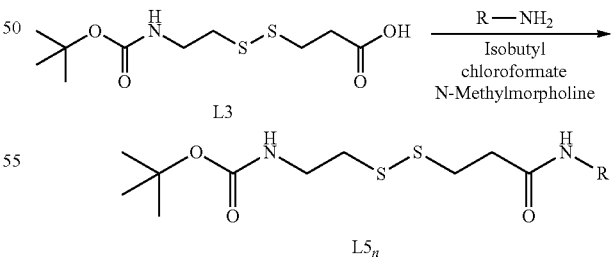

To a solution of the acid scaffold L3 (125 mg, 0.44 mmol) in dry tetrahydrofuran (THF; 5 mL), N-methylmorpholine (44 mg, 0.44 mg) was added dropwise at −30° C. and stirred for 10 min. Isobutyl chloroformate (60.64 mg, 0.44 mol) was added dropwise and the stirring was continued for 30 min. This mixture was added to a solution of aryl amine (0.44 mmol) in 2 mL of THF at RT and stirred for 3 hr. The solvent was evaporated and the residue was dissolved in EtOAc. The organic layer was washed with sat. NaHCO₃ solution, dried, and concentrated. The crude product L5$_n$ was purified by Biotage. The yield varied from 60-80%.

Cysteamine Linker Synthesis

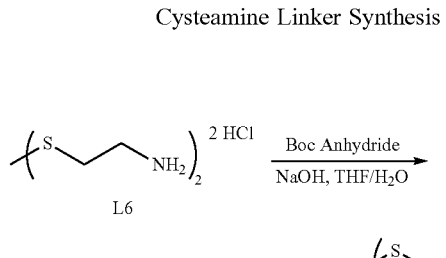

To a cooled (0° C.) solution of NaOH (71 g, 1.78 mol) in H₂O (630 mL) were added cysteamine dihydrochloride L6 (100 g, 440.0 mmol) and THF (400 mL), and the reaction mixture was stirred until homogeneous. Boc-anhydride (193 g, 880.0 mmol) in THF (230 mL) was then added dropwise via an addition funnel and stirred at RT. The reaction progress was monitored by LC/MS. THF was evaporated and filtered under vacuum to yield crude L7 as a white solid, which was then triturated in hexane, filtered, washed (5× hexane) and dried under vacuum to afford L7 (143 g, 92%) as a white solid. Compound L7 was used in the next step without further purification.

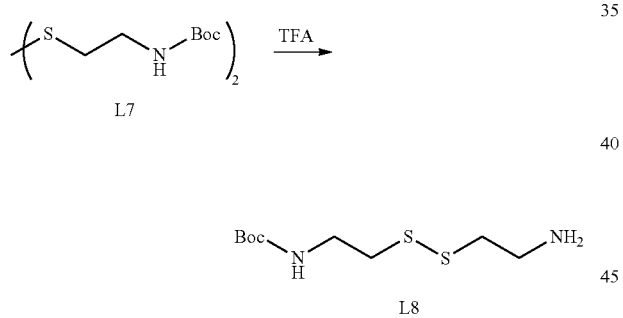

Preparation of L8: To a solution of L7 (55 g, 156 mmol) in DCM (300 mL) was added a 1:1 solution of TFA:DCM (110 mL) drop-wise. The reaction progress was then followed by LCMS, to monitor the ratio of the desired product L8 to starting material L7, adding additional TFA until the ratio of L8 to L7 was approximately 3:1. NaOH (4 M) was added slowly to adjust the pH to 4-5. Increasing the pH past 5 tended to decrease the final yield. The biphasic solution was then concentrated and the precipitate filtered and rinsed with HCl (1M, 3×). The acidic layer was extracted with EtOAc. The pH was again raised to 5 with aq. NaOH (4 M) and extracted with EtOAc (2×), followed by a final EtOAc extraction at pH 11. The combined organic layers were washed carefully with sat. NaHCO₃ (2×), brine (1×), dried (MgSO₄) and evaporated. The residue was dried under high vacuum for a minimum of 16 hr (to remove residual EtOAc) to afford product L8 as an orange oil (33g, 83%). Compound L8 needs to be stored at −78 ° C. to avoid decomposition.

Synthesis of Ureas from Alkyl Amines

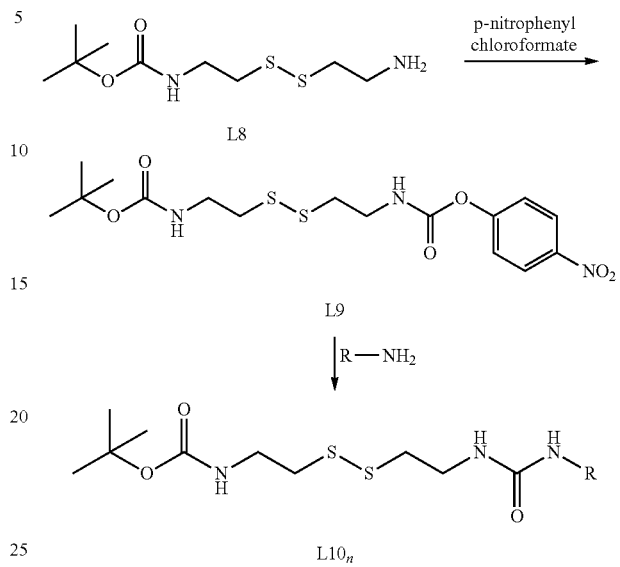

1. Synthesis of carbamate. The mono-BOC-cystamine L8 (5 g, 19.80 mmol) was dissolved in dry THF (100 mL) and TEA (3 mL, 21.8 mmol)) was added. The reaction mixture was cooled to 0° C. and p-nitrophenyl chloroformate (4.3 g, 21.80 mmol) was added at once. After completion of the reaction, the solvent was removed under reduced pressure and diethyl ether was added to give the expected pure carbamate L9 (6 g, 72%).

2. Synthesis of ureas from carbamate. To a solution of above carbamate L9 (200 mg, 0.48 mmol) in dry DCM (3 mL), TEA (0.16 mL, 1.2 mmol) was added and cooled to 0° C. Then the alkyl amine (0.48 mmol) was added stirred at RT overnight. The solvent was evaporated and the crude product L10$_n$ was purified by Biotage.

Synthesis of Ureas from Aryl Amines

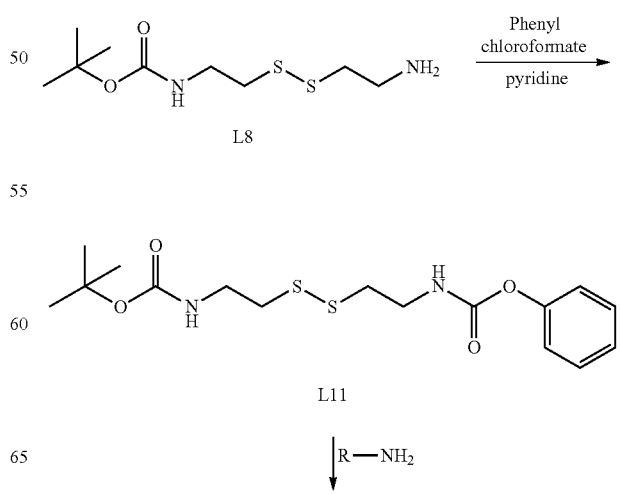

-continued

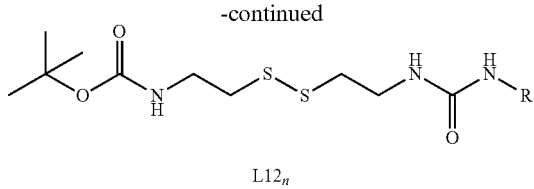

L12$_n$

1. Synthesis of phenyl carbamate. The mono-BOC-cystamine L8 (5 g, 19.84 mmol) was dissolved in dry THF (100 mL) and cooled to 0° C. To the mixture were added pyridine (1.96 g, 24.80 mmol) and phenyl chloroformate (2.56 mL, 20.40 mmol) dropwise. The resulting suspension was stirred at 0° C. for 5 min and allowed to warm to RT for 1 hr. Ethyl acetate (200 mL) was added and washed successively with aq. 1 N HCl (50 mL), water (50 mL), sat. aq. NaHCO$_3$ (50 mL), brine (50 mL), dried and concentrated under reduced pressure to give the crude product. The crude product was triturated with ether-hexane mixture to afford 6.65 g (90%) of the carbamate L11.

2. Synthesis of ureas using aryl amines. To a solution of carbamate L11 (150 mg, 0.403 mmol) is dissolved in dry DMSO (2 mL), aryl amine (0.403 mmol) was added followed by TEA (0.1 mL, 0.717 mmol). The reaction mixture was stirred at 80° C. for overnight. Ethyl acetate (15 mL) was added and washed successively with water, aq. 1 N HCl, water, aq. 1 N NaOH, brine, dried and concentrated under reduced pressure. The crude product L12$_n$ was purified by Biotage.

Synthesis of Ureas Using Triphosgene

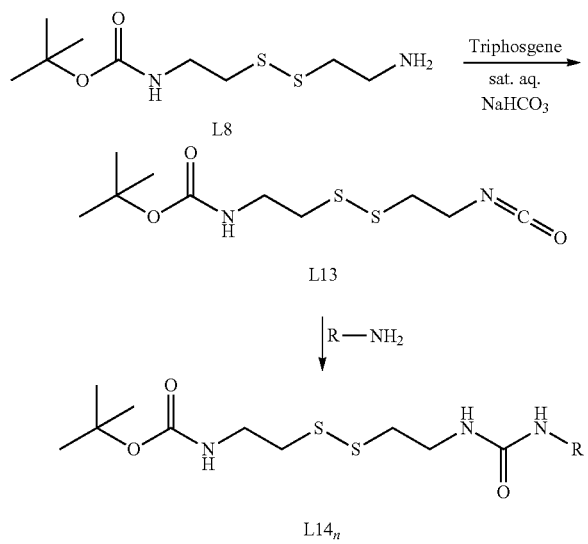

To a solution of mono-BOC-cystamine L8 (1 g, 3.90 mmol) in dry DCM (18 mL), sat. aq. NaHCO$_3$ (18 mL) was added. The biphasic mixture was cooled in an ice-bath and triphosgene (381 mg, 1.30 mmol) was added at once. The reaction mixture was stirred in the ice-bath for 15 min and then poured into a reparatory funnel. The organic layer was collected and the aqueous layer was extracted thrice with DCM. The combined organic layers were dried with Na$_2$SO$_4$, concentrated under reduced pressure to afford the desired isocyanate L13 (1.1 g, 99.7%).

The amines (0.9 eq.) were taken in 8 mL vials and dissolved in 1 mL of dry DCM. The solution was cooled to 0° C. and a solution of above isocyanate (200 mg, 0.718 mmol) in DCM was added and stirred at RT overnight. The solvent was evaporated and the crude mixture was purified by Biotage to get the desired product L14$_n$.

General Procedure for the De-Protection of BOC-Group

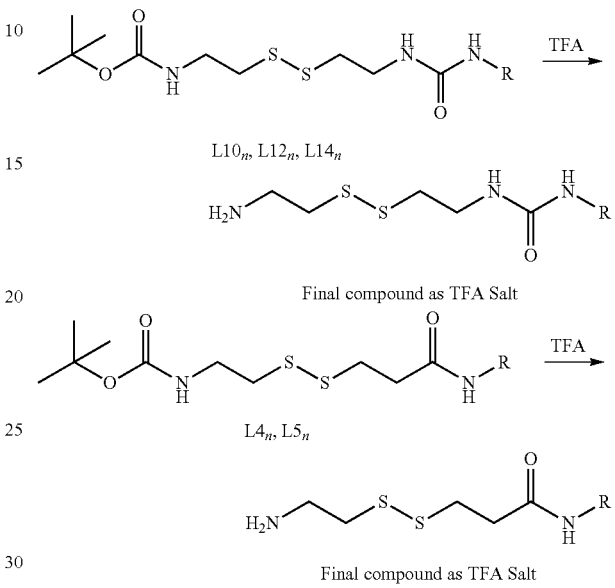

The Boc-compound L4$_n$, L5$_n$, L10$_n$, L12$_n$, or L14$_n$ was dissolved in 3 mL of dry DCM and cooled to 0° C. Trifluoroacetic acid (TFA; 0.5 mL, 50% solution in DCM) was added and stirred at RT overnight. The reaction mixture was concentrated under high vacuum to remove TFA and then analyzed by HPLC. Compounds were purified by Biotage.

Procedure for the Carboxylic-Acid Derived Library Memberse

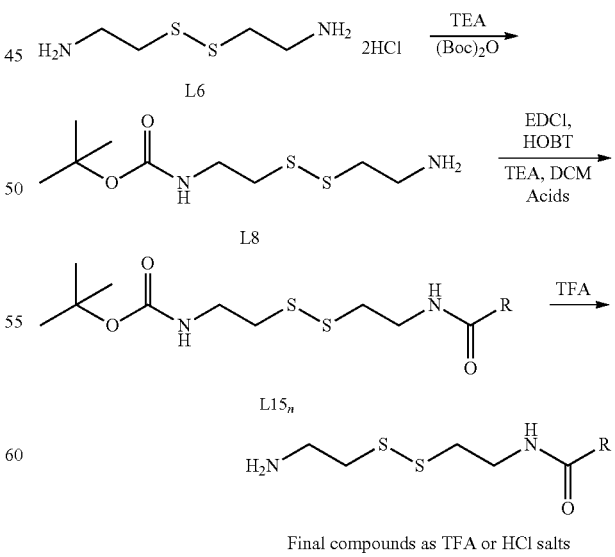

The synthesis of carboxylic-acid derived library members involved three steps. It was completed using a synthetic method as shown in Scheme 1, which illustrates the synthesis of the target compound. A total of 354 acids were obtained and used for library production; 307 products (TFA or HCl salts) were successfully obtained (quantity >25 mg, purity >90%). The success rate was 87%.

1. Preparation of Scaffold B:

Preparation of [2-(2-Amino-ethyldisulfanyl)-ethyl]-carbamic acid tert-butyl ester: Cysteamine dihydrochloride L6 (168.75 g, 750 mmol) was dissolved in a solution of 23% TEA in CH$_3$OH (1600 mL). A solution of di-tent-butyldicarbonate (66 g, 300 mmol) in methanol (150 mL) was added to this mixture with vigorous stirring. The mixture was refluxed for 2 hr and then left to stir at RT for 16 hr. The methanol and TEA were removed in vacuo, and water was added into the mixture. Aqueous NaOH solution (4.0 M) was added slowly to adjust the pH to 4-5 and the filtrate collected by filtration. The precipitate was washed with aqueous HCl (1.0 M, 50 mL). The acidic layer was extracted with EtOAc (250 mL). The pH value was adjusted to 5 with NaOH (4.0 M) and extracted with EtOAc (250 mL), followed by a final extraction (250 mL EtOAc) at pH 11. The combined organic layers were washed carefully with saturated aqueous NaHCO$_3$ solution (2×200 mL), brine (2×200 mL), dried over Na$_2$SO$_4$ and filtered, evaporated to give the product L8 as an orange oil (60 g, 32%). $^1$H NMR (300 MHz, CDCl$_3$): δ 1.50 (s, 9H), 2.77-2.83 (m, 4H), 3.04 (t, J=6 Hz, 2H), 3.74-3.49 (m, 2H), 4.97 (m, 1H); LC-MS: (M+H)$^+$ 253; HPLC>95%.

2. Library Production 2.1 Preparation of intermediate L15$_n$: A mixture of the acid (1.3 mmol), [2-(2-amino-ethyldisulfanyl)-ethyl]-carbamic acid tert-butyl ester L8 (505 mg, 2 mmol), EDCI (1-ethyl-3-(3-dimethylaminopropyl)carbodiimide hydrochloride) (498 mg, 2.6 mmol), 1-Hydroxybenzotriazole (HOBT) (270.2 mg, 2 mmol), TEA (657 mg, 6.5 mmol) in CH$_2$Cl$_2$ (10 mL) was stirred at ambient temperature for 16 hr. The reaction mixture was evaporated to dryness and purified by silica gel column chromatography to give desired compound. Silica gel column chromatography: 300~400 mesh silica, column size (1.5×12 cm), eluted with CH$_2$Cl$_2$ : CH$_3$OH 100/1: 20/1.

2.2 Preparation of library amides (Trifluoroacetic acid salt.) Intermediate L15$_n$ (200 mg) was dissolved in a mixture of TFA (1 mL) and CH$_2$Cl$_2$ (10 mL), and stirred at ambient temperature for 3 hr. The solvent was removed in vacuo, and the residue was evaporated twice with CH$_2$Cl$_2$ (25 mL) to remove residual TFA. The residue was then washed with ether (2×25 mL) and dried to give TFA salts.

2.3 Preparation of library amides (HCl salt). Intermediate L15$_n$ (200 mg) was dissolved in a mixture of TFA (1 mL) and CH$_2$Cl$_2$ (10 mL), and stirred at ambient temperature for 3 hr. The solvent was removed in vacuo, and the residue was evaporated twice with CH$_2$Cl$_2$ (25 mL) to remove residual TFA. Then the residue was dissolved in EtOAc (10 mL), to which saturated HCl solution in EtOAc (2 mL) was added drop-wise with stirring. The solvent was removed, and the solid was washed with ether (2×25 mL) and dried to give HCl salts.

Following analysis of the final compounds, if the purity is observed to be lower than 90%, the crude product was purified by preparative thin layer chromatography (TLC) or preparative HPLC. It should be noted, however, that on occasion the purity was decreased from >98% to <90% after concentration at ambient temperature following preparative HPLC. Preparative HPLC condition: column (Venusil XBP-C18, 250×20 mm, 10 μm), wavelength (214 nm), mobile phase (MeOH/H$_2$O/TFA 65:35/0.001), isocratic.

Example 1

Compound 4

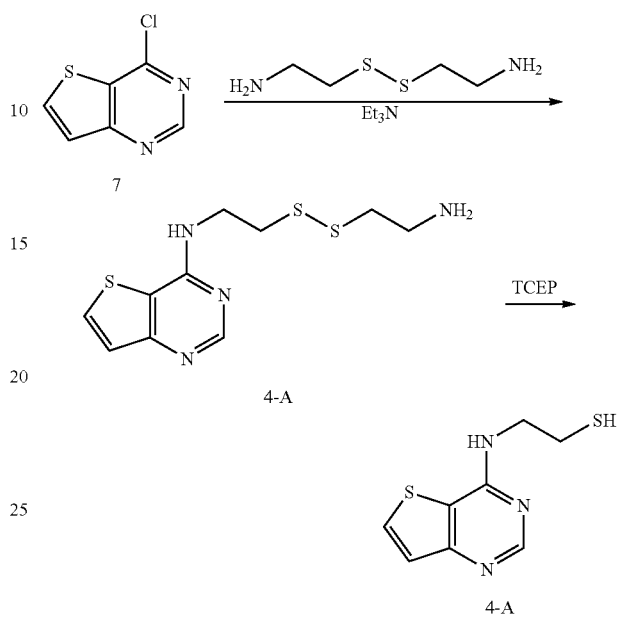

A mixture of 4-chlorothieno[3,2-d]pyrimidine (0.698 g, 4.09 mmol) and cystamine dihydrochloride (0.462 g, 2.05 mmol) was suspended in 10 mL of dry dimethylformamide (DMF), and TEA (1.14 mL, 8.2 mmol) was added. The reaction was heated under nitrogen for 2 days at 60° C., evaporated to dryness, and triturated with 50 mL of water to remove the symmetrical disulfide. The precipitate was washed with 2×25 mL water, and the combined aqueous fractions were treated with tris-2-carboxyethylphosphine hydrochloride (0.59 g, 2.05 mmol) and 7 mL 1 M sodium hydroxide to bring the solution to pH 7. After 20 min the reaction was extracted with 3×30 mL EtOAc, the combined organics were rinsed with 40 mL brine, dried over sodium sulfate, filtered, and evaporated to 0.216 g of colorless solid which was purified by silica gel chromatography (95:5 DCM : MeOH, 14.5×4.25 cm column) to yield 150 mg of white solid. This was further purified by reverse phase HPLC to yield a total of 89 mg of Compound 4 as a white solid. ES (+) MS m/e=212 (M+1).

Example 2

Compound 5

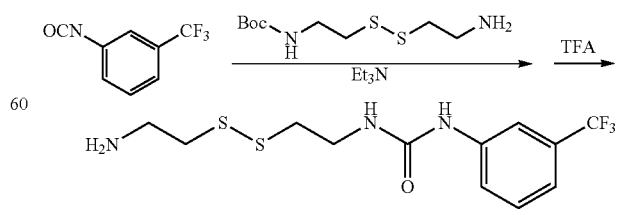

Mono-Boc cystamine (tosylate salt, 0.349 g, 0.823 mmol) was suspended in 20 mL dry DCM and TEA (0.12 mL, 0.863 mmol) was added with stirring, followed by α,α,α-trifluoromethyl-tolyl-isocyanate (0.12 mL, 0.857 mmol). After 1 hr the reaction was evaporated to dryness, flooded with 50 mL EtOAc, rinsed with 2×25 mL 1 M NaOH, 2×25 mL 1 M HCl, 25 mL brine, dried over sodium sulfate, filtered, and evaporated to yield a yellow-brown oil. This was dissolved in 10 mL dry DCM and 10 mL TFA was added with stirring. After 30 min the reaction was evaporated to dryness, co-evaporated twice with DCM, and purified by reverse phase HPLC to yield 101 mg of Compound 5 as a colorless glass. ES (+) MS m/e=340 (M+1).

Example 3

Compound 6 and Compound 8 next day the reaction was quenched with 34 mL of 1 M HCl and 30 mL water, extracted with 3×25 mL EtOAc, and the combined organics were washed with 35 mL brine, dried over sodium sulfate, filtered, and evaporated to a yellow oil which was purified by silica gel column chromatography (95:5 DCM:MeOH, 15×4.25 cm column) to yield Intermediate 1 as a white solid (0.386 g, 1.17 mmol, 41%). ES (+) MS m/e=332 (M+1).

Intermediate 2: Intermediate 1 (0.386 g, 1.17 mmol) was dissolved in 9 mL of dry THF, and phosphorus tribromide (0.6 mL of 1 M stock in DCM, 0.6 mmol) was added under nitrogen. After 30 min the reaction was evaporated to dryness, and potassium thioacetate (0.139 g, 1.22 mmol) was added, followed by 5 mL dry DMF and diisopropylethylamine (0.61 mL, 3.51 mmol). After 20 min of vigorous stirring the reaction was flooded with EtOAc, rinsed with 25 mL water, 25 mL saturated sodium bicarbonate, 25 mL brine, dried over sodium sulfate, filtered, evaporated to

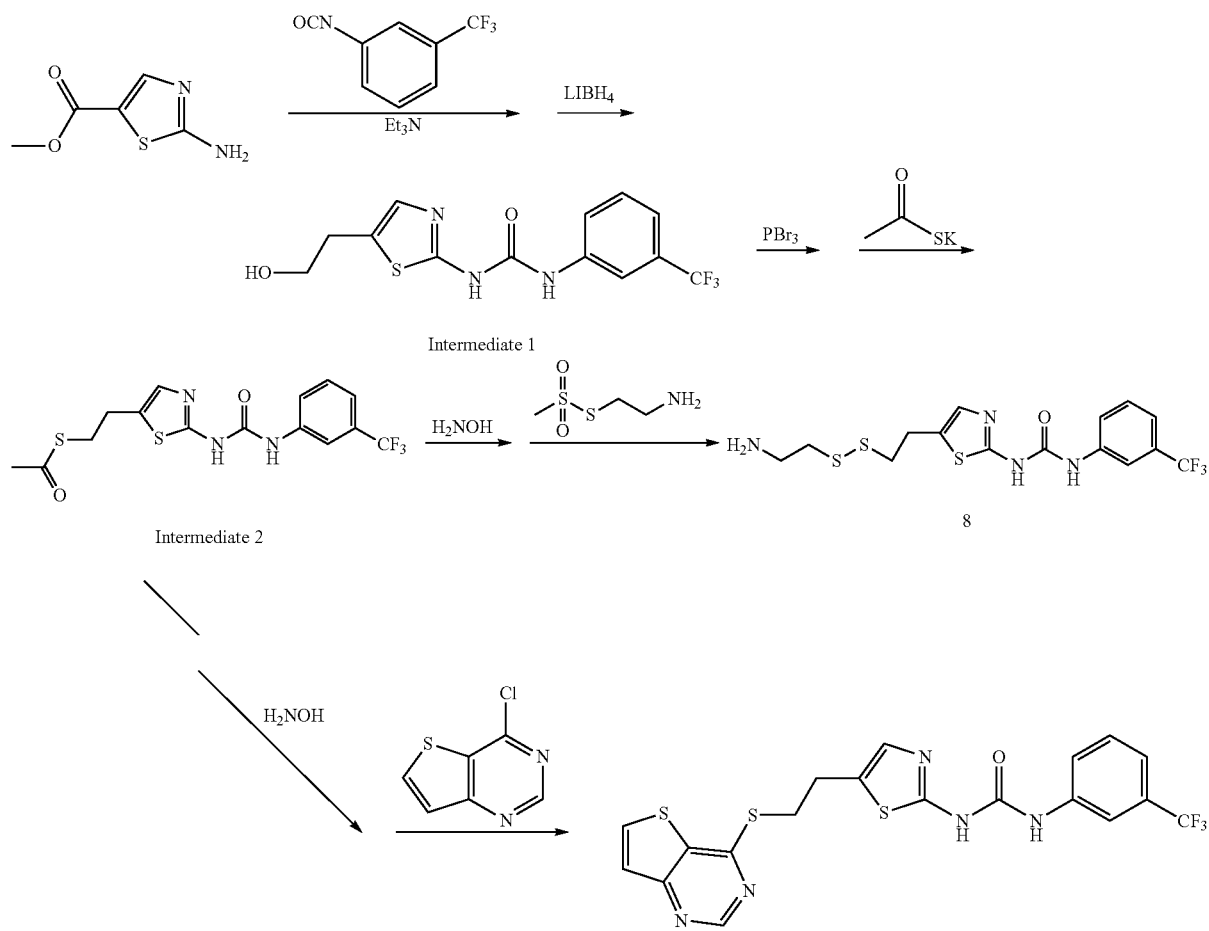

Intermediate 1: (2-Amino-thiazol-5-yl)-acetic acid methyl ester (0.488 g, 2.83 mmol) was suspended in 12 mL dry THF, and α,α,α-trifluoromethyl-tolyl-isocyanate (0.4 mL, 2.86 mmol) was added, followed by another 20 mL THF. After 30 min TEA (0.4 mL, 2.88 mmol) was added, and the reaction was allowed to stir for 8 hr. Then lithium borohydride (4.3 mL of 2 M stock in THF, 8.6 mmol) was added, and the reaction was allowed to stir overnight. The dryness, and purified by silica gel chromatography (97.5:2.5 DCM:MeOH, 15×4.25 cm column) to yield Intermediate 2 (0.103 g, 23%) as an off-yellow oil. ES (+) MS m/e=390 (M+1).

Compound 8: Intermediate 2 (51 mg, 0.132 mmol) was dissolved in 2 mL methanol, 2-(aminoethyl)methanethiosulfonate hydrobromide (36 mg, 0.152 mmol) was added, followed by hydroxylamine (0.02 mL 50% in water, 0.653 mmol). After 1 hr this was purified by reverse phase HPLC to yield Compound 8 as a white solid. ES (+) MS m/e=423 (M+1).

Compound 6: Intermediate 2 (43 mg, 0.111 mmol) was mixed with 4-chlorothieno[3,2-d]pyrimidine (105 mg, 0.615 mmol), dissolved in 3 mL dry DMF, and hydroxylamine (0.01 mL of 50% in water, 0.327 mmol) and TEA (0.02 mL, 0.144 mmol) was added. After 3 hr an additional 0.08 mL (0.719 mmol) of TEA was added, and the reaction was allowed to proceed under nitrogen for 72 hr. The reaction was then purified by reverse phase HPLC to yield Compound 6 as a yellow solid. ES (+) MS m/e=482 (M+1).

Example 4

Compound 24

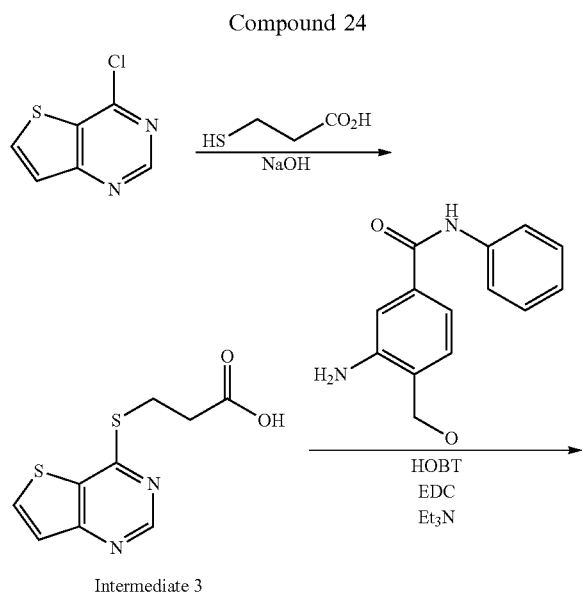

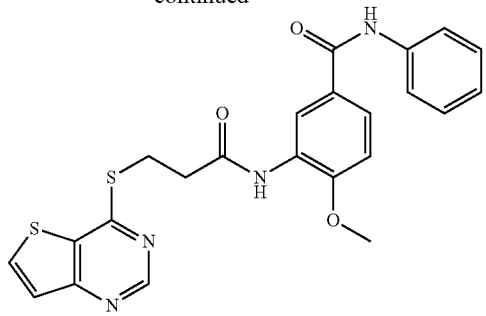

24

Intermediate 3: A mixture of 4-chlorothieno[3,2-d]pyrimidine (0.550 g, 3.22 mmol) and 3-mercaptopropionic acid (0.29 mL, 3.32 mmol) was suspended in 6.5 mL of 1 M NaOH (6.5 mmol). After several hours suspended solids had dissolved, and after 8 hr the reaction was neutralized with 3.2 mL 1 M HCl to produce a thick white paste. This was diluted with 10 mL water, filtered through a medium glass frit, rinsed with 2×20 mL water, and the solid was dried under reduced pressure to yield the free acid, Intermediate 3, as an off white solid (0.656 g, 2.73 mmol). ES (+) MS m/e=241 (M+1).

Compound 24: A mixture of the free acid, Intermediate 3, from above (88 mg, 0.366 mmol), EDCI (72 mg, 0.376 mmol), and HOBT (50 mg, 0.37 mmol) was suspended in 1 mL dry DMF, and 3-amino-4-methoxybenzanilide (88 mg, 0.364 mmol) was added, followed by 2 mL more DMF and TEA (0.16 mL, 1.15 mmol). This was heated under nitrogen to 60° C. overnight, flooded with 40 mL EtOAc, rinsed with 2×20 mL 1 M HCl, 2×20 mL 1 M NaOH, 20 mL brine, dried over sodium sulfate, filtered, evaporated to dryness, and purified by reverse phase HPLC to yield Compound 24 (31 mg) as a yellow solid. ES (+) MS m/e=465 (M+1).

Example 5

Compound 15 and Compound 16

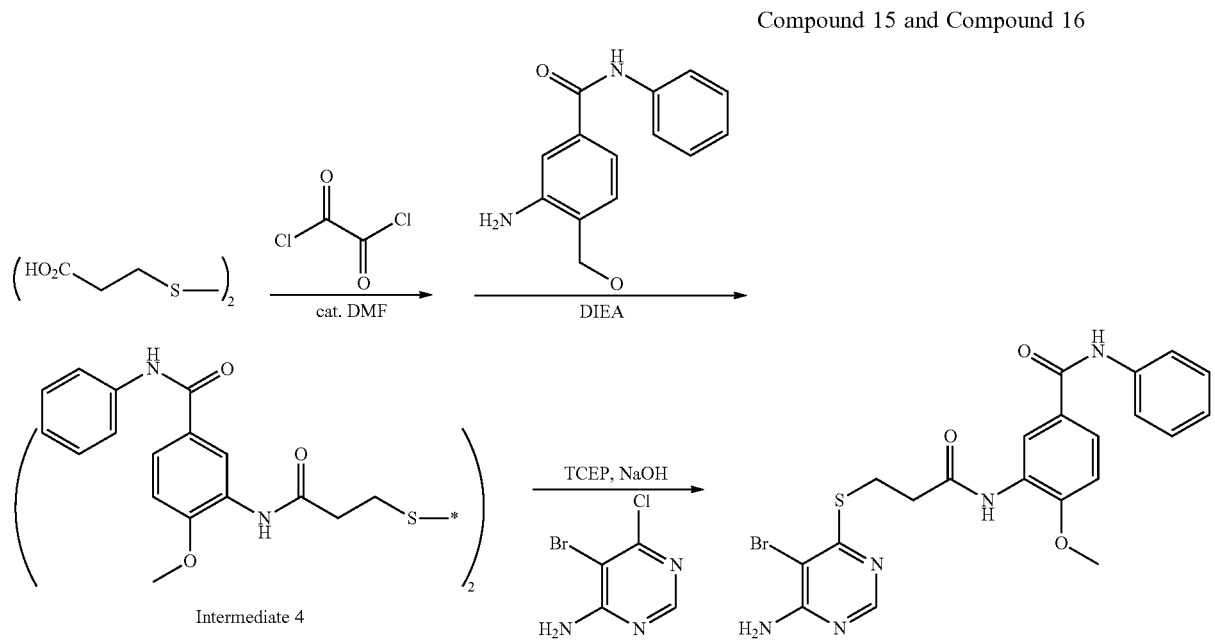

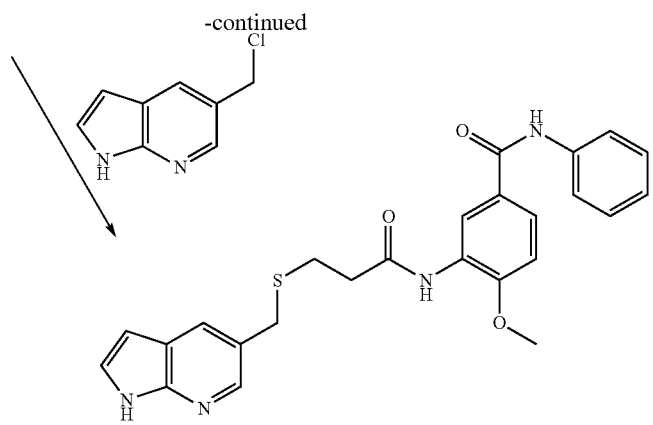

16

Intermediate 4: 3,3'-Dithiopropionic acid (0.459 g, 2.18 mmol) was suspended in 20 mL EtOAc, and oxalyl chloride (0.58 mL, 6.65 mmol) was added under nitrogen, followed by DMF (0.05 mL). After 20 min the reaction was evaporated to an off-white film. This was redissolved in 15 mL dry DCM, and 3-amino-4-methoxybenzanilide (1.04 g, 4.3 mmol) was added, followed by N,N-diisopropylethylamine (DIEA) (0.78 mL, 4.49 mmol) and an additional 20 mL DCM. After 80 min the dense white slurry was filtered through a medium glass frit, rinsed with 2×20 mL DCM, 2×25 mL 1 M HCl, 2×25 mL 1 M NaOH, 2×50 mL water, and evaporated to dryness to yield the symmetrical disulfide, Intermediate 4, as an off-white solid (0.937 g, 65%). ES (+) MS m/e=659 (M+1).

Compound 15: The disulfide, Intermediate 4, from above (111 mg, 0.169 mmol) was mixed with tris-2-carboxyethyl-phosphine hydrochloride (53 mg, 0.185 mmol) and DMF (2 mL), 1 M NaOH (0.88 mL, 0.88 mmol), and 4-amino-5-bromo-6-chloro-pyrimidine (70mg, 0.336 mmol) were added. The reaction was allowed to stir at RT overnight, whereupon it was flooded with 50 mL EtOAc, rinsed with 2×25 mL water, 25 mL brine, dried over sodium sulfate, filtered, evaporated to dryness, and purified by reverse phase HPLC to yield Compound 15 (31 mg) as a white solid. ES (+) MS m/e =504 (M+1).

Compound 16: The disulfide, Intermediate 4, from above (99 mg, 0.15 mmol) was mixed with tris-2-carboxyethyl-phosphine hydrochloride (48 mg, 0.167 mmol) and DMSO (2 mL), followed by 1 M NaOH (1.3 mL, 1.3 mmol), 5-chloromethyl-1H-pyrrolo-2,3-d]pyridine hydrochloride (65 mg, 0.32 mmol), and 1 mL more DMSO. The reaction was allowed to proceed for one day, after which it was flooded with 40 mL EtOAc, rinsed with 2×20 mL 1 M NaOH, 20 mL brine, dried over sodium sulfated, filtered, evaporated to dryness, and purified by reverse-phase HPLC to yield Compound 16 (36 mg) as a white solid. ES (+) MS m/e =461 (M+1).

Example 6

Compound 3

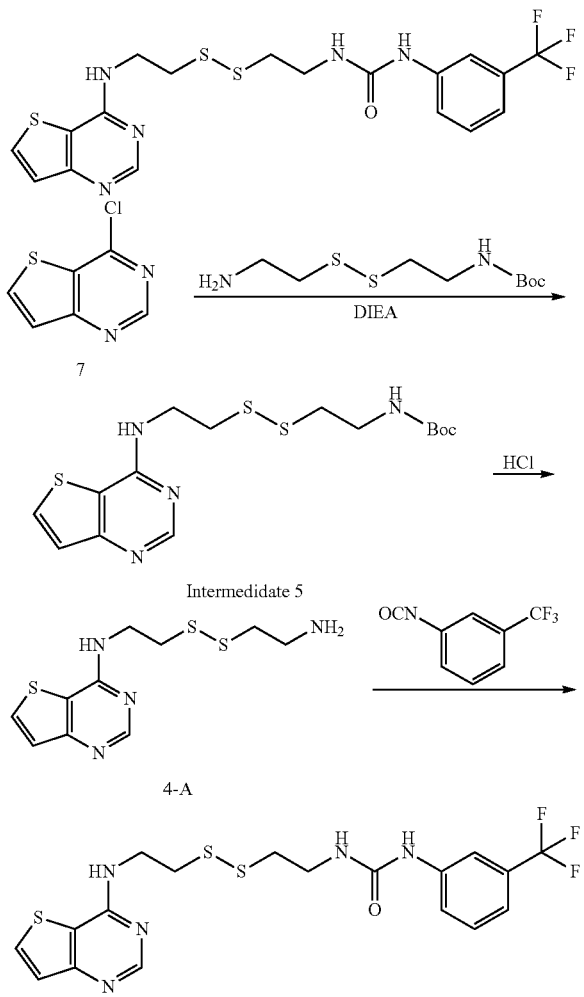

A mixture of mono-Boc cystamine (tosylate salt, 0.212 g, 0.500 mmol), 4-chlorothieno[3,2-d]pyrimidine (0.188 g, 0.550 mmol) and DIEA (0.096 mL, 1.0 mmol) was dissolved in i-PrOH (1 mL) and CH$_3$CN (1 mL). The resulting solution was stirred at 80° C. for 20 hr and the volatile had been removed in vacuo. Purified by silica gel chromatography (EtOAc/Hexanes 10%-50%) to afford Intermediate 5 (0.158 g, 0.409 mmol, 82% yield) as colorless solid. To a solution of Intermediate 5 (77.3 mg, 0.2 mmol) in MeOH (1 mL) a solution of 4 N HCl/dioxane (1 mL) was added. The resulting solution was stirred at RT for 3 hr and after the volatile was removed in vacuo. The mixture was re-dissolved in DCM (1 mL) followed by the addition of DIEA (0.058 mL, 0.6 mmol) and α,α,α-trifluoromethyl-tolyl-isocyanate (0.028 mL, 0.200 mmol) and stirred at RT for 15 min. Concentrated and purified by silica gel chromatography (MeOH/DCM, 1%-10%) to afford Compound 3 (67 mg, 0.141 mmol, 71% yield) as colorless solid. ES (+) MS m/e=474 (M+1).

Example 7

Compound 17

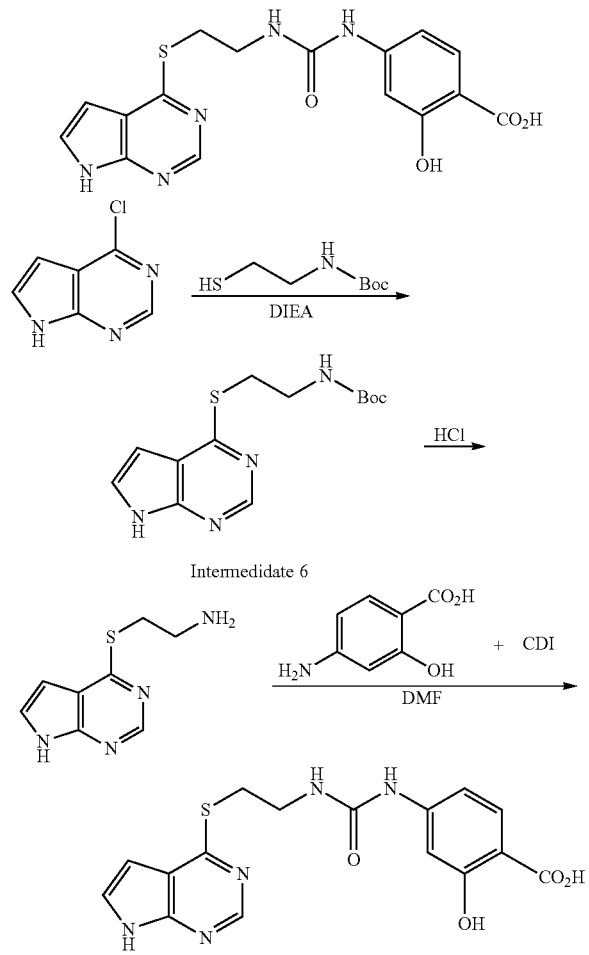

17

A mixture of 4-Chloro-7H-pyrrolo[2,3-d]pyrimidine (0.077 mg, 0.500 mmol), (2-mercapto-ethyl)-carbamic acid tent-butyl ester (0.088 g, 0.500 mmol) and DIEA (0.096 mL, 1.0 mmol) was dissolved in i-PrOH (1 mL) and CH$_3$CN (1 mL). The resulting solution was stirred at 80° C. for 20 hr and the volatile had been removed in vacuo. Purified by silica gel chromatography (EtOAc/Hexanes 10%-50%) to afford Intermediate 6 (0.112 g, 0.38 mmol, 76% yield). To a solution of Intermediate 6 (59.1 mg, 0.2 mmol) in MeOH (1 mL) a solution of 4 N HCl/dioxane (1 mL) was added. The resulting solution was stirred at RT for 3 hr and after the volatile was removed in vacuo. The mixture was re-dissolved in DMF (1 mL) followed by the addition of DIEA (0.058 mL, 0.6 mmol) and the solution was added into a mixture of 4-aminosalicylic acid (0.031 g, 0.200 mmol), 1,1'-carbonyldiimidazole (0.033 g, 0.2 mmol), and DIEA (0.038 mL, 0.4 mmol) in DMF (1 mL). The resulting mixture was stirred at RT for 16 hr. Concentrated and purified by purified by reverse phase HPLC to afford Compound 17 (16 mg, 0.042 mmol, 21% yield). ES (+) MS m/e=374 (M+1).

Example 8

Aurora A Kinase Assay: Humanized mouse Aurora A (amino acids 107-403) was expressed in E. coli as described herein. For IC50 assays, thioether reaction mixtures were titrated three-fold in DMSO and diluted 20-fold into assay buffer containing ATP and FAM-PKAtide at final concentration of 10 μM ATP and 50 nM PKAtide. The kinase reaction was initiated by adding Aurora A at a final concentration of 0.3 nM and incubated at 21° C. for 30 min. As a positive control for enzyme activity, the reaction mixture was added to DMSO and as a negative control for enzyme activity, the reaction mixture was added to Compound 1 at a final concentration of 5 μM. Both control reactions were conducted in triplicate. To detect phosphorylated PKAtide, the kinase reaction was combined with Progressive Binding Solution (1:400 Progressive Binding Reagent, 1× Buffer A, Molecular Devices) in a 1:3 ratio. The mixture was incubated for 30 min at 25° C. and the plate was scanned on an Analyst AD with excitation at 485 nm and emission at 530 nm. The fluorescence polarization value "P" is defined by equation (1) below, where "Fpar" is the fluorescence intensity parallel to the excitation plane and "Fperp" is the fluorescence intensity perpendicular to the excitation plane. The value "mP" was generated by multiplying the P value for each reaction well by a factor of 1000. The percent relative enzymatic activity ("Y" values) was calculated by normalizing the mP value for each well to the average positive control. Relative enzymatic activity values were plotted as a function of the logarithm of compound concentration ("x") and 1050 values were generated in GraphPad Prism software version 4.01 using Equation (2), where "x" is the logarithm of compound concentration and "Top", "Bottom" and "HillSlope" are curve parameters calculated by the software. IC50 values were calculated as the concentration of compound at which enzymatic activity is 50%.

$$P = \frac{(Fpar - Fperp)}{(Fpar + Fperp)} \quad \text{Eq 1}$$

$$Y = \text{Bottom} + \frac{\text{Top} - \text{Bottom}}{1 + 10^{((LogIC50 - x) * HillSlope)}} \quad \text{Eq 2}$$

Fragment Library Pilot Screen. Fragment molecule plates were screened in 96-well plates at 5 μM in single-point format in the Aurora A Kinase assay as described above. All reaction mixtures resulting in greater than or equal to 50% inhibition of enzymatic activity were then tested in an IC50 assay. Original screening samples were used for follow-up IC50 experiments. LC/MS analysis was conducted on fragment assembly screening plates to confirm presence of desired test ligand in the reaction mixture. Confirmed hits were then resynthesized as purified thioether compounds and tested in an IC50 assay.

Z-factor is a statistic that describes the degree of variability of a screening assay. Generally, prior to starting an assay, analysis is completed to assess the quality of an assay on a smaller scale, and predict if the assay would be useful in a high-throughput setting. The Z-factor predicts if useful data could be expected if the assay were scaled up to millions of samples. Generally, a Z-factor between 0.5 and 1 result from an excellent assay. A Z-factor of 1 is approached when the assay has a huge dynamic range with small standard deviations. Where "σ" is the standard deviation and "μ" is the mean of positive (p) and negative (n) controls, the Z-factor can be calculated according to Equation (3):

$$Z\text{-factor} = 1 - \frac{3 \times (\sigma_p + \sigma_n)}{|\mu_p - \mu_n|} \quad \text{Eq 3}$$

Production and Screening of Fragment Assembly Libraries

Test fragment libraries are kept in DMSO in 96-well plates with columns 1 through 10 designated for storage of a single unique disulfide test fragment per well, up to 80 in total, and columns 11 and 12 are designated for controls. Test ligand libraries are assembled on a robotic platform in 96-well plates through successive addition of reaction buffer, monomeric library test fragments, and monomeric bait fragments. Upon completion of assembly reactions, reaction mixtures are diluted in DMSO to 20× final concentration, and positive and negative controls are then added to columns 11 and 12 of each plate. Two-microliter (2 μL) aliquots of these libraries are transferred to an empty 96-well assay plate and assay reagents are then added according to specific protocol.

Library Assembly through Thioether Chemistry. Eight microliter (8 μL) aliquots of test fragment was added to 2 μL of an aqueous solution of tris(2-carboxyethyl)phosphine HCl (TCEP) and NaOH (final concentration: 25 mM test fragment, 25 mM TCEP, and 175 mM NaOH, 20% water) in 96-well plates. This mixture was incubated for five minutes at 21° C. to produce an activated test fragment solution. 10 μL of purine-mimetic bait fragment was then added to the 96-well plate containing activated fragments at a final concentration of 25 mM bait fragment and 12.5 mM test fragment. This reaction was incubated for 1 hr at 21° C. for all purine mimetics with the exception of the dimethoxyquinazoline, which required a 4-hr incubation.

Alternative Thioether Reaction Conditions. Thioether reactions can also be conducted at lower reagent concentrations than the ones described above. Under these conditions, test fragment is added to TCEP and NaOH, as above, but at a final concentration of 0.5 mM fragment, 0.75 mM TCEP, and 6 mM NaOH. Bait fragment is then added to the activated fragment at final concentrations of 0.5 mM bait and 0.33 mM test fragment, and incubated at 21° C. for the appropriate duration.

Library Assembly Through Disulfide Chemistry. Ten microliters (10 μL) of purine mimetic bait in Tris-Cl pH 8 buffer was added to a 96-well plate. Ten microliters (10 μL) of test fragment was then added to the bait solution at a final concentration of 1 mM test fragment, 2 mM bait fragment, and 100 mM Tris-Cl pH 8. The reaction was incubated for 1 hr at 21° C.

384-Well Library Screening. Library production and screening can also be conducted in 384-well plate format. In this case, fragment molecules are kept in columns 1 through 22 and controls are kept in columns 23 and 24. For thioether reactions, 10 μL test fragment is added at to 10 μL TCEP and NaOH in 384-well plates and after incubation, 10 μL bait fragment is then added to 20 μL of the activated test fragment. For disulfide reactions, 10 μL test fragment molecule is added to 10 μL purine mimetic bait.

Iterative Chemotype Evolution

Figure 2:
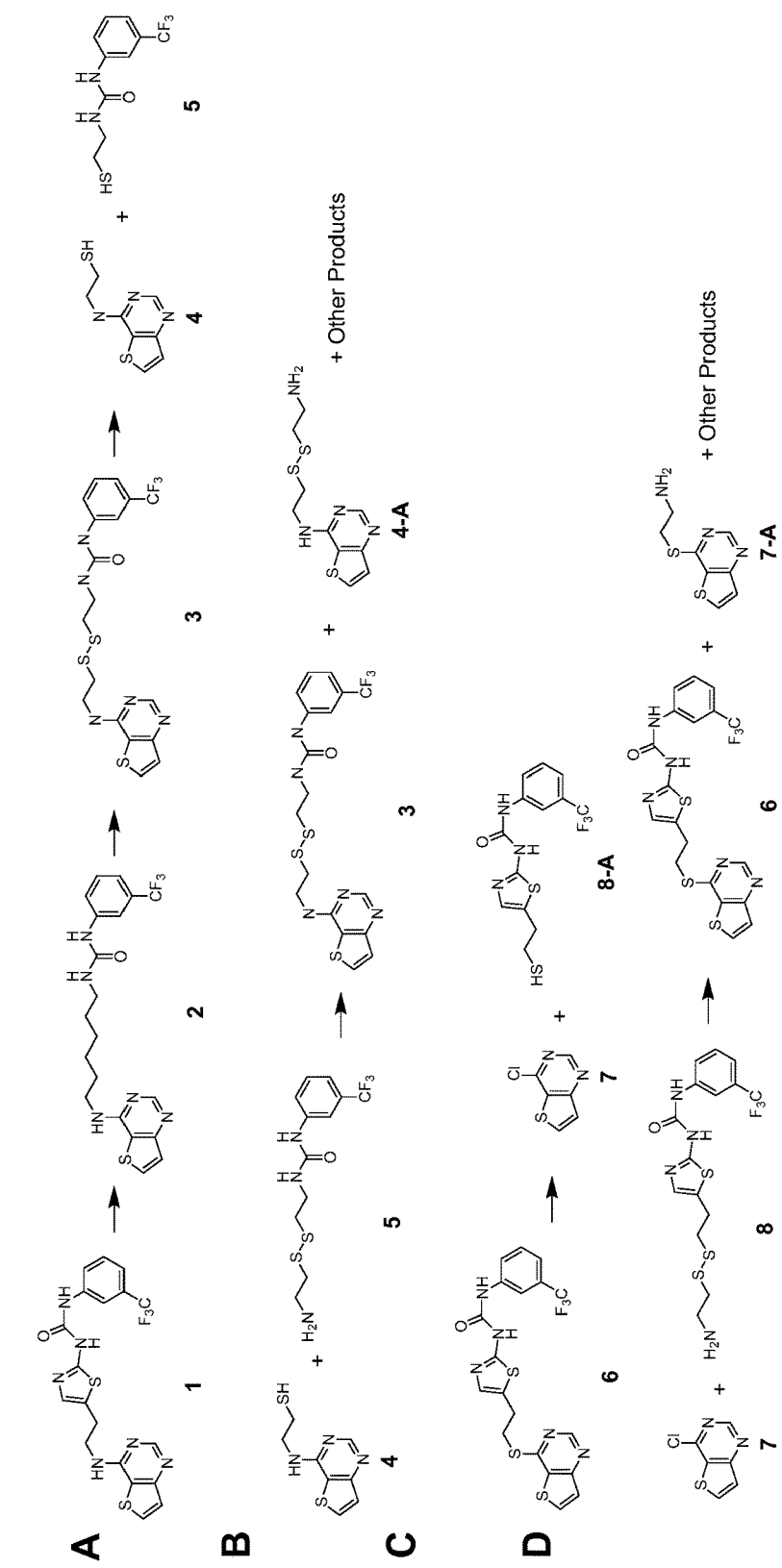
FIG. 2 illustrates some examples of ligand deconstruction (A,C) and fragment assembly chemistries (B,D). (A) Compound 1 and derivatives thereof, and fragments and derivatives thereof (B) Disulfide chemistry connects a thiol bait and a disulfide library fragment under conditions permissive to thiol-disulfide exchange. (C) Compound 6 can be deconstructed into Compound 7 and Compound 8. (D) Thioether chemistry joins a leaving group-containing bait through reaction with the thiolate anion of the reduced library fragment.
Figure 3A:
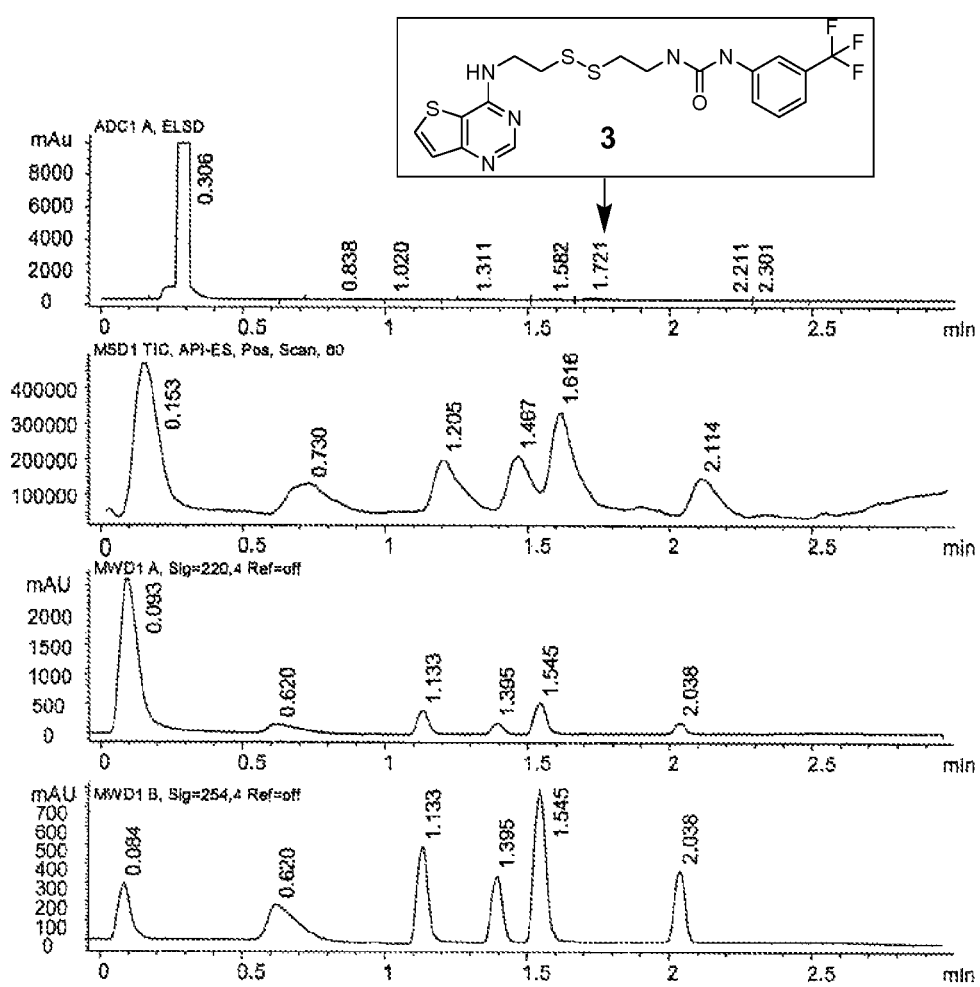
FIG. 3 shows LCMS analysis of fragment assembly reaction mixtures in the absence of target. In each of (A) and (B), parameters in the four panels are measured simultaneously and correspond to (top to bottom) evaporative light scattering detection (ELSD), total ion count (mass), UV absorption at 220 nm, and UV absorption at 254 nm. (A) Representative example of Compound 4 and Compound 5 disulfide product mixture with product Compound 3. Structure and arrow indicates assembled molecule Compound 3. (B) Thioether product mixture of Compound 7 and Compound 8. Structure and arrow indicates assembled molecule Compound 6.

As a proof-of-concept study, the Aurora A kinase ("Aurora A") and the inhibitor Compound 1 were evaluated. Aurora kinases play essential roles in mitosis and have received significant attention as oncology targets. (Carvajal, R. D., et al., *Clinical Cancer Research* 12, 6869-6875 (2006); Keen, N. & Taylor, S., *Nat. Rev. Cancer* 4, 927-936 (2004).) Compound 1 can be deconstructed into two separate pharmacophores connected by a flexible linker (Compound 2, FIG. 2), and this linker can be replaced with a disulfide-containing linker (Compound 3, FIG. 2) while maintaining sufficient activity to be detected in an enzymatic kinase reaction (Table 1). Compound 3 can be readily assembled from the purine mimetic fragment (Compound 4) and the right-side fragment (Compound 5) using disulfide chemistry (FIG. 2B). The assembly reaction was conducted at 1 mM fragment concentration in 90% DMSO to reach equilibrium quickly and then diluted to low μM concentration (2% DMSO) for screening. The reaction mixture had an IC50 of 5.3 μM, while the individual fragments Compound 4 and Compound 5 had IC50 values of 24 μM and 30 μM, respectively (Table 1). When Compound 4 was reacted with cystamine instead of Compound 5, the IC50 of the resulting reaction mixture was 39 μM, suggesting that the 5.3 μM IC50 of the assembled reaction mixture can be attributed to the presence of Compound 3. The presence of Compound 3 in the disulfide assembly reaction mixture was confirmed by LCMS analysis (FIG. 3A). IC50 values were calculated relative to the concentration of fragment molecule present in the kinase reaction.

TABLE 1

| Compound | Structure | IC50 (µM) |
|---|---|---|
| 4 | thieno[3,2-d]pyrimidine with N-CH2CH2-SH at 4-position | 24 |
| Cystamine | H2N-CH2CH2-S-S-CH2CH2-NH2 | 55 |
| 5 | H2N-CH2CH2-S-S-CH2CH2-NH-C(=O)-NH-(3-trifluoromethylphenyl) | 30 |
| 4 + Cystamine | Multiple products | 39 |
| 4 + 5 | Multiple products including Compound 3 | 5.3 |
| 3 | thieno[3,2-d]pyrimidin-4-yl-NH-CH2CH2-S-S-CH2CH2-NH-C(=O)-NH-(3-trifluoromethylphenyl) | 1.6 |

Figure 3B:
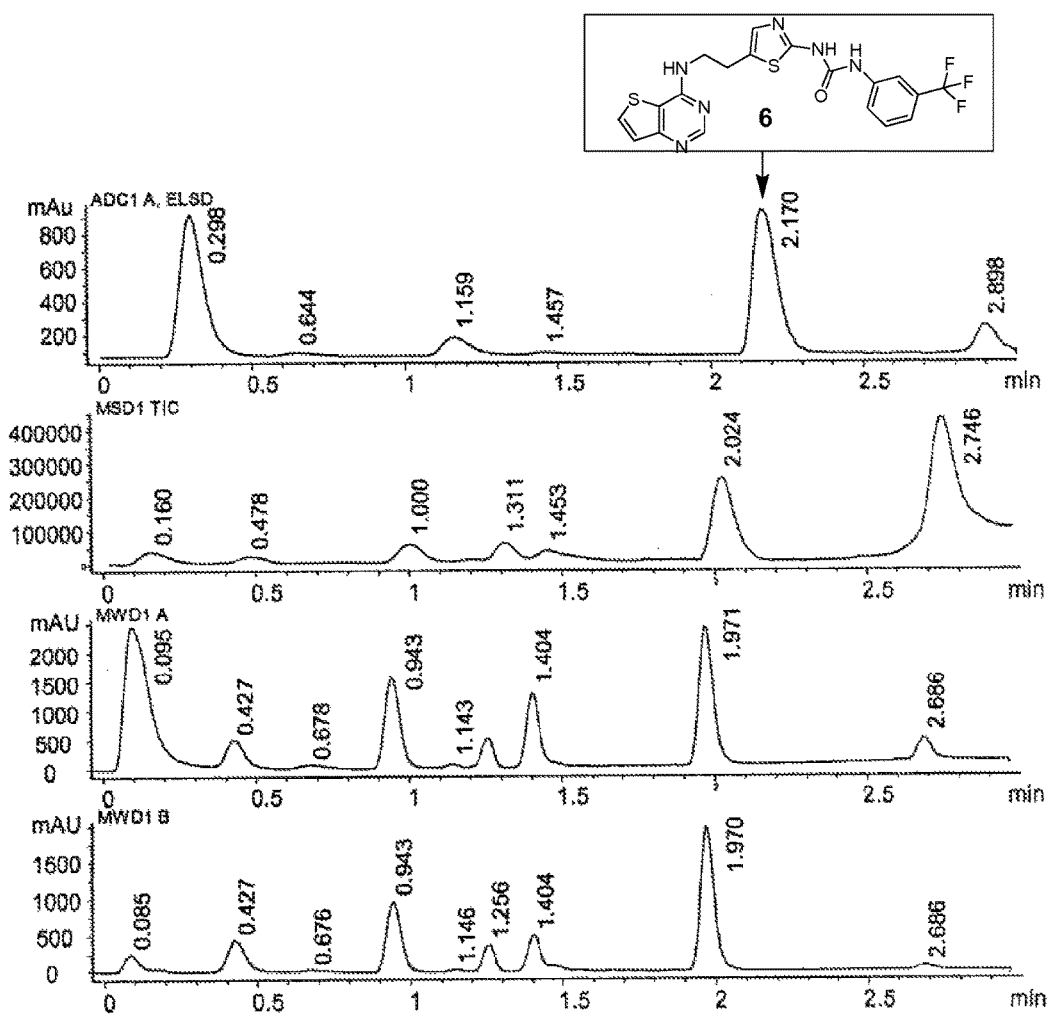
Figure 4:
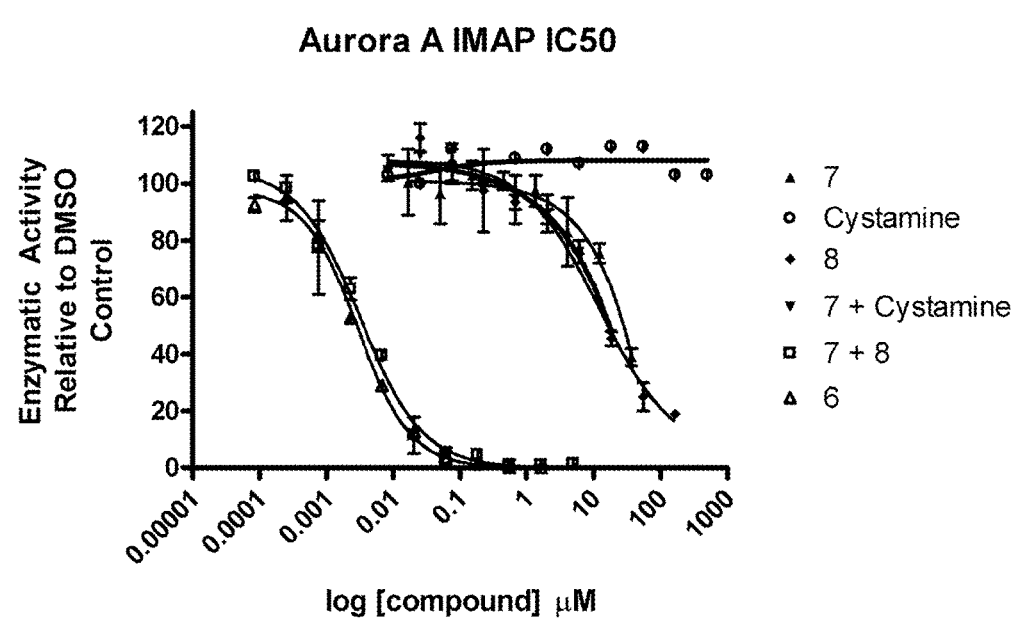
FIG. 4 shows representative data from an activity assay for test ligands/mixtures (assembled by thioether chemistry) against Aurora A. Corresponding structures and $IC_{50}$ values are shown in Table 2.

Similar results can be achieved using thioether chemistry (FIG. 2 and Table 2). Aurora A inhibitor Compound 6 can be assembled from Compound 7 and Compound 8 (FIGS. 2C and 2D), which have 1050 values of 34 µM and 10 µM, respectively. The product mixture (7+8) has an IC50 of 9 nM, which is less than two-fold above the 5 nM IC50 for purified Compound 6 (Table 2 and FIG. 4). Since the control reaction consisting of Compound 7 and cystamine has an IC50 of 17.7 µM, the potent inhibition by the reaction mixture can be attributed to the presence of Compound 6. The presence of Compound 6 in the thioether assembly reaction was confirmed by LCMS analysis (FIG. 3B). Table 2 shows the IC50 values of bait, test fragment, and thioether-assembled test ligands tested in the Aurora A kinase biochemical assay. IC50 values were calculated relative to the concentration of fragment molecule present in the kinase reaction. IC50 curves are shown in FIG. 4.

TABLE 2

| Compound | Structure | IC50 (uM) |
|---|---|---|
| 7 | 4-chlorothieno[3,2-d]pyrimidine | 28 |
| Cystamine | H2N-CH2CH2-S-S-CH2CH2-NH2 | >500 |
| 8 | H2N-CH2CH2-S-S-CH2CH2-(thiazol-5-yl)-2-NH-C(=O)-NH-(3-trifluoromethylphenyl) | 12.2 |
| 7 + Cystamine | Multiple products | 17.7 |
| 7 + 8 | Multiple products including Compound 6 | 0.009 |

TABLE 2-continued

| Compound | Structure | IC50 (uM) |
|---|---|---|
| 6 | 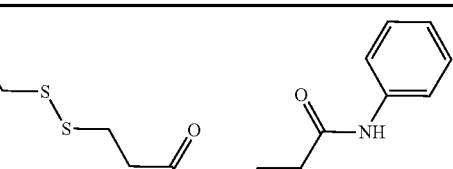 | 0.005 |

Figure 5:
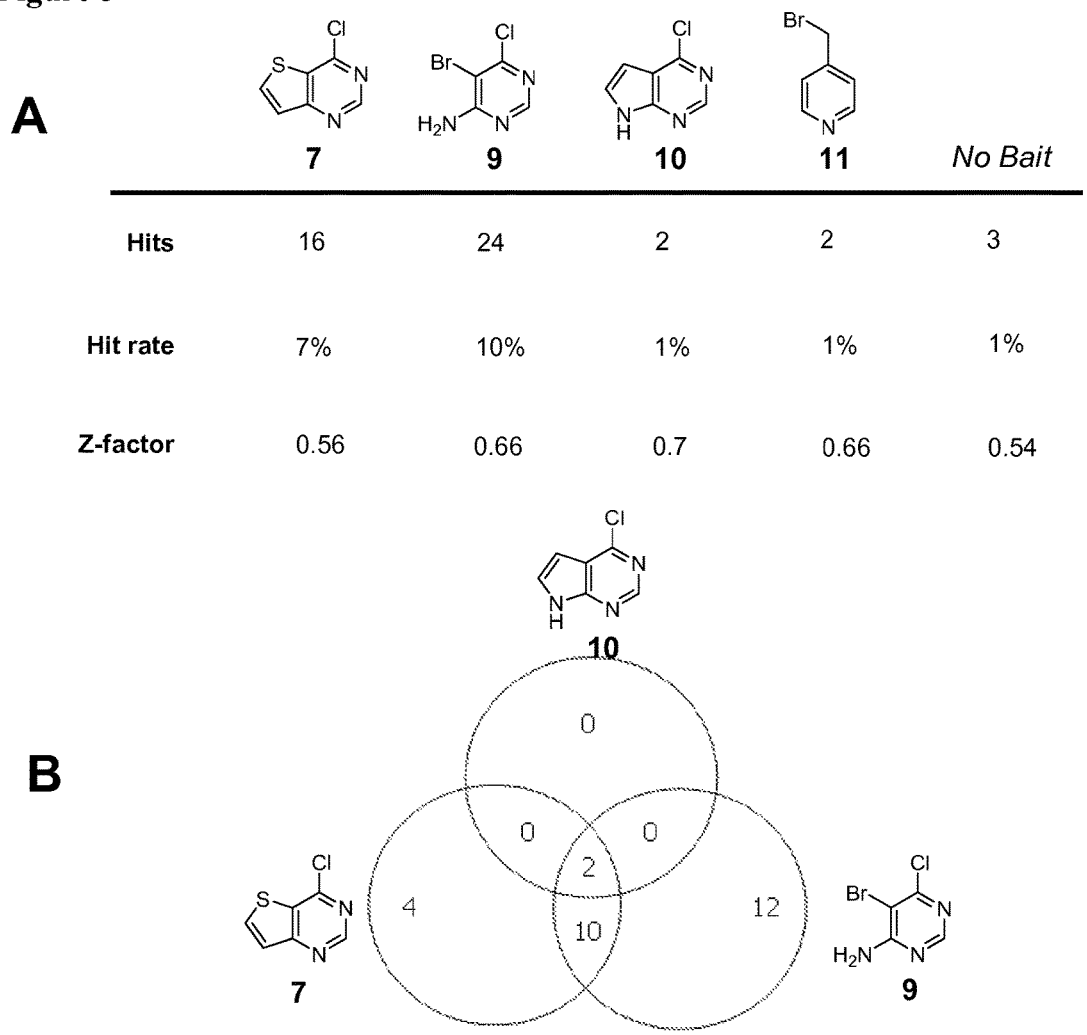
FIG. 5 shows a summary of data from a series of thioether test ligand library screens. (A) Statistics from library screens using as bait fragments three different purine mimetics and the control Compound 11. Hits were defined as fragment reactions with greater than 50% inhibition of Aurora A activity. Two hundred forty (240) fragment reactions were tested at 5 µM each in single-point format, where 5 µM refers to the concentration of fragment molecule present in each reaction. (B) Venn diagram of hits shown in panel A. Hits are grouped by the purine mimetic bait used for each screen, and numbers indicate hits in which the test moieties of the test ligands are unique and those in which test moieties are shared with other hits (intersections).

In order to identify novel Aurora A inhibitors, a test fragment library consisting of 230 compounds was screened in combination with three different purine mimetic bait fragments and one control bait fragment (using thioether chemistry) against Aurora A (FIG. 5). As a control for bait-independent activity, the test fragment library was also screened in the absence of purine mimetic bait fragments ("No Bait," FIG. 5). Fragment reactions were tested in single-point format at a concentration of 5 µM, which is significantly lower than the IC50 values for each of the purine mimetic bait fragment and cystamine control reactions. Screening the test fragment library at this concentration allowed for the detection of synergy between the bait fragment and test fragment molecules since bait fragment alone would not be present at a high enough concentration to significantly reduce Aurora A enzymatic activity.

Hits were defined as fragment reactions with greater than or equal to 50% inhibition of enzymatic activity. The hit rate for each of the screens ranged from 1%-10%. Compound 9 yielded the greatest number of hits—24 in all—while Compound 10 and Compound 11 yielded the least. The Z-factor, a statistic that describes the degree of variability of a screening assay, was calculated for each of the test fragment library screens. Each screen yielded a Z-factor greater than 0.5, above which an assay is considered to be sufficiently robust for high-throughput screening. Of the 28 different test fragments identified as hits, ten fragments were identified in both the Compound 7 and Compound 9 screens, and two fragments were identified in each of the three screens (FIG. 5). Follow-up IC50 reactions were conducted on each of the hits to confirm inhibitory activity against Aurora A. While most of the hits with the three purine mimetics were confirmed, the two hits with Compound 11 were false positives and could not be confirmed. This illustrates that using a bait containing a functional purine mimetic increases the hit rate, as would be expected for a classical kinase inhibitor. Moreover, the most generic purine mimetic, Compound 9, yielded the highest number of hits and also identified most of the hits that were obtained with the two other purine mimetics. This could be attributed to the more promiscuous binding properties of Compound 9, which may encompass the binding modes of the two other purine mimetics. This illustrates how a structurally simple bait fragment can be used to gain wider coverage of the relevant chemical space and thereby reduce the number of screens that may be necessary.

The IC50 values of the thioether assembly mixtures for each of the novel fragment molecules identified in combination with Compound 7 ranged from 0.4 to 2.8 µM (Table 3). Compound mixture "7+8" is shown as a reference for the Aurora A inhibitor Compound 6. Table 3 shows IC50 values of select fragment reactions identified in the Aurora A biochemical assay fragment library screen using bait Compound 7, which is a weak inhibitor of Aurora A kinase and is presumed to occupy the purine pocket. IC50 values were calculated relative to the concentration of fragment molecule present in the kinase reaction.

TABLE 3

| Hit Structure | Combined with Compound 7 | Assembled IC50 (µM) |
|---|---|---|
| 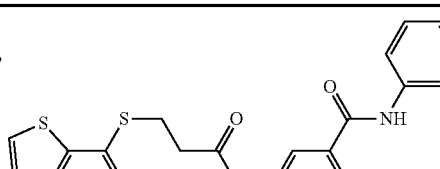 12 | 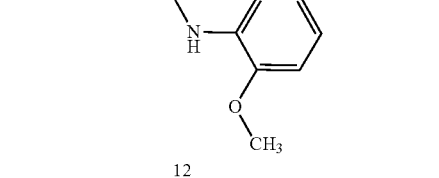 24 | 0.4 |
| 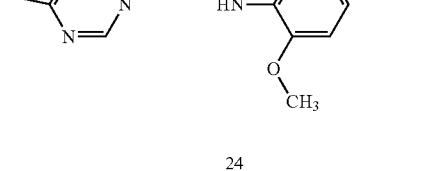 | | 1.7 |

TABLE 3-continued

| Hit Structure | Combined with Compound 7 | Assembled IC50 (μM) |
|---|---|---|
| 13 | 25 | 2.8 |
| 14 | 26 | 0.012 |

The screen can also be conducted in the opposite direction using a newly identified fragment as a bait for screening a purine mimetic library. To illustrate this, hit compounds 8, 12, and 14 were screened in combination with a panel of purine mimetic baits against Aurora A using thioether chemistry. The $IC_{50}$ values of the most potent purine mimetic bait-fragment combinations ranged from 0.067 to 0.65 μM (Table 4). The $IC_{50}$ values of the resynthesized molecules ranged from 0.12 to 0.4 μM. Table 4 shows the $IC_{50}$ values of select fragment-bait pairings based on purine mimetic back-screen in the Aurora A kinase biochemical assay. $IC_{50}$ values were calculated relative to the concentration of fragment molecule present in the kinase reaction. In addition to inhibiting the activity of Aurora A kinase in enzyme assays, compounds 15 and 18 also inhibit Aurora A activity in cell based assays with $EC_{50}$ values of 1 and 0.05 μM, respectively. Crystallography data confirm that these molecules bind to different conformations of the enzyme and use different footprints to access the adaptive site of Aurora A. This simple example illustrates how applying the present fragment-based ligand evolution methods to a limited fragment collection can rapidly rediscover a known inhibitor (6), and evolve from a single starting fragment to active, structurally distinct compounds (15-18).

TABLE 4

| New Bait | Purine Mimetic | Assembled IC50 (μM) | Resynthesized Hit/Analog | Resynthesized Hit/Analog IC50 (μM) |
|---|---|---|---|---|
| 12 | 9 | 0.65 | 15 | 0.12 |

TABLE 4-continued

| New Bait | Purine Mimetic | Assembled IC50 (μM) | Resynthesized Hit/Analog | Resynthesized Hit/Analog IC50 (μM) |
|---|---|---|---|---|
| 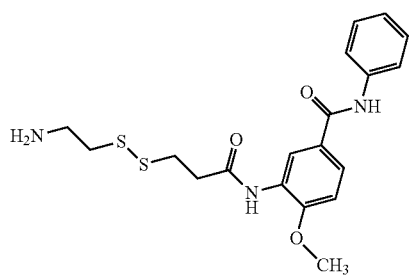 [SMILES: COc1ccc(C(=O)Nc2ccccc2)cc1NC(=O)CCSSCCN] 12 | 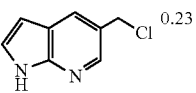 19 | 0.23 | 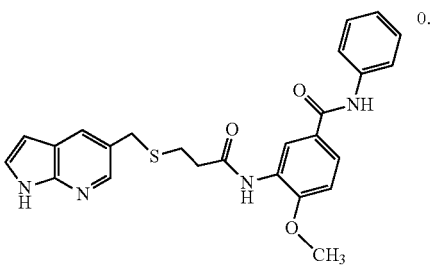 16 | 0.15 |
| 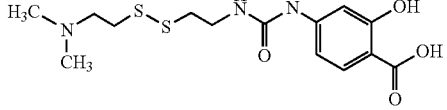 14 | 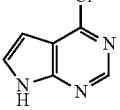 10 | 0.067 | 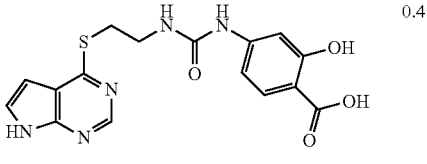 17 | 0.4 |
| 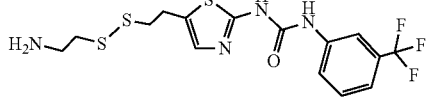 8 | 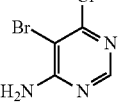 9 | 0.01 | 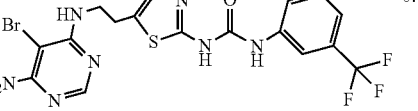 18 | 0.005 |

Table 5 discloses the enzymatic activity of select compounds against Aurora A. Notable $IC_{50}$ values for two disclosed mixtures are 1.8 μM and 4 μM, while some single molecules showed comparatively low potency. Table 5 provides $IC_{50}$ values of bait, fragment, and disulfide-assembled molecules tested in the Aurora A kinase biochemical assay. $IC_{50}$ values were calculated relative to the concentration of fragment molecule present in the kinase reaction.

TABLE 5

| Compound | Structure | $IC_{50}$ μM |
|---|---|---|
| 4 | 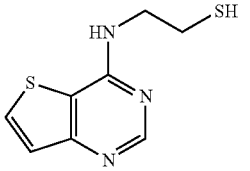 [SMILES: SCCNc1ncnc2ccsc12] | 24 |
| 20 | 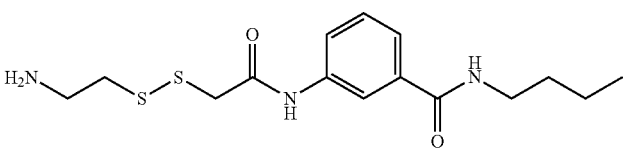 [SMILES: CCCCNC(=O)c1cccc(NC(=O)CSSCCN)c1] | >50 |

TABLE 5-continued

| Compound | Structure | IC$_{50}$ µM |
|---|---|---|
| 4 + 20 | 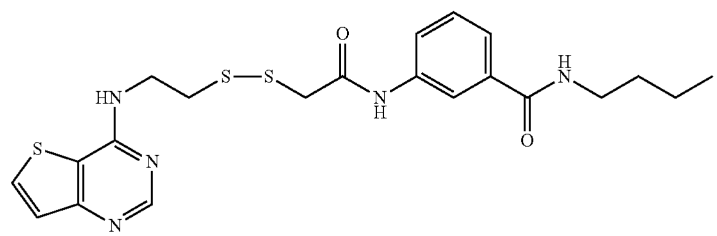 [SMILES: CCCCNC(=O)c1cccc(NC(=O)CSSCCNc2ncnc3ccsc23)c1] | 1.8 |
| 21 | 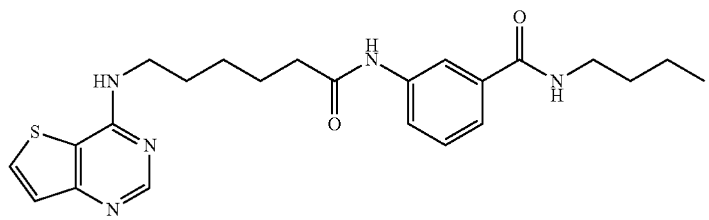 [SMILES: CCCCNC(=O)c1cccc(NC(=O)CCCCCNc2ncnc3ccsc23)c1] | 4.1 |
| 22 | 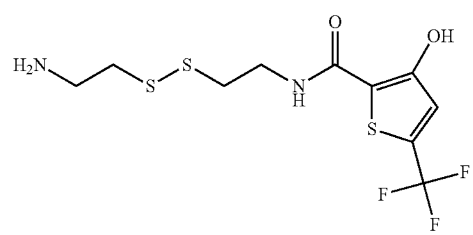 [SMILES: NCCSSCCNC(=O)c1sc(C(F)(F)F)cc1O] | >50 |
| 4 + 22 | 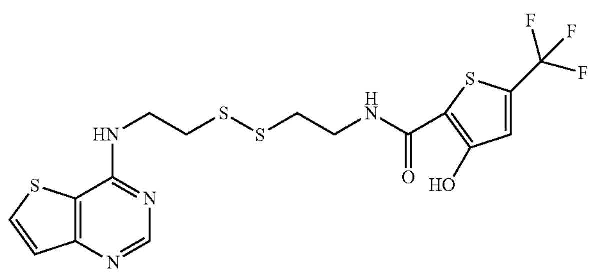 [SMILES: O=C(NCCSSCCNc1ncnc2ccsc12)c1sc(C(F)(F)F)cc1O] | 4.0 |
| 23 | 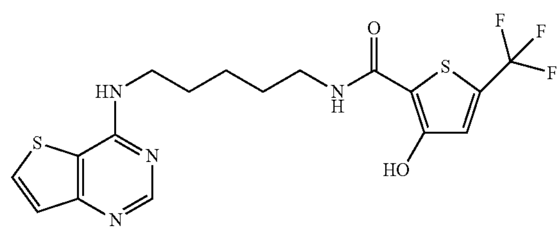 [SMILES: O=C(NCCCCCNc1ncnc2ccsc12)c1sc(C(F)(F)F)cc1O] | 11.5 |

Protein: dynamic disulfide library incubation for GPC-LC/MS Detection. Solutions of humanized mouse Aurora A (amino acids 107-403) expressed in E. coli as previously described (Elling et al., Protein Expr Purif, 2007, pp. 139-146) are thawed and used immediately before incubation with the dynamic disulfide libraries and are adjusted to a final concentration of 5 µM in the assay buffer 50 mM TRIS pH 7.5 and 200 mM NaCl. The "bait" and disulfide fragment library members are stored in DMSO stock solutions. The final concentration in the incubation mixtures is adjusted to 250 µM for the bait and 10 µM for each library component. Control samples are prepared identically, without the addition of protein. Incubations and separation steps are performed in a 96-well format. A measure of 48 µL of the protein solution are added into V-bottom 96-well plates containing 1 µL of 12.5 mM bait and 1 µL of a mixture of 0.5 mM each disulfide library member. Disulfide library test fragments are pooled into 5 to 10 compounds per well. The library members have an atomic mass difference of at least 0.1 Da per well to ensure unambiguous detection by mass spectrometry. The plates are sealed using a PlateLoc plate sealer (Velocity 11, Menlo Park, Calif.) and the reaction is gently shaken at RT for 2 hr. Alternatively, the bait and disulfide library components are mixed and allowed to establish equilibrium in the assay buffer for 2 hr, followed by the addition of protein at a final concentration of 5 µM. The protein:library solution is incubated for 30 minutes before separation. All incubations are halted by separating the protein:ligand complexes from small-molecular weight compounds by gel permeation chromatography (GPC) or size exclusion chromatography (SEC).

Protein:ligand complex isolation by SEC. For simultaneous GPC in a 96-well format, MiniSpin P6 96-well spin plates (The Nest Group, Southborough, Mass.) was used. The plates were hydrated with 300 μL of 100 mM ammonium acetate for at least 30 min. Directly before using the GPC plates, the hydrating buffer was removed by centrifuging the plates at 500×g at 4° C. for 3 min. Next, the GPC plates were washed with an additional 300 μL of 100 mM ammonium acetate by centrifugation 500×g at 4° C. for 3 min. Aliquots of 30 [L of the protein:library mixture were carefully transferred to a V-bottom 96-well plate containing pinholes in the bottom, which allowed the mixture to proceed through the pinhole only when centrifuged and not under normal gravity. The pinhole plate containing the protein:library solution was placed on top of the conditioned 96-well MiniSpin P6 plate. These two plates were then placed on top of a 96-well V-bottom collection plate, thus making a three-layer plate isolation system. To isolate the protein:test ligand complex from non-binding test ligands the entire three-layer GPC plate system was centrifuged for 3 min at 500×g at 4° C. The eluates in the 96-well collection plate were analyzed by LC/MS to identify protein:test ligand complexes.

Liquid Chromatography/Mass Spectrometry. Utilizing an HTS PAL autosampler (LEAP Technologies, Carrboro, N.C.), each sample was injected into an electrospray LC/MS system. For the rapid determination of potential small-molecular weight binding test ligands an electrospray-liquid chromatography-time-of-flight mass spectrometer system was used, composed of a 1525 HPLC pump (Waters Corporation, Milford, Mass.) and a LCT classic TOF mass spectrometer (Waters Corporation, Milford, Mass.). The chromatography was performed on two protein microtraps (Michrom Bioresources, Auburn, Calif.) in series using a gradient with initial conditions of 95% water, 0.1% formic acid (HPLC buffer A) and 5% acetonitrile, 0.1% formic acid (HPLC buffer B) for one minute, stepped to 50% each HPLC buffer A and B from 1 to 2 min, stepped to 20% HPLC buffer A and 80% HPLC buffer B from 2 to 2.5 min followed by the initial conditions from 2.5 to 3.0 min, all steps were at a flow rate of 600 μL/min. The HPLC eluate was introduced into the TOF mass spectrometer at a flow rate of 30 μL/min by introducing a split into the flow path directly before the electrospray ion source. The MS source was operated at a desolvation temperature of 300° C., sample cone voltage of 45 V, TOF capillary voltage of 3.2 kV and was scanned in continuum mode from 350 to 1800 amu. The first 1.4 minutes of the HPLC solvent was diverted to waste and data was collected from 1.4 to 3.0 min. For the detailed analysis of the dynamic combinatorial library before protein incubation an LCQ Advantage ion trap mass spectrometer (Thermo Finnigan, San Jose, Calif.) was used. Samples were loaded and desalted onto a small molecule nanotrap (Michrom-Bioresources, Auburn, Calif.) using a HTC PAL autosampler (LEAP Technologies, Carrboro, N.C.) followed by gradient elution through a 3 μm 200 Å Magic C18AQ 0.2×50 mm HPLC column (Michrom Bioresources) and ionized using an ADVANCE source (Michrom Bioresources). The gradient consisted of initial conditions at 95% HPLC buffer A and 5% HPLC buffer B followed by a ramping HPLC buffer B to 80% over 15 min, maintaining 80% HPLC buffer B to 15.5 min and then lowering HPLC buffer B back to the initial conditions at 16 min and maintaining the initial conditions through 20 min, with all gradient steps run at approximately 3 μL/min through the HPLC column and into the ADVANCE MS source. The mass spectrometer source was operated at 1.5 kV with the heated capillary at 180° C., capillary voltage of 18V, tube lens offset of 31.5V and sheath nitrogen gas flow set to 20. The ion trap mass spectrometer was operated in positive ion mode from 200 to 800 amu.

Figure 6:
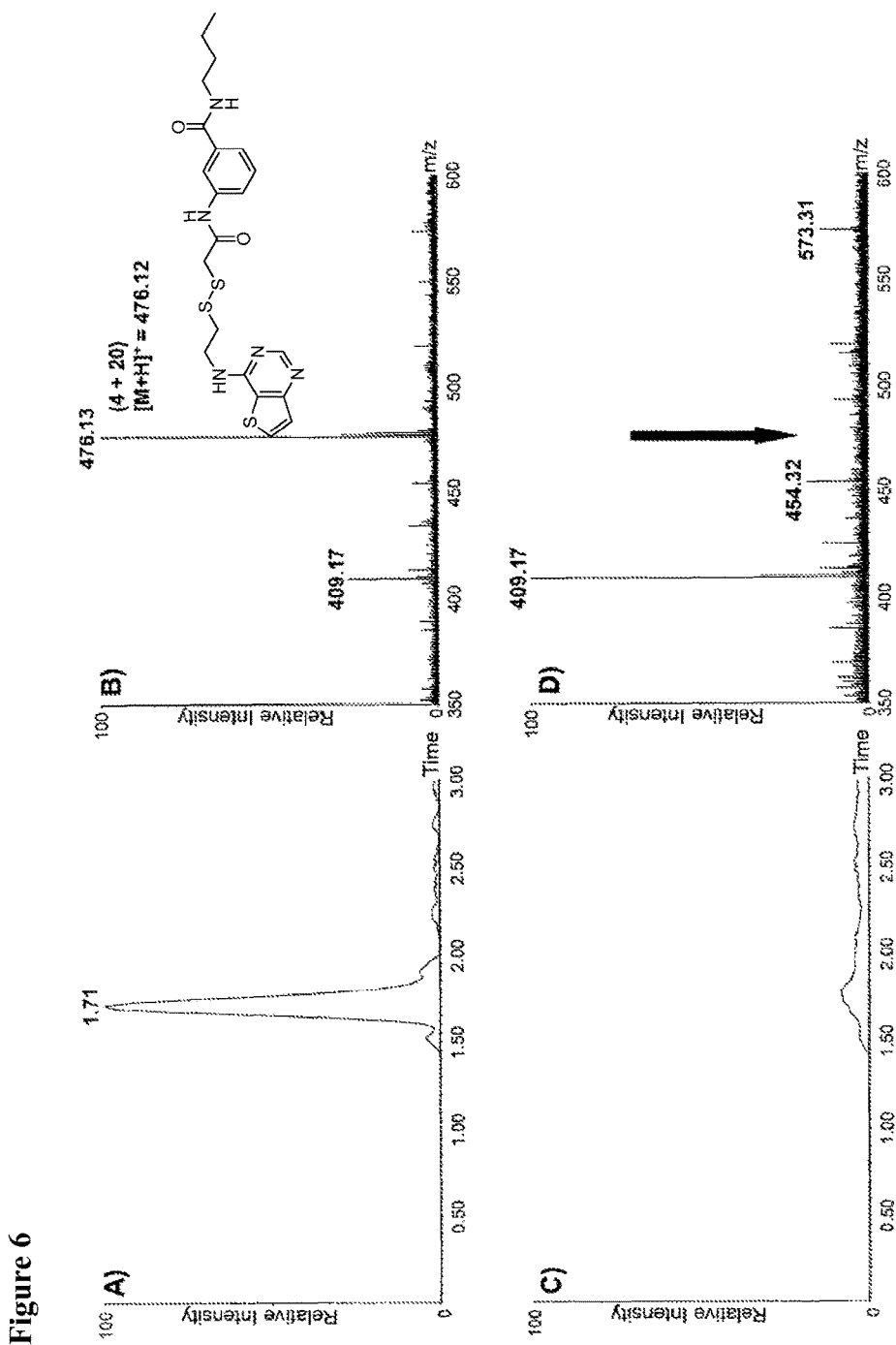
FIG. 6A shows an LC/MS trace of a test ligand (from a dynamic disulfide library) captured by Aurora A kinase after isolation by rapid GPC. The dynamic disulfide library originally contained the bait Compound 4 and 10 disulfide components.
FIG. 6B shows, a mass spectrum identifying the disulfide library test ligand at m/z 476, corresponding to a disulfide test ligand assembled from the bait Compound 4 and the library member Compound 20.
FIG. 6C shows an LC/MS trace of the GPC eluate from the control sample.
FIG. 6D shows a mass spectrum of the control sample demonstrating no detectable levels (as indicated by the arrow) of the hit previously identified without the presence of Aurora A kinase.

FIG. 6 shows at (A) an LC/MS trace of a dynamic disulfide library member captured by Aurora A kinase after isolation by rapid GPC. The dynamic disulfide library originally contained the bait Compound 4 and 10 disulfide components (not shown). The mass spectrum at (B) identified a component at m/z 476 that is a disulfide composed of the bait Compound 4 and the library member Compound 20, as shown. This trace displays the selectivity of Aurora A kinase for this disulfide combination. (The peak at m/z 409 is due to chemical noise.) For comparison purposes, the identical dynamic sulfide library in the absence of Aurora A kinase was eluted from by rapid GPC and the corresponding LC/MS trace is shown at (C). The mass spectrum of the control sample at (D) demonstrates no detectable levels (as indicated by the arrow) of the hit at m/z 476 previously identified in (B).

Figure 7:
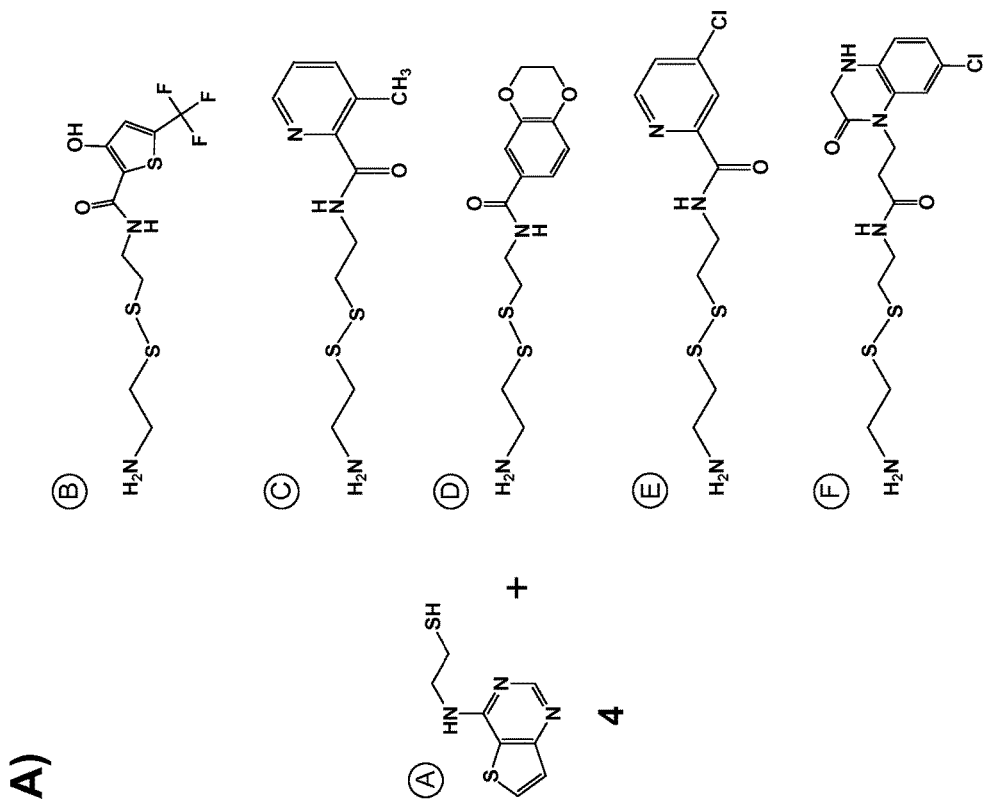
FIG. 7A shows an example of initial reactants in a disulfide dynamic library consisting of the bait Compound 4 and a pool of five disulfide compounds.
FIG. 7B shows an LC/MS trace of the equilibrated disulfide dynamic library products before incubation with Aurora A kinase.
FIG. 7C shows an LC/MS trace of a dynamic disulfide library member captured by Aurora A kinase after isolation by rapid GPC.
Figure 7:
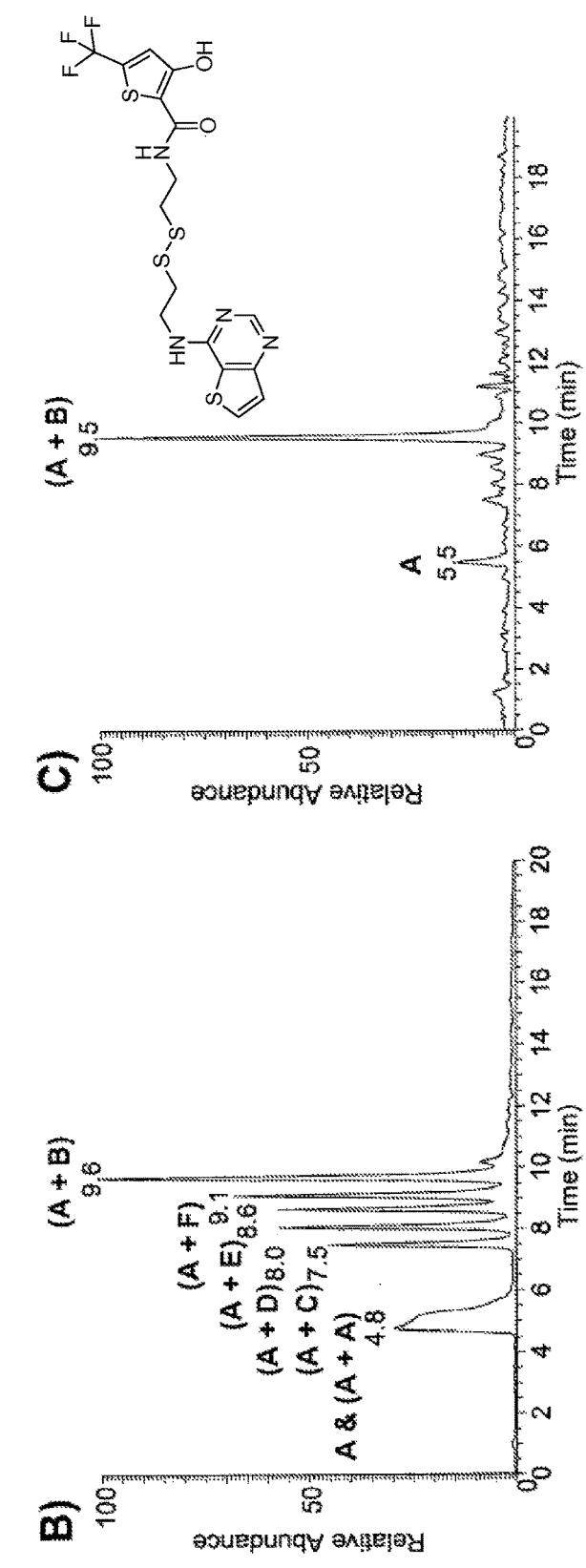

FIG. 7 provides an example of initial reactants in a disulfide dynamic library consisting of the bait Compound 4 and a pool of five disulfide compounds (see (A)). The LC/MS trace at (B) of the equilibrated disulfide dynamic library products before incubation with Aurora A kinase shows the results of the binding of the bait with each of the test fragments (B, C, D, E, and F). The LC/MS trace at (C) shows a dynamic disulfide library member captured by Aurora A kinase after isolation by rapid GPC. The test ligand containing the bait, "A," and disulfide member, "B" (Compound 4 +22), is clearly selected from the complex mixture.

Figure 9:
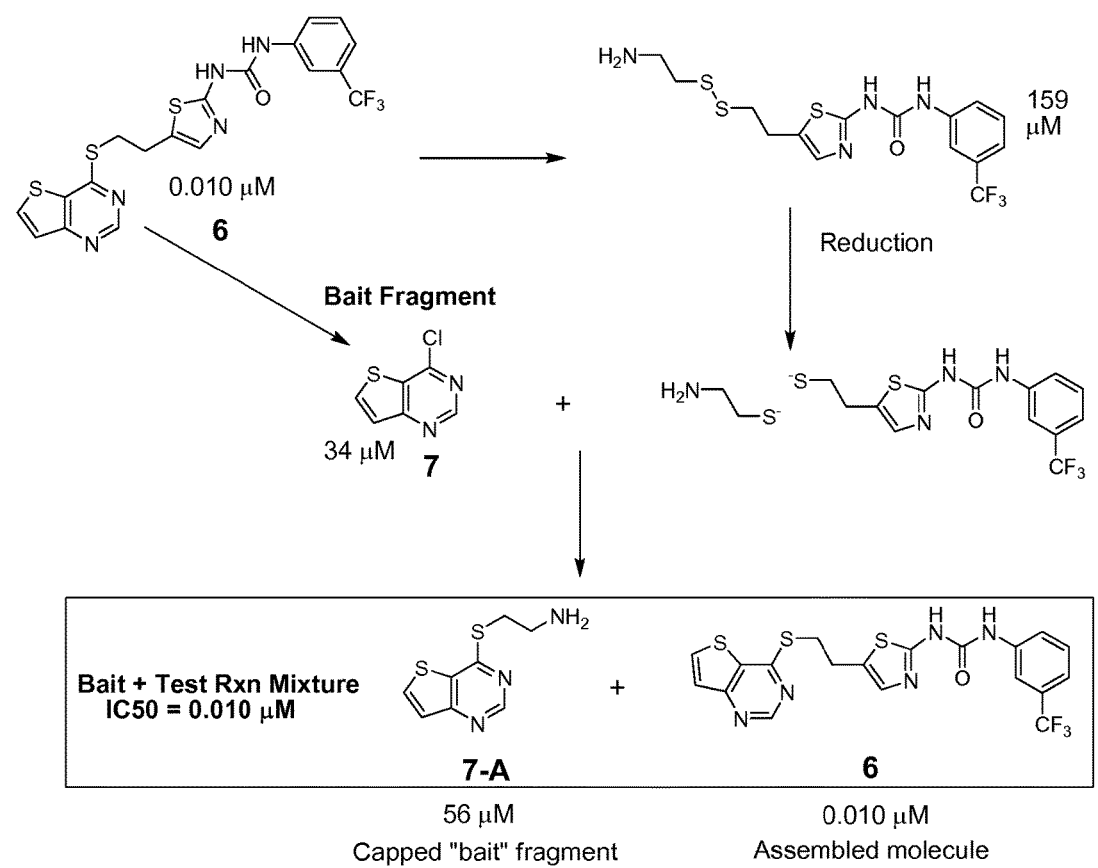
FIG. 9 summarizes IMAP assay results for a reconstructed Aurora inhibitor. Results are shown for a known inhibitor (Compound 6), a portion of the known inhibitor (Compound 7) having a reactive chloro group, and a corresponding disulfide analog of the remainder of the inhibitor (Compound 8). The disulfide fragment was subjected to reducing conditions and reacted with Compound 7; results are also shown for the resulting reaction mixture, as well as for the respective purified components of the mixture (Compound 7A and Compound 6).
Figure 10:
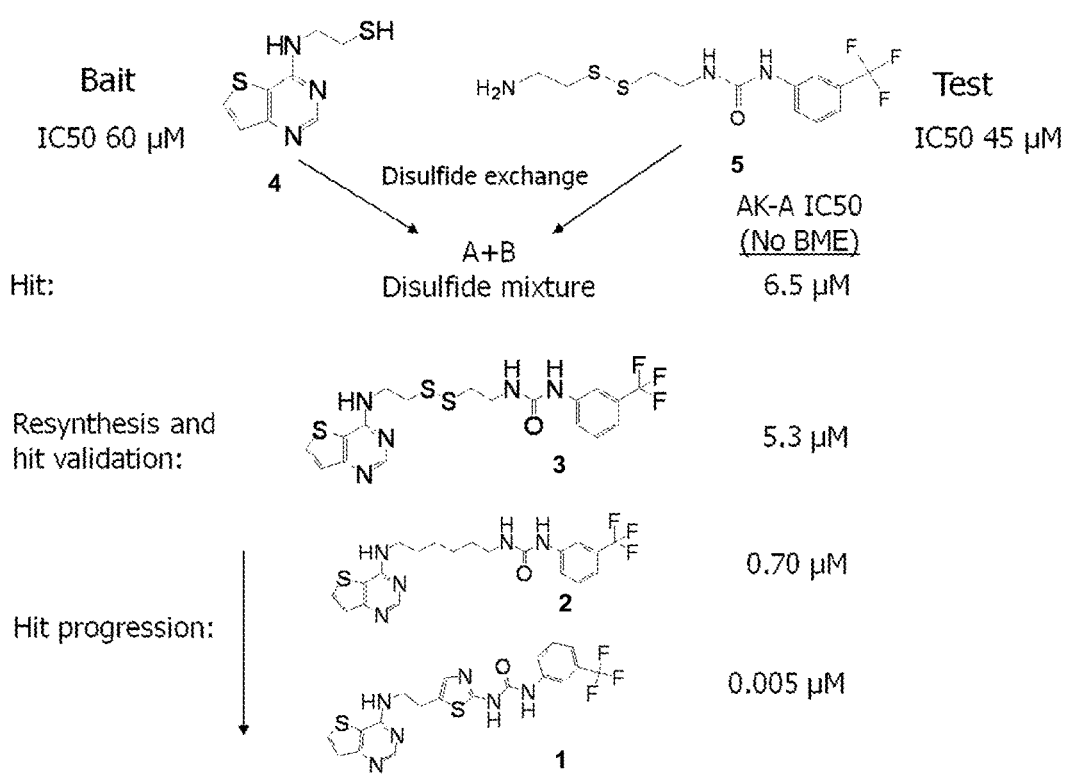
FIG. 10 summarizes IMAP assay results for a reconstructed analog of the Aurora inhibitor shown in FIG. 9. Compound 1 corresponds to the analog. A sulfhydryl derivative (Compound 4) of a portion of the analog was reacted with a disulfide derivative of another portion of the molecule (Compound 5) by disulfide exchange chemistry to produce the mixture A+B. The $IC_{50}$ of the mixture met the threshold of being considered a hit in the assay. $IC_{50}$ values are also provided for the corresponding purified disulfide ligand (Compound 3), as well as the derivative where the linker containing the disulfide is replaced with an alkyl linker (Compound 2).

FIGS. 9 and 10 show a summary of results obtained from reconstructing inhibitors of Aurora A using thioether and disulfide chemistries, respectively.

Example 9

Compound 26

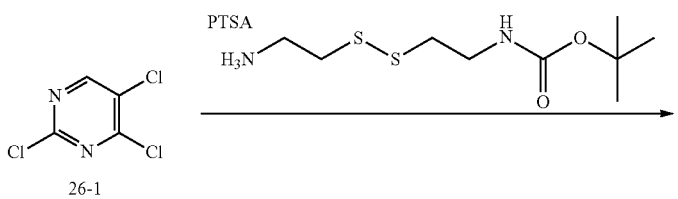

26-1

-continued

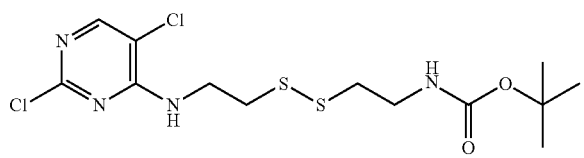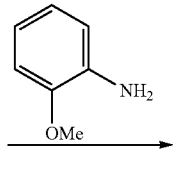

26-2

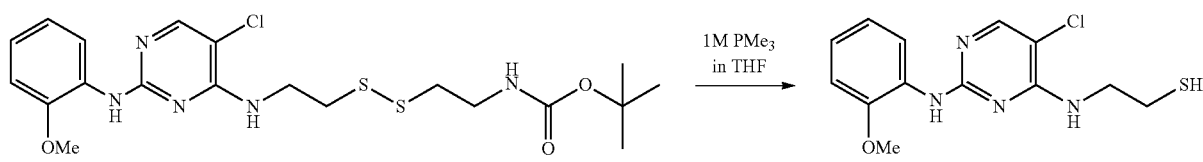

To a solution of 2,4,5-trichloro-pyrimidine 26-1 (0.200 g, 1.1 mmol) and DIEA (0.538 mL, 3.3 mmol) in dioxane was added the para-toluenesulfonic acid (PTSA) salt of Boc-cysteamine (0.508 g, 1.2 mmol). After heating at 70° C. for 16 hr, the reaction mixture was cooled and concentrated to give the desired disulfide 26-2, which was used without further purification. MS (ESI): mass calculated for $C_{13}H_{20}Cl_2N_4O_2S_2$, 399.4; m/z found 343.1 $[M-57]^+$.

To a solution of 26-2 (1.1 mmol) in 2-methoxyethanol was added 2-methoxyaniline (0.136 mL, 1.2 mmol) and 1 M HCl in ethanol (4.4 mL, 4.4 mmol). After heating at 110° C. for 2 hr, the reaction mixture was partitioned between EtOAc (10 mL) and water (10 mL). The organic layer was washed with water (3×5 mL), brine, dried (MgSO$_4$), filtered, and concentrated to give the desired 26-3, which was used without further purification. MS (ESI): mass calculated for $C_{20}H_{28}ClN_5O_3S_2$, 486.1; m/z found 386.1 $[M-100]^+$.

To a solution of 26-3 (1.1 mmol) in THF (2 mL) was added 1 M trimethylphosphine (PMe$_3$) in THF (2 mL). After stirring at RT for 1 h, the reaction was concentrated and the residue was purified by reverse-phase HPLC to provide 26. MS (ESI): mass calculated for $C_{14}H_{16}ClN_3OS$, 309.8; m/z found 311.1 $[M+1]^+$.

Example 10

Compound 27

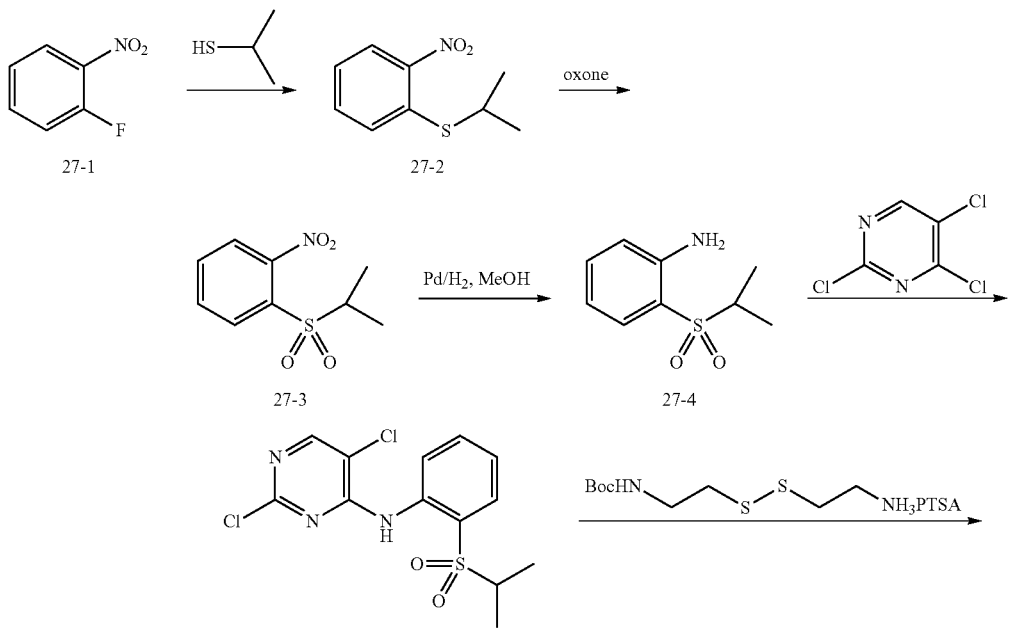

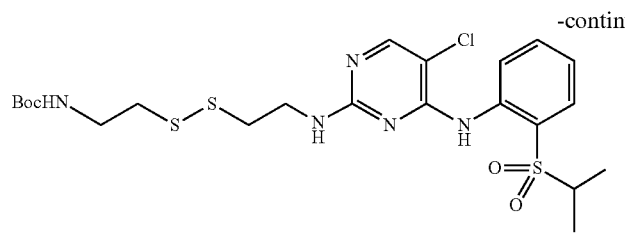

27-6

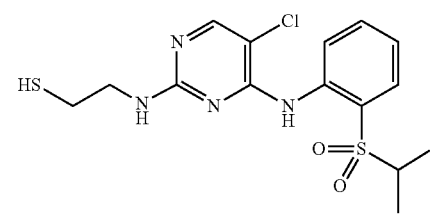

27

To a solution of 27-1 (2 mL, 19 mmol) in DMF (60 mL) was added isopropyl thiol (1.7 mL, 19 mmol) and $K_2CO_3$ (2.9 g, 20.9 mmol). After stirring at 50° C. for 16 hr, the reaction mixture was partitioned between EtOAc (100 mL) and water (100 mL). The organic layer was washed with water (3×50 mL), brine (1×50 mL), dried ($MgSO_4$), filtered, and concentrated to give the desired 27-2, which was used without further purification. MS (ESI): mass calculated for $C_9H_{11}NO_2S$, 197.3; m/z found 156.1 $[M-41]^+$.

To a solution of 27-2 (19 mmol) in MeOH (200 mL) at 0° C. was added a solution of oxone (58.4 g, 95 mmol) in $H_2O$ (200 mL). Upon addition, the reaction solution was warmed to RT and stirred for 16 hr. After removing the MeOH in vacuo, the reaction solution was slowly neutralized with saturated solution of $NaHCO_3$ in $H_2O$. The reaction mixture was partitioned between EtOAc (200 mL) and water (200 mL). The organic layer was washed with water (3×50 mL), brine (1×50 mL), dried ($MgSO_4$), filtered, and concentrated to give the crude compound which was purified by silica gel chromatography (30% EtOAc in hexanes) to provide 27-3. MS (ESI): mass calculated for $C_9H_{11}NO_4S$, 229.3; m/z found 252.1 $[M+23]^+$.

To a solution of 27-3 (19 mmol) in MeOH (50 mL) was added palladium on carbon (Pd/C) (0.3 g). The reaction was stirred under an atmosphere of $H_2$ (balloon) for 3 h, after which more Pd/C (0.3 mg) was added. After stirring for 16 hr, the reaction mixture was filtered over Celite® (diatomaceous earth) and washed with MeOH. Removal of solvent provided 27-4 which was used without further purification. MS (ESI): mass calculated for $C_9H_{13}NO_2S$, 199.3; m/z found 200.1 $[M+1]^+$.

To a solution of 27-4 in DMF at 0° C. was added 60% NaH (2.6 g, 66.8 mmol). After stirring at 0° C. for 1 h, a solution of 2,4,5-trichloro-pyrimidine (1.91 mL g, 16.7 mmol) in DMF (20 mL) was added dropwise. After stirring at 0° C. for 3 hr, the reaction mixture was quenched with a saturated aqueous solution of $NH_4Cl$. The reaction mixture was partitioned between EtOAc (200 mL) and water (200 mL). The organic layer was washed with water (3×50 mL), brine (1×50 mL), dried ($MgSO_4$), filtered, and concentrated to give the crude compound which was purified by silica gel chromatography (20% EtOAc in hexanes) to provide 27-5. MS (ESI): mass calculated for $C_{13}H_{13}Cl_2N_3O_2S$, 346.2; m/z found 346.1 $[M]^+$.

To a solution of 27-5 (0.165 g, 0.5 mmol) in N-methyl-pyrrolidinone (NMP) was added the PTSA salt of Boc-cysteamine (0.222 g, 0.5 mmol) and TEA (0.150 mL, 1.5 mmol). After heating at 110° C. for 2 hr, the reaction mixture was partitioned between EtOAc (10 mL) and water (10 mL). The organic layer was washed with water (3×5 mL), brine, dried ($MgSO_4$), filtered, and concentrated to give the desired 27-6, which was used without further purification. MS (ESI): mass calculated for $C_{22}H_{32}ClN_5O_4S_3$, 562.2; m/z found 562.1 $[M]^+$.

To a solution of 27-6 (0.5 mmol) in THF (2 mL) was added 1 M $PMe_3$ in THF (2 mL). After stirring at RT for 1 hr, the reaction was concentrated and the residue was purified by reverse-phase HPLC to provide 27. MS (ESI): mass calculated for $C_{15}H_{19}ClN_4O_2S_2$, 386.9; m/z found 386.4 $[M]^+$. 1H NMR (400 MHz, METHANOL-D4) d ppm 1.25 (d, J=6.85 Hz, 6 H) 2.66 (s, 2 H) 3.37 (m, 1 H) 3.49 (s, 2 H) 7.52 (s, 1 H) 7.83 (s, 1 H) 7.97 (s, 1 H) 8.15 (s, 1 H) 8.37 (m, 1 H).

Example 11

Compound 28

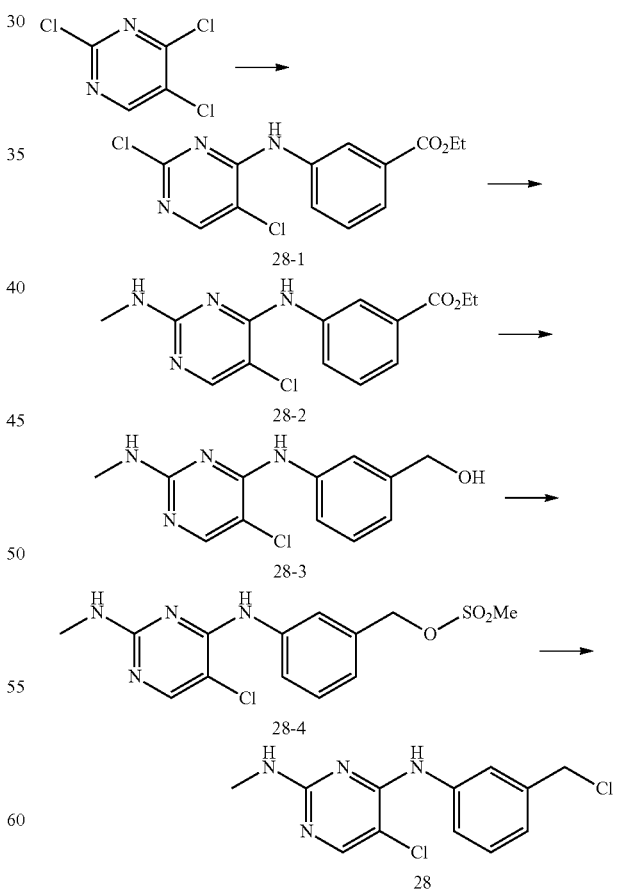

To a solution of 2,4,5-trichloropyrimidine (0.35 mL, 3.05 mmol) in NMP was added ethyl-3-aminobenzoate (0.5 mL, 3.35 mmol) and DIEA (1.1 mL, 6.34 mmol). After heating at 100° C. for 2 hours, the reaction mixture was partitioned between ethyl acetate (150 mL) and water (100 mL). The organic layer was washed with water (2×100 mL) and brine, dried over MgSO$_4$, and concentrated to give the desired 28-1 in 100% yield, which was used without further purification. MS (ESI): mass calcd. for C$_{13}$H$_{11}$Cl$_2$N$_3$O$_2$, 311.0; m/z found 312.1 [M]$^+$.

To a solution of 28-1 (422.2 mg, 1.35 mmol) in 6 mL NMP was added a solution of methylamine (2M/THF, 2.0 mL, 4.0 mmol). The reaction mixture was heated under microwave irradiation at 120° C. for 1 hour. The reaction mixture was partitioned between EtOAc (100 mL) and water (100 mL), and the organic layer washed with water (2×100 mL) and brine. After drying over MgSO$_4$, the organic layer was concentrated to give the desired 28-2 in 72% yield, which was used without further purification. MS (ESI): mass calcd. for C$_{14}$H$_{15}$ClN$_4$O$_2$, 306.1; m/z found 307.3 [M]$^+$.

To a solution of 28-2 (124.5 mg, 0.41 mmol) in THF was slowly added a solution of lithium aluminum hydride (1M/THF, 0.8 mL, 0.8 mmol). After stirring at RT for 1.5 hr, an additional 1.5 mL LAH (1.5 mmol) was added, and after stirring at RT for an additional 1 hr, 1.0 mL LAH (1.0 mmol) was added. After stirring at RT for 1 hr the reaction was quenched by slowly adding 0.13 mL water, then 0.13 mL 15% aq NaOH, then 0.4 mL water. The reaction mixture was stirred at room temperature for 30 min, dried over MgSO$_4$, filtered through Celite, and concentrated to give the desired 28-3, which was used without further purification. MS (ESI): mass calcd. for C$_{12}$H$_{13}$ClN$_4$O, 264.1; m/z found 265.1 [M]$^+$.

To a solution of 28-3 (0.97 mmol) in DCM was added methane sulfonylchloride (0.1 mL, 1.29 mmol) and triethylamine (0.3 mL, 2.15 mmol). After stirring at RT for 1.5 hr, the reaction mixture was partitioned between EtOAc(100 mL) and water (100 mL). The organic layer was washed with water (100 mL) and brine, dried over MgSO$_4$, and concentrated to give the desired 28-4. This material was dissolved in DMF, to which was added LiCl (169 mg, 3.99 mmol). After heating at 50° C. for 1 hr, the reaction mixture was partitioned between EtOAc (100 mL) and water (100 mL). The organic layer was washed with water (2×50 mL) and brine, dried over MgSO$_4$, and concentrated. The resulting residue was purified by silica chromatography to give the desired 28 in 41% yield. MS (ESI): mass calcd. for C$_{12}$H$_{12}$Cl$_2$N$_4$, 282.0; m/z found 283.2 [M]$^+$. 1H NMR (400 MHz, DMSO-D6) δ ppm 2.79 (s, 3 H), 4.77 (s, 2 H), 7.27 (d, 1 H), 7.39 (t, 1 H), 7.63 (d, 1 H), 7.85 (s, 1 H), 8.00 (s, 1H), 8.22 (s, 1 H), 9.87 (s, 1 H).

Example 12

Compound 29

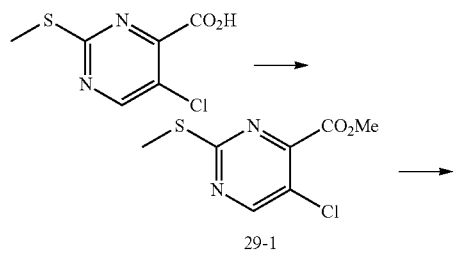

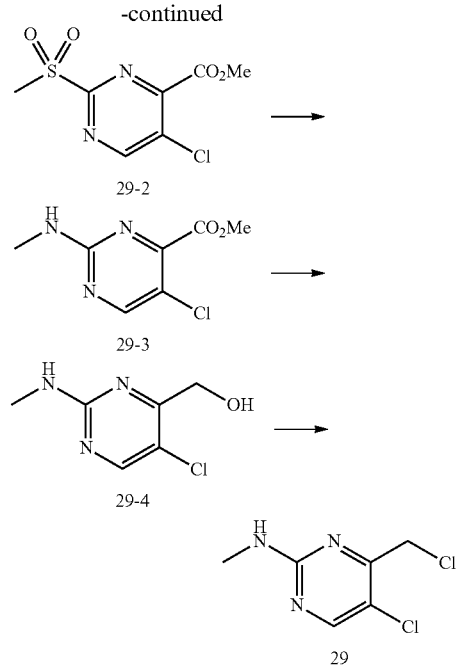

To a solution of 5-chloro-2-(methylthio)pyrimidine-4-carboxylic acid (1.026 g, 5.02 mmol) in 1:1 DCM:methanol was added a solution of trimethylsilyldiazomethane (2M/hexanes, 1.6 mL, 3.2 mmol). The reaction was stirred at RT for 30 min and then concentrated to give the desired 29-1, which was used without further purification. MS (ESI): mass calcd. for C$_7$H$_7$ClN$_2$O$_2$S, 218.0; m/z found 219.1 [M]$^+$.

To a solution of 29-1 (3 mmol) in DCM was added 3-chloroperoxybenzoic acid (70%, 3.156 g, 12.80 mmol). After stirring at RT for 3 hr the reaction mixture was partitioned between DCM (150 mL) and 2M aq K$_2$CO$_3$. The organic layer was washed with brine, dried over MgSO$_4$ and concentrated to give the desired 29-2, which was used without further purification. MS (ESI): mass calcd. for C$_7$H$_7$ClN$_2$O$_4$S, 250.0; m/z found 251.1 [M]$^+$.

To a solution of 29-2 (5 mmol) in DMF was added a solution of methylamine (2M/THF, 5.0 mL, 10.0 mmol) and triethylamine (0.7 mL, 5.0 mmol). After heating at 60° C. for 2 hr the reaction mixture was partitioned between EtOAc (100 mL) and 2:1:1 water:brine:NaHCO$_3$ (100 mL). The organic layer was washed with 2:1:1 water:brine:NaHCO$_3$ (100 mL) and brine, dried over MgSO$_4$ and concentrated. The resulting residue was purified by silica chromatography to give the desired 29-3 in 36% yield. MS (ESI): mass calcd. for C$_7$H$_8$ClN$_3$O$_2$, 201.0; m/z found 202.1 [M]$^+$.

To a solution of 29-3 (1.10 mmol) in THF was slowly added a solution of lithium aluminum hydride (LAH) (1M/THF, 1.2 mL, 1.2 mmol). After stirring at RT for 30 min the reaction was quenched by slowly adding 0.05 mL water, then 0.05 mL 15% aq NaOH, then 0.14 mL water. After stirring at room temperature for 30 min, the reaction mixture was diluted with DCM, dried over MgSO$_4$, filtered through Celite, and concentrated to give the desired 29-4 in 62% yield, which was used without further purification. MS (ESI): mass calcd. for C$_6$H$_8$ClN$_3$O, 173.0; m/z found 174.1 [M]$^+$.

To a solution of 29-4 (1.01 mmol) in 30 mL DCM was added pyridine (0.5 mL, 6.13 mmol) and thionyl chloride (0.2 mL, 2.75 mmol). After stirring at RT for 1.5 hr the reaction was quenched with saturated aqueous NH$_4$Cl and partitioned between DCM (100 mL) and saturated aqueous NaHCO$_3$ (50 mL). The organic layer was dried over MgSO$_4$, concentrated, and purified via silica chromatography to give the desired 29 in 15% yield. MS (ESI): mass calcd. for C$_6$H$_7$Cl$_2$N$_3$, 191.0; m/z found 192.1 [M]$^+$. 1H NMR (400 MHz, DMSO-D6) δ ppm 2.79 (d, 3 H), 4.57 (s, 2 H), 7.51 (s, 1 H), 8.36 (s, 1H).

Example 13

Production and Screening of Fragment Assembly Libraries.

Test fragment libraries are kept in DMSO in 96-well plates with columns 1 through 10 designated for storage of a single unique disulfide test fragment per well, up to 80 in total, and columns 11 and 12 are designated for controls. Test ligand libraries are assembled on a robotic platform in 96-well plates through successive addition of reaction buffer, monomeric library test fragments, and monomeric bait fragments. Upon completion of assembly reactions, reaction mixtures are diluted in DMSO to 20-fold final concentration, and positive and negative controls are then added to columns 11 and 12 of each plate. One point five-microliter (1.5 µL) aliquots of these libraries are transferred to an empty 96-well assay plate and assay reagents are then added according to specific protocol.

Library Assembly through Thioether Chemistry. Eight microliter (8 µL) aliquots of test fragment was added to 2 µL of an aqueous solution of tris(2-carboxyethyl)phosphine HCl (TCEP) and NaOH (final concentration: 25 mM test fragment, 25 mM TCEP, and 175 mM NaOH, 20% water) in 96-well plates. This mixture was incubated for five minutes at 21° C. to produce an activated test fragment solution. 10 µL of purine-mimetic bait fragment was then added to the 96-well plate containing activated fragments at a final concentration of 25 mM bait fragment and 12.5 mM test fragment. This reaction was incubated for at least 4 hr at 21° C.

Alternative Thioether Reaction Conditions. Thioether reactions can also be conducted at lower reagent concentrations than the ones described above. Under these conditions, test fragment is added to TCEP and NaOH, as above, but at a final concentration of 0.5 mM fragment, 0.75 mM TCEP, and 6 mM NaOH. Bait fragment is then added to the activated fragment at a final concentrations of 0.5 mM bait and 0.33 mM test fragment, and incubated at 21° C. for the appropriate duration.

Library Assembly Through Disulfide Chemistry. Ten microliters (10 µL) of purine mimetic bait in Tris-Cl pH 8 buffer was added to a 96-well plate. Ten microliters (10 µL) of test fragment was then added to the bait solution at a final concentration of 1 mM test fragment, 2 mM bait fragment, and 100 mM Tris-Cl pH 8. The reaction was incubated for 1 hr at 21° C.

384-Well Library Screening. Library production and screening can also be conducted in 384-well plate format. In this case, fragment molecules are kept in columns 1 through 22 and controls are kept in columns 23 and 24. For thioether reactions, 10 µL test fragment is added at to 10 µL TCEP and NaOH in 384-well plates and after incubation, 10 µL bait fragment is then added to 20 µL of the activated test fragment. For disulfide reactions, 10 µL test fragment molecule is added to 10 µL purine mimetic bait. For biochemical screening, 1.5 µL aliquots of these libraries are transferred to an empty 384-well assay plate and assay reagents are then added according to specific protocol.

ALK Kinase Assay: Anaplastic lymphoma kinase (ALK) fusion proteins play essential roles in driving oncogenesis in numerous human cancers including non-Hodgkin's lymphomas and non-small cell lung cancer. Accordingly, ALK has received significant attention as an oncology target. See, e.g., Chiarle, R., et al., *Nature Reviews* 8, 11-23 (2008).

ALK kinase assays were conducted using the LanthaScreen® time-resolved FRET assay format (Invitrogen, Carlsbad Calif.). Assay conditions consisted of 15 pM (picomolar) ALK (Invitrogen PV3867), 10 µM ATP, and 100 nM substrate peptide FL-polyGT (Invitrogen PV3610) diluted in assay buffer (10 mM Tris pH 7.2, 10 mM MgCl, 1 mM DTT, 100 µM Na$_2$OVO$_4$. 0.01% Triton® X-100, 0.05% Casein). Control compounds and fragment-assembly reaction mixtures were diluted in DMSO to generate stock compounds at 20-fold final concentration. For IC$_{50}$ assays, fragment-assembly reaction mixtures were titrated three-fold in DMSO and diluted 20-fold into the assay mixture. As a positive control for enzyme activity, the reaction mixture was added to DMSO, and, as a negative control for enzyme activity, the reaction mixture was added to staurosporine (Sigma) at a final concentration of 20 µM. Reactions were terminated after incubation at 30° C. for 45 min by addition of 30 µL of detection buffer (90% TR-FRET dilution buffer (Invitrogen PV3574), 20 mM EDTA, 4.0 nM TB-PY20 antibody (Invitrogen PV3529). Following subsequent incubation for 1 hr, the degree of kinase activity was measured by change in fluorescence ratio units detected using an LJL Analyst assay detection system (LJL Biosystems). Relative enzymatic activity values were plotted as a function of the logarithm of compound concentration ("x") and IC$_{50}$ values were generated in GraphPad Prism software version 4.01 using Equation (2) described above.

Fragment Library Pilot Screen. Fragment-assembly reaction mixtures were screened in 384-well plates at a concentration approximating 5-fold lower than that of the purine-mimetic bait fragment IC$_{50}$ value, in single-point format in the ALK assay as described above. Reaction mixtures resulting in greater than or equal to 50% inhibition of enzymatic activity were then confirmed in single-point format, or tested in an IC$_{50}$ assay. LC/MS analysis was conducted on fragment assembly screening plates to confirm the presence of desired test ligand in the reaction mixture. Confirmed hits were then resynthesized as purified thioether compounds and tested in an IC$_{50}$ assay.

Iterative Chemotype Evolution

ALK and the inhibitor Compound 30 [Galkin, A. V., et al., *Proc. Nat'l Acad. Sci. USA* 104, 270-275 (2007)] was employed in a proof-of-concept study. Compound 30 can be deconstructed into a series of pharmacophores of potential use as bait moieties. A series of bait fragments containing some exemplary pharmacophores and reactive functionalities was synthesized as described herein; the bait fragments maintained sufficient activity to be detected in an enzymatic kinase reaction (Table 6). Bait fragments were prepared for use in disulfide exchange chemistry (Compounds 26 and 27) and for thioether chemistry (Compounds 28 and 29).

Table 6

| | Structure | IC$_{50}$ (μM) |
|---|---|---|
| 30 | [structure: 4-methylpiperazine-piperidine-methoxyphenyl-NH-(5-chloropyrimidine)-NH-phenyl-SO$_2$-isopropyl] | <0.001 |
| 27 | [structure: HS-CH$_2$CH$_2$-NH-(5-chloropyrimidine)-NH-phenyl-SO$_2$-isopropyl] | 0.25 |
| 26 | [structure: 2-methoxyphenyl-NH-(5-chloropyrimidine)-NH-CH$_2$CH$_2$-SH] | 0.50 |
| 28 | [structure: methyl-NH-(5-chloropyrimidine)-NH-(3-chloromethyl)phenyl] | 3.75 |
| 29 | [structure: methyl-NH-(5-chloropyrimidine)-CH$_2$Cl] | 7.80 |

To identify novel ALK inhibitors, a fragment library of 5050 compounds was screened in combination with purine mimetic bait fragment Compound 28 against ALK. Fragment reactions were tested in single-point format at a concentration of 0.75 μM, which is 5-fold lower than the 3.7 μM IC$_{50}$ value for the Compound 28 purine mimetic bait fragment and cystamine control reactions. Screening the test fragment library at this concentration allowed for the detection of synergy between the bait fragment and test fragment molecules since bait fragment alone would not be present at a high enough concentration to significantly reduce ALK enzymatic activity.

Hits were defined as fragment reactions with greater than or equal to 50% inhibition of enzymatic activity. The hit rate was 0.6%. Of the 30 different fragments identified as hits, 20 were selected to confirm inhibitory activity against ALK with IC$_{50}$ reactions. IC$_{50}$ values were calculated relative to the concentration of fragment molecule present in the kinase reaction. As a control for bait-independent activity, the test fragment library was also screened in the absence of purine mimetic bait fragments. Three representative hits, hit fragment IC$_{50}$, and library assembly mixture IC$_{50}$ are presented in Table 7.

Table 7

| Bait | Hit | Fragment IC$_{50}$ (µM) | Assembled IC$_{50}$ (µM) |
|---|---|---|---|
| (compound 28) | (compound 31) | 1.62 | 0.18 |
| | (compound 32) | 2.00 | 0.16 |
| | (compound 33) | 6.64 | 0.27 |

Synergy ranges from 10- to 25-fold versus the fragment-dependent activity. The product mixture (28 +32) has an IC$_{50}$ of 160 nM, which is more than twelve-fold below the 2.0 µM IC$_{50}$ for Compound 32. Since the control reaction consisting of Compound 28 and cysteamine has an IC$_{50}$ of 3.7 µM, the potent inhibition by the reaction mixture can be attributed to the presence of Compound 32.

The present example illustrates how a structurally simple bait fragment identified from a validated ALK inhibitor can be used to gain wider coverage of the relevant chemical space, and thereby produce an inhibitor possessing novel chemotype.

All references cited herein are incorporated by reference as if each had been individually incorporated by reference in its entirety. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A method for screening a compound that binds to a target, comprising performing a first screening procedure comprising:
    (a) preparing a plurality of individual reaction mixtures by reacting a bait fragment B-x, comprising a preselected bait moiety B and a reactive functionality x, wherein x is selected from the group consisting of halo groups, thiols, disulfides, acrylamides, acrylates, vinyl sulfones, epoxides, thiiranes, aziridines, esters, sulfonic acid esters, thioesters, alkynes, and azides, with a plurality of naïve test fragments (y-T$_1$, y-T$_2$, . . . y-T$_n$, each test fragment comprising a reactive functionality y, wherein y is selected from the group consisting of disulfides, thiols, amines, alcohols, phenols, alkynes, and azides, and one of a plurality of naïve test moieties (T$_1$, T$_2$, . . . T$_n$) under conditions sufficient to form a plurality of n test ligands (B-z-T$_1$, B-z-T$_2$, . . . B-z-T$_n$), wherein each of B-z-T$_1$, B-z-T$_2$, . . . B-z-T$_n$ is prepared individually in one of a multiplicity of containers and wherein z is a linker formed by reaction of x and y;
    (b) without purification of the reaction mixtures of (a), individually contacting the target with one or more of the reaction mixtures of (a) under conditions that permit binding between the target and a test ligand that binds thereto, wherein binding between the target and at least one of the test ligands provides at least one test ligand:target complex; and
    (c) assessing the presence or absence of binding of at least one of the test ligands to the target;
wherein said method does not utilize mass spectrometric detection of a test ligand released from a test ligand:target complex
and wherein the z does not comprise a disulfide moiety.

2. The method of claim 1, wherein the target is a protein.

3. The method of claim 2, wherein (c) comprises measuring a binding affinity between the protein and a test ligand.

4. The method of claim 3, wherein the binding affinity is measured by determining a member selected from the group consisting of a biological activity of the protein, a conformational state of the protein, a dissociation constant of a test ligand for the protein, an affinity constant of a test ligand for the protein, a melting temperature of the protein, and a denaturing temperature for the protein.

5. The method of claim 2, wherein the protein is an enzyme.

6. The method of claim 5, wherein the enzyme is a kinase.

7. The method of claim 1, wherein the preselected bait moiety:
   (a) selectively binds the target;
   (b) selectively modulates a functional or structural property of the target;
   (c) comprises a portion of a compound that selectively binds the target; or
   (d) is an analog of a compound that selectively binds the target.

8. The method of claim 2, wherein the preselected bait moiety:
   (a) selectively binds the protein;
   (b) selectively modulates a functional or structural property of the protein;
   (c) comprises a portion of a compound that selectively binds the protein; or
   (d) is an analog of a compound that selectively binds the protein.

9. The method of claim 1, wherein x is selected from the group consisting of halo groups, thiols, disulfides, acrylamides, acrylates, vinyl sulfones, epoxides, thiiranes, aziridines, esters, sulfonic acid esters, and thioesters.

10. The method of claim 1, wherein y is selected from the group consisting of disulfides, thiols, amines, alcohols, phenols.

11. The method of claim 1, wherein z is —O—, —N—, —S—, or a 2-10 atom heteroaliphatic group having at least one heteroatom selected from the group of O, N, and S in the heteroaliphatic backbone.

12. The method of claim 1, wherein z comprises a thioether moiety.

13. The method of claim 1, wherein the reacting is performed under conditions permitting reversible reaction of x and y.

14. The method of claim 13, wherein y comprises a disulfide moiety.

15. The method of claim 14, wherein the reacting further comprises adding a reductant selected from the group consisting of beta-mercaptoethanol, mercaptopropanoic acid, glutathione, cysteamine, dithiothreitol, dithioerythritol, cysteine, homocysteine, triphenylphosphine, tris(cyanoethyl) phosphine, and tris-2-carboxyethylphosphine hydrochloride.

16. The method of claim 1, wherein the reacting occurs at physiological conditions.

17. The method of claim 16, wherein (a) and (b) temporally overlap.

18. The method of claim 1, wherein the reacting occurs under conditions that would disrupt or degrade the target.

19. The method of claim 1, further comprising:
   (d) identifying at least one test ligand that binds to the target.

20. The method of claim 19, wherein (d) comprises identifying a test ligand having a binding affinity for the target that is higher than the binding affinity of the preselected bait moiety, the bait fragment, or a structural analog thereof.

21. The method of claim 19, wherein (d) comprises identifying a test ligand having a binding affinity for the target that is higher than the binding affinity of a composition comprising the preselected bait moiety and the test moiety of the test ligand being identified.

22. The method of claim 19, further comprising a second screening procedure, comprising:
   (a') providing a plurality of test ligands ($B'$-$z$-$T'_1$, $B'$-$z$-$T'_2$, ... $B'$-$z$-$T'_n$), each comprising a bait moiety $B'$ attached via a linker z to one of a plurality of test moieties ($T'_1$, $T'_2$, ... $T'_n$); wherein the bait moiety $B'$ comprises the test moiety of a test ligand identified in (d);
   (b') contacting the target with the plurality of test ligands provided in (a') under conditions that permit binding between the target and a test ligand that binds thereto;
   (c') assessing the presence or absence of binding between a test ligand and the target; and
   (d') identifying a test ligand that binds to the target in (c').

23. The method of claim 22, wherein the target is a protein.

24. The method of claim 1, wherein each of the test ligands ($B$-$z$-$T_1$, $B$-$z$-$T_2$, ... $B$-$z$-$T_n$) have a different mass.

25. The method of claim 24, wherein the masses of the test ligands ($B$-$z$-$T_1$, $B$-$z$-$T_2$, ... $B$-$z$-$T_n$) differ from each other by at least 0.1 Da.

26. The method of claim 1, wherein the bait moiety B has a mass of less than about 450 Da.

27. The method of claim 26, wherein the bait moiety B has a mass of from about 150 Da to about 350 Da.

28. The method of claim 1, wherein the bait fragment B-x has a mass of less than about 600 Da.

29. The method of claim 28, wherein the bait fragment B-x has a mass of from about 250 Da to about 500 Da.

30. The method of claim 29, wherein the bait fragment B-x has a mass of from about 300 Da to about 400 Da.

31. The method of claim 1, wherein each test moiety ($T_1$, $T_2$, ... $T_n$) has a mass of less than about 500 Da.

32. The method of claim 31, wherein each test moiety ($T_1$, $T_2$, ... $T_n$) has a mass of from about 150 Da to about 400 Da.

33. The method of claim 1, wherein each test ligand ($B$-$z$-$T_1$, $B$-$z$-$T_2$, ... $B$-$z$-$T_n$) has a mass of less than about 1000 Da.

34. The method of claim 33, wherein each test ligand ($B$-$z$-$T_1$, $B$-$z$-$T_2$, ... $B$-$z$-$T_n$) has a mass of from about 350 Da to about 600 Da.

35. The method of claim 1, wherein (b) comprises individually contacting each of the reaction mixtures with the target.

36. The method of claim 1, wherein n is from 2 to 100,000.

37. The method of claim 36, wherein n is from 2 to 25,000.

38. The method of claim 37, wherein n is from 2 to 2,500.

39. The method of claim 38, wherein n is from 2 to 1,000.

40. The method of claim 39, wherein n is from 2 to 500.

41. The method of claim 22, wherein the test moieties of the test ligands in (a') are identical to the test moieties of the test ligands in (a).

42. The method of claim 22, wherein the test moieties of the test ligands in (a') are different from the test moieties of the test ligands in (a).

43. The method of claim 19, wherein (c) comprises isolating at least one test ligand:target complex formed in (b) from test ligands that are not bound to the target; and (d) comprises identifying the test moiety of at least one test ligand:target complex.

44. The method of claim 43, wherein (c) comprises isolating at least one test ligand:target complex by gel permeation chromatography or size exclusion chromatography.

45. The method of claim 43, wherein (d) comprises identifying the test fragment by mass spectrometric analysis of the test ligand:target complex.

46. The method of claim 19 or 22, further comprising:
(e) synthesizing a derivative test ligand comprising the bait moiety (B or B') of (a) or (a') linked to the test moiety of the test ligand identified in (d) or (d'), wherein the bait moiety and the identified test moiety are linked through a linker z' that is different from the linker z of the test ligand identified in (d) or (d');
(f) contacting the target with the derivative test ligand under conditions that permit binding of the target with test ligands that bind thereto; and
(g) assessing binding between the derivative test ligand and the target by measuring the binding affinity of the derivative test ligand for the target.

47. The method of claim 2, wherein
the preselected bait moiety B has, or comprises a fragment of a compound that has, binding affinity for the protein;
the presence or absence of binding of at least one of the test ligands to the protein is assessed by measuring the binding affinity of a test ligand for the protein;
the first screening procedure further comprises:
(d) identifying a test ligand having a binding affinity for the protein that is higher than the binding affinity of the preselected bait moiety;
said method further comprising performing a second screening procedure, comprising:
(a') contacting a plurality of test ligands with a protein under conditions that permit binding between the protein and a test ligand that binds thereto, wherein each test ligand comprises a bait moiety attached to one of a plurality of test moieties, and wherein the bait moiety has, or comprises a fragment of a compound that has, binding affinity for the protein;
(b') assessing the presence or absence of binding between a test ligand and the protein by measuring the binding affinity of the test ligand for the protein; and
(c') identifying a test ligand having a binding affinity for the protein that is higher than the binding affinity of the bait moiety employed in (a');
wherein the second screening procedure employs as the bait moiety a test moiety identified in the first screening procedure or a structural analog of the test moiety identified in the first screening procedure.

48. The method of claim 42, further comprising:
(e) providing purified test ligand identified in (d); and
(f) measuring the binding affinity of the purified test ligand for the target to confirm the identification of the test ligand.

49. The method of claim 2, wherein the first screening procedure further comprises:
(d) identifying the at least one test ligand that binds to the protein; said method further comprising performing a second screening procedure, wherein the second screening procedure employs as the bait moiety a test moiety identified in the first screening procedure or a structural analog of the test moiety identified in the first screening procedure.

50. The method of claim 2, wherein each reaction mixture is contained individually in one of a multiplicity of containers.

51. The method of claim 50 wherein said multiplicity of containers comprises a multi-well plate.

52. The method of claim 1, wherein x and y are independently selected from the group consisting of alkynes and azides.

53. The method of claim 1, wherein (a) is performed in the absence of target.

54. The method of claim 1, wherein said method does not utilize mass spectrometric detection.

55. A method for screening a compound that binds to a target, comprising performing a first screening procedure comprising:
(a) preparing a plurality of individual reaction mixtures by reacting a bait fragment B-x, comprising a preselected bait moiety B and a reactive functionality x, wherein x is selected from the group consisting of halo groups, thiols, disulfides, acrylamides, acrylates, vinyl sulfones, epoxides, thiiranes, aziridines, esters, sulfonic acid esters, thioesters, alkynes, and azides, with a plurality of naïve test fragments ($y$-$T_1$, $y$-$T_2$, ... $y$-$T_n$), each test fragment comprising a reactive functionality y, wherein y is selected from the group consisting of disulfides, thiols, amines, alcohols, phenols, alkynes, and azides, and one of a plurality of naïve test moieties ($T_1$, $T_2$, ... $T_n$) under conditions sufficient to form a plurality of n test ligands (B-z-$T_1$, B-z-$T_2$, ... B-z-$T_n$), wherein each of B-z-$T_1$, B-z-$T_2$, ... B-z-$T_n$ is prepared individually in one of a multiplicity of containers and wherein z is a linker formed by reaction of x and y;
(b) without purification of the reaction mixtures of (a), individually contacting the target with one or more of the reaction mixtures of (a) under conditions that permit binding between the target and a test ligand that binds thereto, wherein binding between the target and at least one of the test ligands provides at least one test ligand:target complex; and
(c) assessing the presence or absence of binding of at least one of the test ligands to the target;
wherein (c) employs: an assay selected from fluorescence polarization (FP) assays, homogeneous time-resolved fluorescence (HTRF) assays, time resolved fluorescence resonance energy transfer (TR-FRET) assays, and enzyme-linked immunosorbent assays (ELISA); or a method selected from High Content Screening (HCS) methods, cell cycle analysis methods, and substrate phosphorylation methods and wherein the z does not comprise a disulfide moiety.

56. The method of claim 1 or 55, wherein the bait moiety has a potential binding affinity for the target.

57. The method of claim 1 or 55, wherein the bait moiety has a measurable binding affinity for the target.

* * * * *